(12) United States Patent
Baker et al.

(10) Patent No.: US 8,834,408 B2
(45) Date of Patent: Sep. 16, 2014

(54) IRRIGATION AND ASPIRATION DEVICES AND METHODS

(75) Inventors: Peter C. Baker, Ross, CA (US); Clinton N. Slone, San Francisco, CA (US); Michael J. Strasser, San Francisco, CA (US); James M. Lovette, Half Moon Bay, CA (US); Thomas King, San Francisco, CA (US); Richard Treadwell, San Francisco, CA (US)

(73) Assignee: Aardvark Medical, Inc., Ross, CA (US)

( * ) Notice: Subject to any disclaimer, the term of this patent is extended or adjusted under 35 U.S.C. 154(b) by 1074 days.

(21) Appl. No.: 12/387,054

(22) Filed: Apr. 27, 2009

(65) Prior Publication Data

US 2009/0281454 A1    Nov. 12, 2009

Related U.S. Application Data

(63) Continuation of application No. 11/936,042, filed on Nov. 6, 2007, now Pat. No. 7,959,597.

(60) Provisional application No. 60/857,457, filed on Nov. 6, 2006, provisional application No. 60/944,079, filed on Jun. 14, 2007.

(51) Int. Cl.
*A61M 1/00* (2006.01)
*A61M 11/00* (2006.01)
*A61M 3/02* (2006.01)

(52) U.S. Cl.
CPC ......... *A61M 1/0058* (2013.01); *A61M 2205/82* (2013.01); *A61M 1/0072* (2014.02); *A61M 1/0062* (2013.01); *A61M 11/00* (2013.01); *A61M 1/0009* (2013.01); *A61M 11/008* (2014.02); *A61M 2210/0618* (2013.01); *A61M 2209/086* (2013.01); *A61M 1/0052* (2014.02); *A61M 3/0262* (2013.01); *A61M 3/0258* (2013.01)
USPC .................... 604/27; 604/28; 604/30; 604/35

(58) Field of Classification Search
USPC .................. 604/28, 30, 118–121, 27, 35, 173
See application file for complete search history.

(56) References Cited

U.S. PATENT DOCUMENTS 1,603,758 A 10/1926 Fisher
1,856,811 A 5/1932 Inaki et al.
(Continued)

FOREIGN PATENT DOCUMENTS

WO WO 2006/051206 5/2006
WO WO 2008/058160 5/2008
WO WO 2010/126586 11/2010

OTHER PUBLICATIONS

International Preliminary Report on Patentability dated Apr. 25, 2011 in International Patent Application Serial No. PCT/US2010/001243.

(Continued)

*Primary Examiner* — Kami A Bosworth
*Assistant Examiner* — Imani Hayman
(74) *Attorney, Agent, or Firm* — Levine Bagade Han LLP

(57) ABSTRACT

Irrigation and/or aspiration devices and methods may be configured to aspirate and irrigate alone, sequentially, or concurrently. The devices and methods may provide a base with a removable head, and adapted for partial or complete separation of the irrigation and aspiration functions. The devices and methods can be configured to aspirate and/or irrigate the nasal and sinus cavities. The devices and methods may be manually and/or automatically controlled. The devices and methods may include removable, and/or replaceable, and/or refillable, and easily cleanable reservoirs for aspirant and irrigant. The device head and/or aspirant reservoir may comprise a diagnostic device, i.e., test device and/or container after use of the devices and methods.

19 Claims, 26 Drawing Sheets

(56) References Cited

U.S. PATENT DOCUMENTS

| | | |
|---|---|---|
| 2,511,973 A | 6/1950 | de la Sierra |
| 2,566,806 A | 9/1951 | Miller et al. |
| 2,890,699 A | 6/1959 | Miller |
| 4,403,611 A | 9/1983 | Babbitt et al. |
| 4,776,840 A | 10/1988 | Freitas et al. |
| 5,024,653 A | 6/1991 | Kohnke |
| 5,062,835 A | 11/1991 | Maitz et al. |
| 5,098,418 A | 3/1992 | Maitz et al. |
| 5,114,415 A | 5/1992 | Shedlock |
| 5,318,548 A | 6/1994 | Filshie |
| 5,649,530 A | 7/1997 | Ballini |
| 5,788,683 A | 8/1998 | Martin |
| 5,800,425 A | 9/1998 | DeLeonardis |
| 6,135,980 A | 10/2000 | Vu |
| 6,149,622 A | 11/2000 | Marie |
| 6,238,377 B1 | 5/2001 | Liu |
| 6,328,718 B1 | 12/2001 | Chiang et al. |
| 6,413,228 B1 * | 7/2002 | Hung et al. ............ 600/562 |
| 6,517,511 B2 | 2/2003 | Yao |
| 6,520,931 B2 | 2/2003 | Suh |
| 6,595,949 B1 | 7/2003 | Shapiro |
| 6,675,994 B2 | 1/2004 | Yamamoto et al. |
| 6,736,792 B1 | 5/2004 | Liu |
| 6,893,414 B2 | 5/2005 | Goble et al. |
| 6,907,879 B2 | 6/2005 | Drinan et al. |
| 7,143,763 B2 * | 12/2006 | Abate ............... 128/200.14 |
| 7,435,252 B2 | 10/2008 | Krespi et al. |
| 7,959,597 B2 | 6/2011 | Baker et al. |
| 7,998,679 B2 * | 8/2011 | Jacobs et al. ............ 435/6.11 |
| 8,414,521 B2 | 4/2013 | Baker et al. |
| 8,435,207 B2 | 5/2013 | Baker et al. |
| 2003/0145849 A1 * | 8/2003 | Drinan et al. ........ 128/200.14 |
| 2005/0197645 A1 | 9/2005 | Karpowicz et al. |
| 2006/0272650 A1 | 12/2006 | Hoogenakker et al. |
| 2006/0276743 A1 | 12/2006 | MacMahon et al. |
| 2008/0154183 A1 | 6/2008 | Baker et al. |
| 2008/0221507 A1 | 9/2008 | Hoke et al. |
| 2009/0281483 A1 | 11/2009 | Baker et al. |
| 2009/0281485 A1 | 11/2009 | Baker et al. |
| 2011/0184341 A1 | 7/2011 | Baker et al. |

OTHER PUBLICATIONS

Nilars, Mikkel S., "Nozzle technology and Atomizer design," Hardi International A/S, 10 pages, 1998.

Wolfe, T.R. et al, "The Comparative Risks of Bacterial Contamination between a Venturi Atomizer and a Positive Displacement Atomizer," *American Journal of Rhinology*, 16:4, 1 page, abstract only, Jul. 2002, Oceanside Publications, Inc.

* cited by examiner

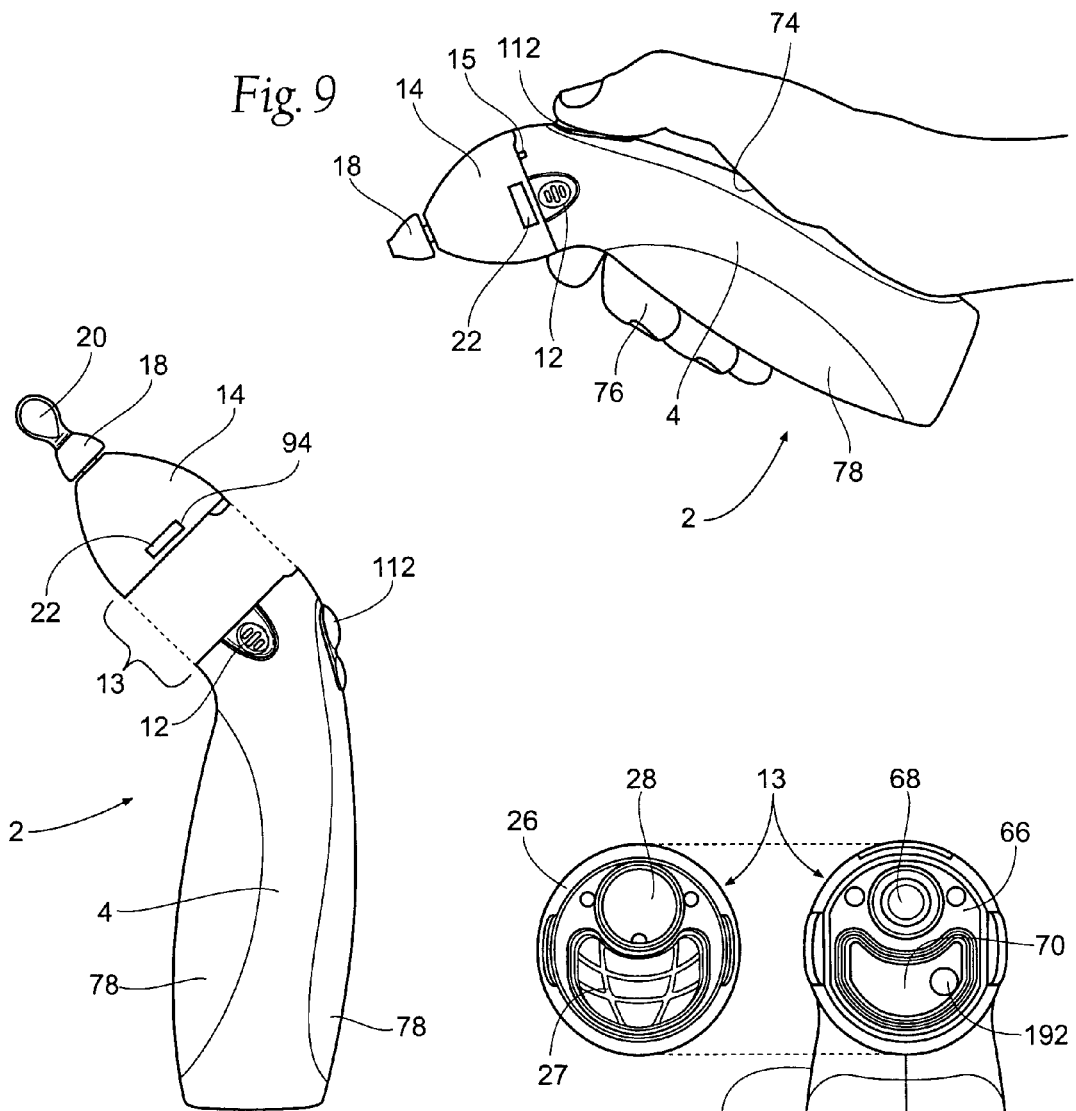
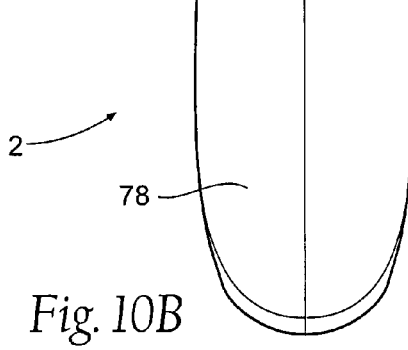

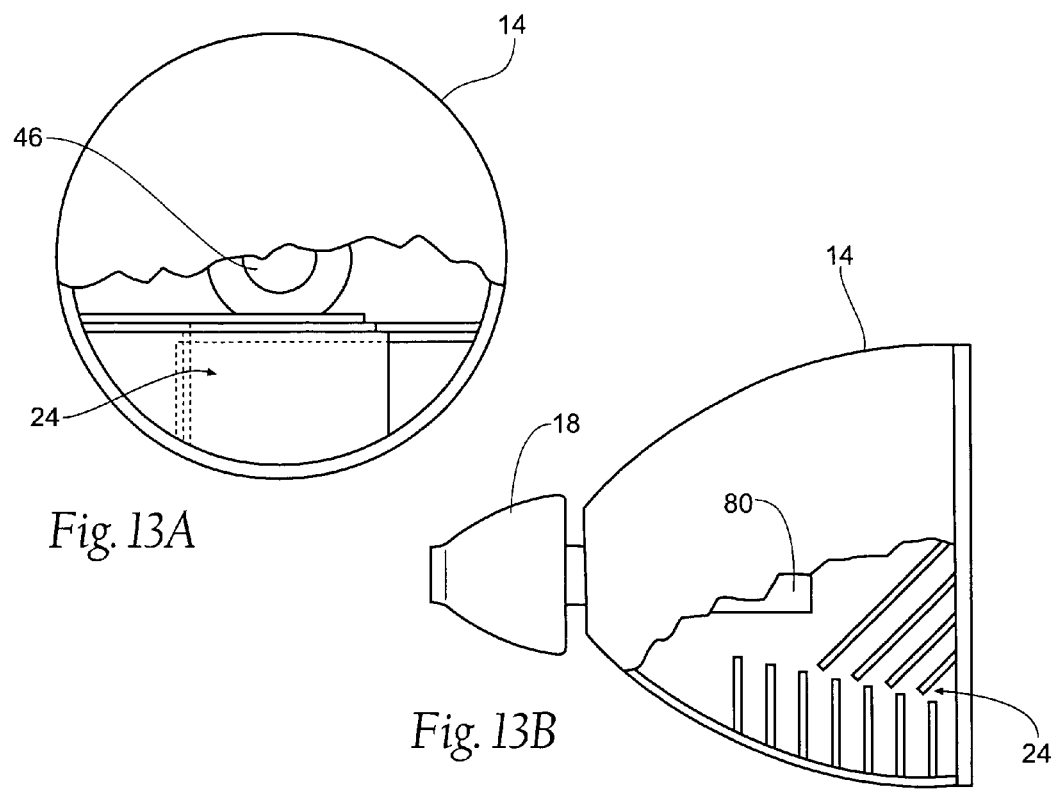
Fig. 13A
Fig. 13B
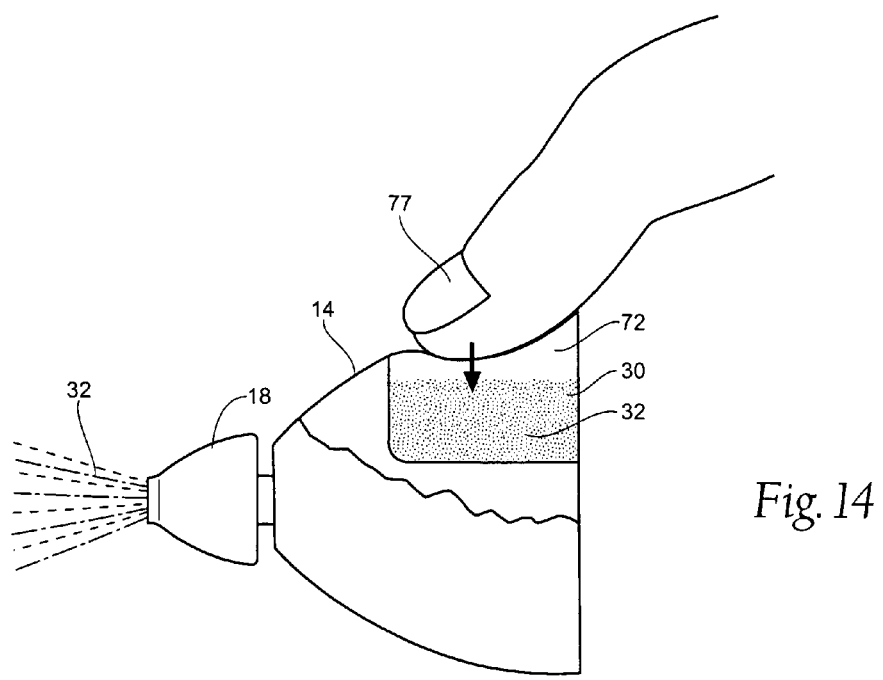
Fig. 14

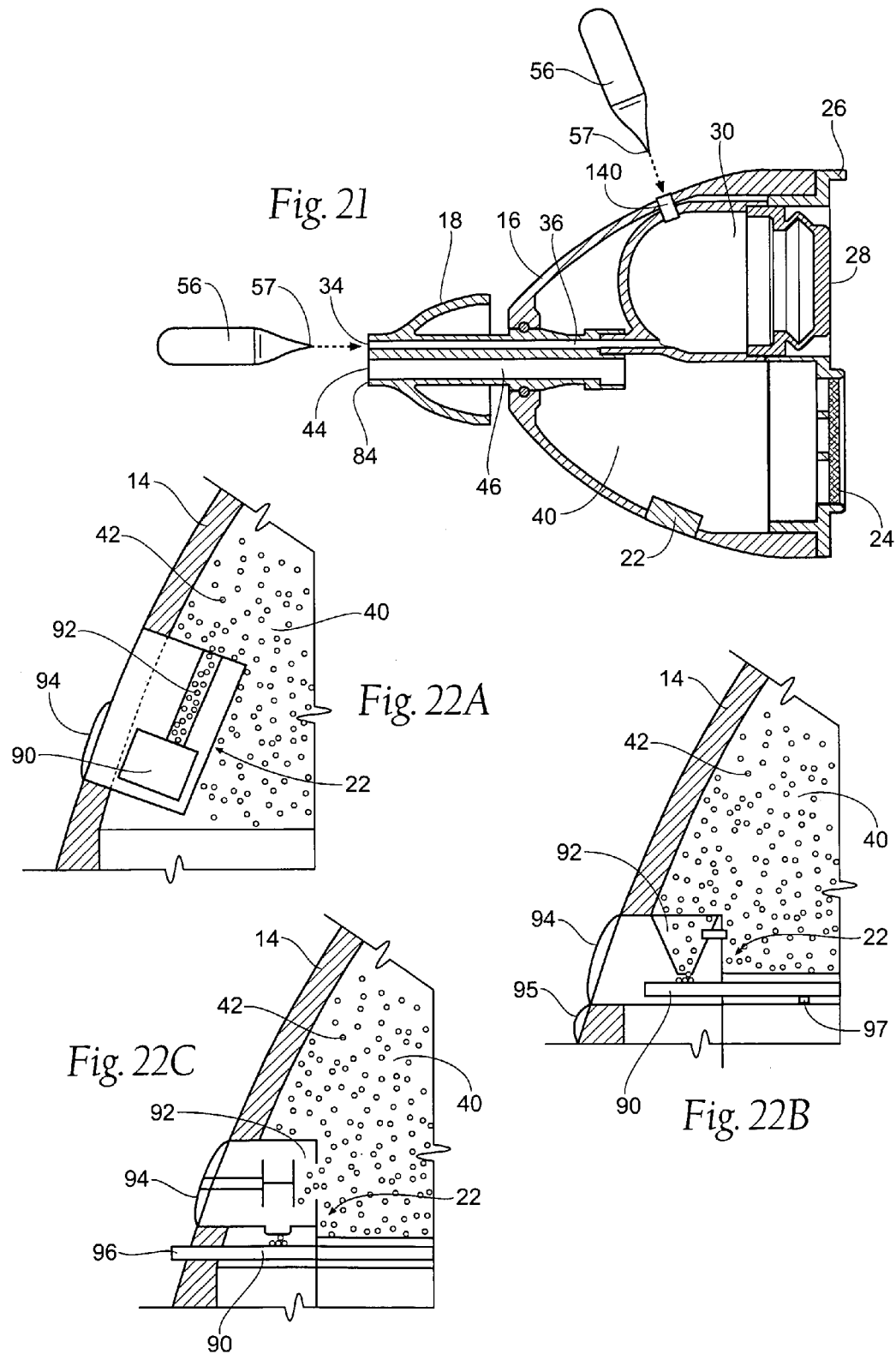

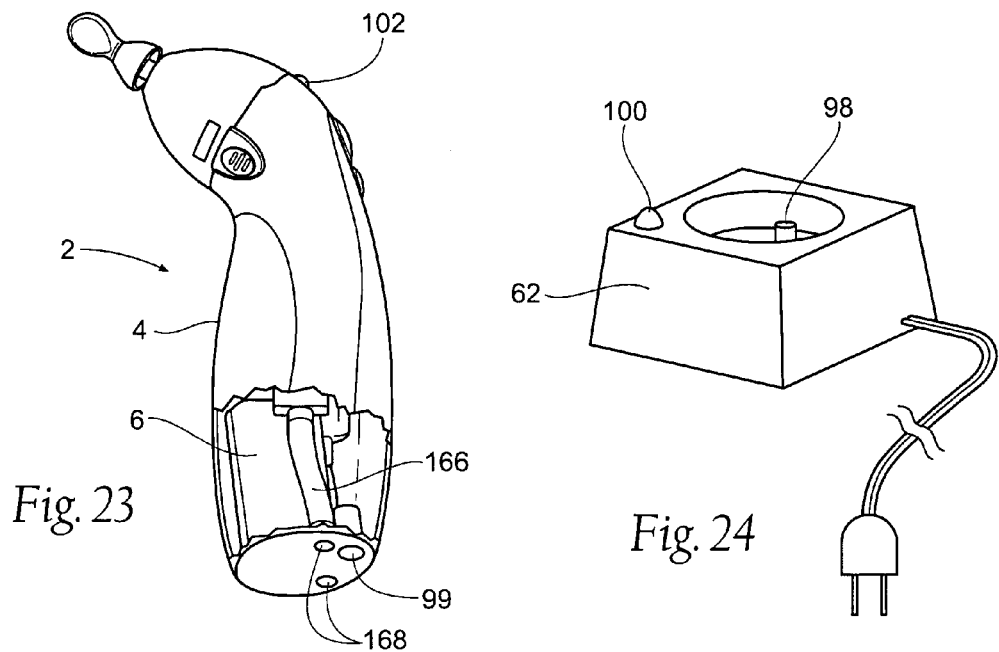
Fig. 23
Fig. 24
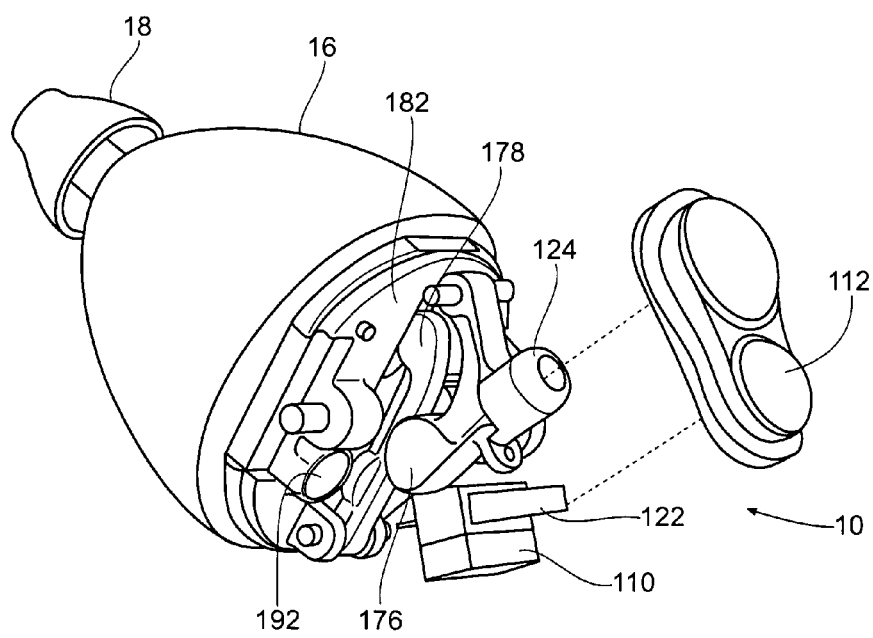
Fig. 25

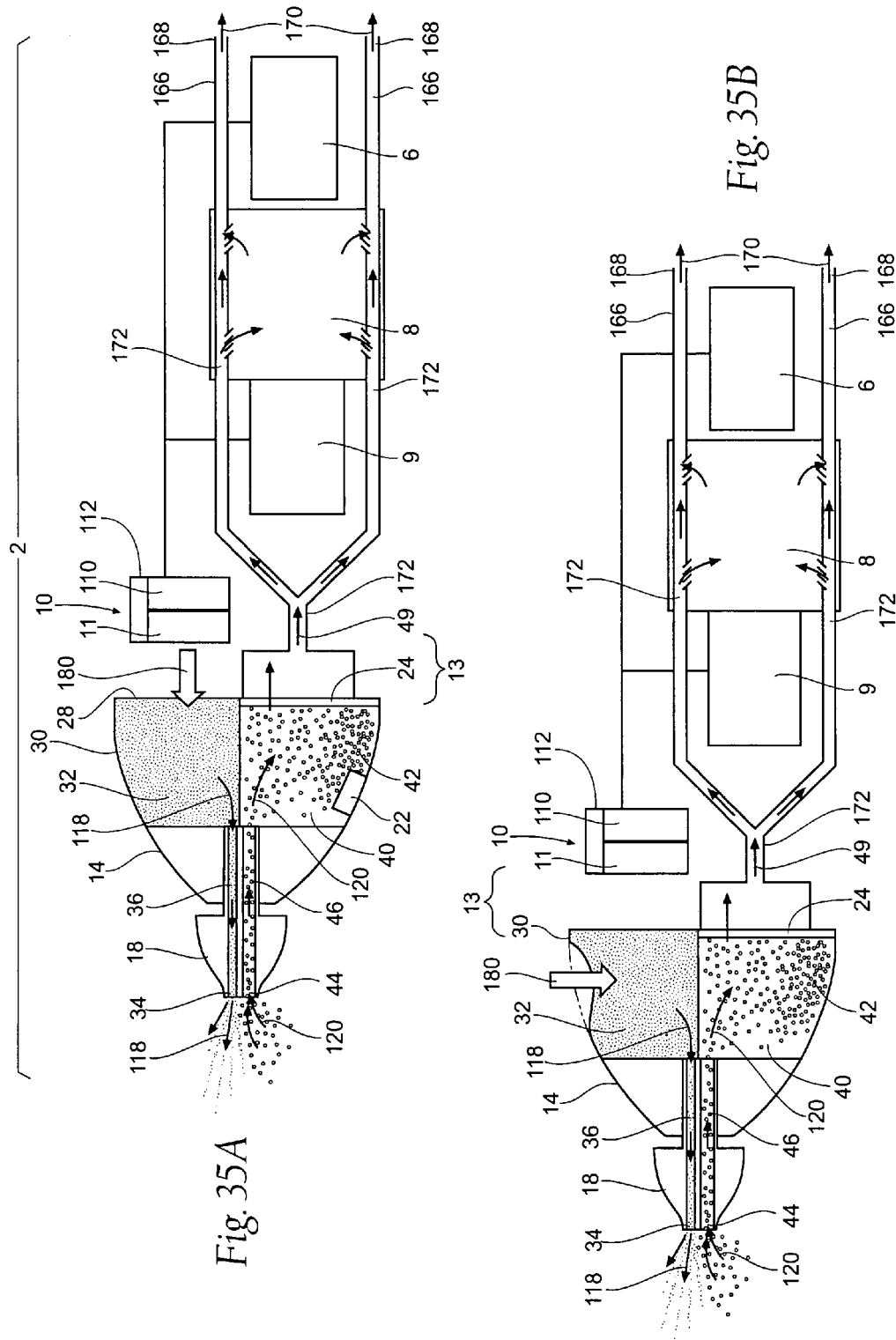

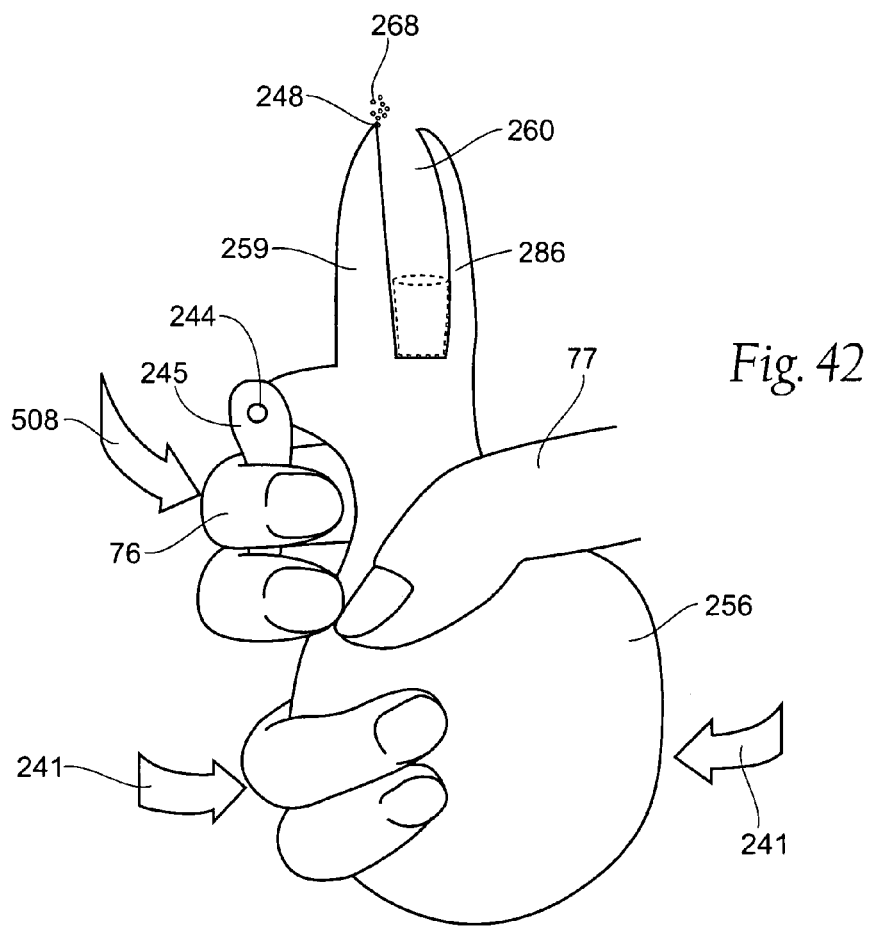
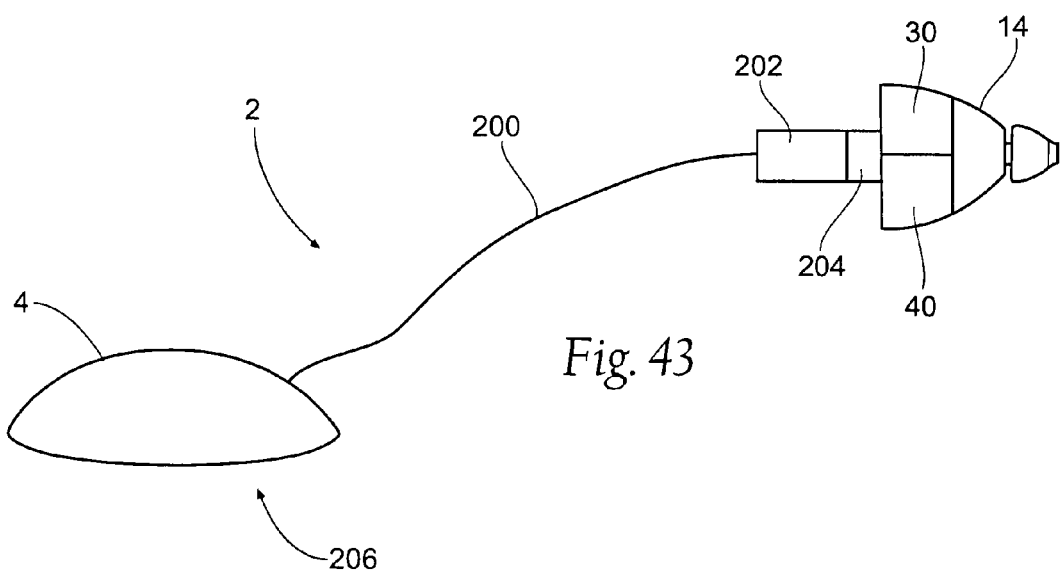

IRRIGATION AND ASPIRATION DEVICES AND METHODS

RELATED APPLICATIONS

This application is a continuation-in-part of U.S. patent application Ser. No. 11/936,042, filed 6 Nov. 2007, and entitled "Irrigation and Aspiration Device and Method," now U.S Pat. No. 7,959,597, issued Jun. 14, 2011, which claims priority to U.S. Provisional Application Ser. No. 60/857,457, filed 6 Nov. 2006, and U.S. Provisional Application Ser. No. 60/944,079, filed 14 Jun. 2007, all of which are incorporated by reference herein in their entireties.

FIELD OF THE INVENTION

The present invention relates generally to the field of medicine, and more specifically to cavity, i.e., nasal aspiration and irrigation, as administered in a medical setting, as well as in the home. In particular, the present devices and methods may be able to aspirate and irrigate simultaneously through one or more nozzles or catheters. Both actions may be controlled separately or simultaneously by one or more switches.

BACKGROUND OF THE INVENTION

Nasal and sinus congestion is a ubiquitous problem in children and adults. Viral illnesses and environmental allergies in about 100 million Americans per year cause myriad symptoms including rhinitis (i.e., nasal inflammation), which causes congestion, rhinnorhea, and sinus blockage. This in turn can cause sinusitis, or more commonly, irritation, pain, and nasal cavity blockage, which causes poor sleeping and feeding in infants and general discomfort and malaise in adults.

Diagnosis of the many potential conditions has been a tedious process at best. Samples of mucus and/or nasal tissues must be taken and placed in a vial or specimen container. The sample is then typically sent to a lab for analysis, which may take hours, or longer, before results are returned and a treatment regimen can be prescribed.

Current strategies for dealing with nasal and sinus congestion include several types of orally and nasally administered over the counter therapies, such as decongestants and antihistamines, as well as prescription drugs such as steroids and antibiotics. While these solutions offer some relief, they entail serious drawbacks: they are expensive, results are variable, and side-effects include rebound congestion, hypertension, habit formation, and possible medical interactions. In pediatrics, there is no proven safe and effective over the counter solution. Partial relief of congestion may also be met by blowing the nose, which may eventually be irritating to the adult and difficult or impossible for a child or infant.

For these reasons, physicians have been turning increasingly to the age-old remedy of saline irrigation. Recently, several physician societies have indicated saline irrigation as an adjunct therapy in their practice guidelines, and nasal and sinus lavage is now commonly prescribed, especially in pediatrics. Yet despite the increased interest in saline therapy, there is currently no adequate system for performing it.

It has been shown that nasal suctioning, alone or following saline irrigation, is an effective way of relieving symptoms and signs of rhinitis. Nasal suctioning can circumvent the side effects of medicines and irritation—or the impossibility—of nose blowing. Manual aspirators have long been used for nasal suctioning in infants. However, they do not provide enough airflow nor adequate evacuation time. As a result, they are variably efficacious and can be awkward and frustrating to use. Typical sinus irrigators designed for adults with sinusitis do not circumvent the problem of painful evacuation or blowing.

Furthermore, nasal congestion from viral respiratory infections causes difficulties with sleeping and eating in infants as they are obligate nose breathers. This leads to poor nutrition and restlessness which may disrupt both the child's well being and the family's functioning. Worse, unresolved nasal congestion as part of an infant's viral syndrome can lead to emergency department visits or hospitalization for supplemental oxygen, frequent suctioning, and parenteral nutrition.

Several strategies are used to resolve nasal congestion. Several studies have demonstrated futility of cold medications in relieving symptoms, and most parents learn that nasal irrigation and suctioning is the best option. Routine nasal irrigation improves symptoms in adults with chronic rhinosinusitis as well as children with allergic rhinitis. Additionally, several studies have shown that saline irrigation improves nasal ciliary motility. It is thought that the saline draws fluid from the submucosal and adventitial space decreasing airway edema and softening the mucus, allowing easier suctioning. Additionally, the saline is thought to stimulate channels in the cell membrane which improves the cell's function.

Such a combination of saline irrigation and suctioning has proven benefits, especially for infants with bronchiolitis. Most studies evaluating nasal suctioning used a hospital's central "wall" suction and some studies even used deep nasopharyngeal suctioning, both of which are not routinely available for clinic or home use. The studies demonstrated that appropriate suctioning reduces the need for further interventions, such as nebulizations, oxygen supplementation, and hospital admissions.

In contrast to hospital wall suction, manual nasal aspirators are available for home use. Their maximal negative pressure and flow rates are generally adequate, but their air flow is uncontrolled, hard to keep a seal on the nostril, and very brief, and they require repeated movements to and from the nose. Both parameters contribute to their imperfect quality; more pressure has been shown to be optimal (80 to 100 mmHg, for example) and the short duration of their action requires repeated attempts back and forth, rendering them awkward.

Typical bulb suction syringes offer some suction, but brief and uncontrolled pressures can limit their utility. Additionally, the narrow and long stem allow for the possibility of mucosal damage as well as an inadequate seal at the nares (nasal passages). Some manual aspirators have circumvented that problem by developing better nasal tips that have improved seal and safety.

Accordingly, there remains a need for improved devices and methods able to aspirate and irrigate simultaneously through a nozzle, with the nozzle providing an improved seal. A need remains for improved devices and methods able to provide a diagnostic function, and for both actions of aspiration and irrigation to be controlled by the operator with a single control (i.e., switch), so the devices and methods provide a faster and greater ease of use for both adults and children, including infants.

SUMMARY OF THE INVENTION

The invention provides improved devices and methods for providing irrigation and/or aspiration of a body including an opening, an orifice, a cavity, a lumen, a vessel, or a fold.

One aspect of the invention provides a hand-held test device. The device comprises a hand-held housing, the housing including a head and a base, the head and base being adapted to be releasably coupled to each other at an interface region, an aspirant reservoir within the housing, the aspirant reservoir adapted to contain aspirated fluid, pumping means within the housing adapted to draw fluid into the aspirant reservoir, and a diagnostic means within the housing for testing the aspirated fluid, the diagnostic means adapted to provide an indication of the results of testing the aspirated fluid.

In some embodiments, the device may further include a barrier means within the housing adapted to retain liquid in the aspirant reservoir and allow gas to pass out of the aspirant reservoir.

In one embodiment, the diagnostic means may comprise at least one of a test strip, an electrical chip, a chemical, and a genetic plate. The diagnostic means may be contained within the head and/or aspirant reservoir, and may be adapted to provide test results.

In some embodiments, the diagnostic means may include a sub-chamber within the aspirant reservoir, the sub-chamber adapted to deliver a predetermined volume of aspirated fluid to the diagnostic means. The sub-chamber may include a port in fluid communication with the aspirant reservoir that allows negative pressure of the device to control sub-chamber filling. A flexible portion may be included that is adapted to be pressed to facilitate at least one of sub-chamber filling and evacuation of the aspirated fluid to the diagnostic means. A flexible portion may also be included that is adapted to induce the addition of a diagnostic test reagent/primer into the sub-chamber to then be delivered to the diagnostic means.

In some embodiments, the diagnostic means accommodates microbiologic tests including influenza A and B, avian flu, RSV (respiratory syncytial virus), adenovirus, Legionella, CNV, EBV, Group A beta hemolytic *streptococcus, S. pneumoniae, N. meningitides, mycoplasma, Staphloccus aureus*, Malaria, HIV, rhinovirus, coccsackie virus, smallpox, anthrax, botulinum toxin, ricin, ebola, rabies, brucellosis, (plague) *yersinia pestis, coxeilla burnetti* (Q fever), T2 mycotoxins, *francisella tularensis* (tularemia), viral equine encephalitis, viral hemorrhagic fever, and *burkholdria mallei* (glanders).

In some embodiments, the diagnostic means accommodates toxicologic and/or chemical tests including amphetamines, cocaine, opiates, phencyclidine, tetrahydrocannabinol, acetaminophen, barbiturates, benzodiazepines, methadone, propoxyhenone, tricyclic antidepressants, calcium channel blockers, ethyl alcohol, ethylene glycol, ketones, glucose, hypoglaecemics, cytokines, interleukins, insulin, Hemoglobin A1C, electrolytes, human choreonic gonadotropin (pregnancy test), thyroid-stimulating hormone (TSH), T3 blood test, T4 blood test, c-reactive protein (CRP), and erythrocyte sedimentation rate (ESR).

In some embodiments, the diagnostic means accommodates real time polymerase chain reaction tests and/or immunoassays for viruses, bacteria, and cancers.

In some embodiments, the device further includes pumping means within the housing adapted to expel irrigation fluid from an irrigant reservoir, the irrigant reservoir adapted to contain irrigation fluid.

In some embodiments, the device may further include at least one nozzle extending from the housing, the nozzle including an irrigant lumen and an aspirant lumen, the irrigant lumen adapted to provide fluid communication between the irrigant reservoir and an irrigant port, the aspirant lumen adapted to provide fluid communication between the aspirant reservoir and an aspirant port.

In some embodiments, the interface region comprises at least one non-fluid flow component and at least one gas flow component, the interface region coupling the head to the base. The interface region may also comprise a seal between the head and the base, the seal adapted to allow a force exerted on the base to be transferred to the head, and the seal adapted to allow an aspiration pressure from the base to draw a gas out of the aspiration reservoir and into the base.

Another aspect of the invention provides a test device. The test device comprises a housing, an aspirant reservoir within the housing, the aspirant reservoir adapted to contain aspirated fluid, and a diagnostic means for testing the aspirated fluid, the diagnostic means adapted to provide an indication of the results of testing the aspirated fluid. Coupling means may be included to couple the device to a source of vacuum. Pumping means may be included for drawing fluid into the aspirant reservoir. The pumping means may draw the aspirated fluid into or onto the diagnostic means.

In some embodiments, the diagnostic means may be adapted to provide test results. The test results may comprise an indication on or in the housing.

Yet another aspect of the invention provides a method of diagnosing an aspirated substance. The method comprises the steps of providing a hand-held test device, the test device comprising a hand-held housing, the housing including a head and a base, the head and base adapted to be releasably coupled to each other at an interface region, an aspirant reservoir within the housing, the aspirant reservoir adapted to contain aspirated fluid, the aspirant reservoir in fluid communication with a nozzle in the head, pumping means within the housing adapted to draw fluid into the aspirant reservoir, control means adapted to operate the pumping means, and a diagnostic means within the housing for testing the aspirated fluid, the diagnostic means adapted to provide an indication of the results of testing the aspirated fluid.

The steps may further comprise positioning the nozzle on or in an orifice, using the control means to activate the pumping means to draw fluid from the orifice, through the nozzle, and into the aspirant reservoir, using the hand-held test device to provide a sample of the aspirated fluid to the diagnostic means, testing the aspirated fluid while the fluid remains in the housing, and providing an indication of the results of the testing.

In some embodiments, the method may further include an irrigant reservoir within the housing, the irrigant reservoir adapted to contain irrigation fluid, and using the control means to expel irrigation fluid from the irrigation reservoir, through the nozzle, and into the orifice.

In some embodiments, the interface region comprises at least one non-fluid flow component and at least one gas flow component, the interface region coupling the head to the base.

Yet an additional aspect of the invention provides a kit of devices to provide an irrigation and aspiration system. The kit comprises a head, an aspirant reservoir within the head, the aspirant reservoir adapted to contain aspirated fluid, at least one nozzle extending from the head, the nozzle including an aspirant lumen, the aspirant lumen adapted to provide fluid communication between the aspirant reservoir and an aspirant port, and a diagnostic means within the head for testing the aspirated fluid.

The kit may also include a body, the body adapted to releasibly couple to the head, the body including pumping means adapted to draw fluid into the aspirant port and through the aspirant lumen and into the aspirant reservoir, and control means to operate the pumping means adapted to draw aspirated fluid.

The kit may also include instructions for use describing the operation and use of the irrigation and aspiration system, the instructions comprising the operations of positioning the nozzle on or in an orifice, using the control means to activate the pumping means to draw fluid from the orifice, through the nozzle, and into the aspirant reservoir, using the hand-held test device to provide a sample of the aspirated fluid to the diagnostic means, testing the aspirated fluid while the fluid remains in the housing, and providing an indication of the results of the testing.

One aspect of the invention provides a device for delivery and/or removal of a fluid. The device comprises a housing, an irrigant reservoir within the housing, the irrigant reservoir adapted to contain irrigation fluid, and an aspirant reservoir within the housing, the aspirant reservoir adapted to contain aspirated fluid. A barrier means may be adapted to retain aspirated liquid in the aspirant reservoir and allow gas to pass out of the aspirant reservoir. At least one nozzle may extend from the housing, the nozzle including an irrigant lumen and an aspirant lumen, the irrigant lumen adapted to provide fluid communication between the irrigant reservoir and an irrigant port, the aspirant lumen adapted to provide fluid communication between the aspirant reservoir and an aspirant port. Pumping means may be adapted to expel irrigation fluid from the irrigant reservoir through the irrigant lumen and out the irrigant port. An interface region may be included, the interface region comprising at least one non-fluid flow component and at least one gas flow component.

Another aspect of the invention provides a hand-held device for delivery and removal of fluids. The hand-held device comprises a removable and replaceable head. The head comprises a housing, an irrigant reservoir within the housing, the irrigant reservoir adapted to contain irrigation fluid, an aspirant reservoir within the housing, the aspirant reservoir adapted to contain aspirated fluid, a barrier means adapted to retain aspirated liquid in the aspirant reservoir and allow gas to pass out of the aspirant reservoir, at least one nozzle extending from the housing, and a body, the body adapted to releasably couple to the housing, the body including pumping means adapted to draw fluid into the aspirant reservoir, and pumping means adapted to expel irrigation fluid from the irrigant reservoir, and an interface region, the interface region comprising at least one non-fluid flow component and at least one gas flow component, the interface region coupling the head to the body.

One aspect of the invention provides a system for irrigation and aspiration of a body orifice. The system may comprise a head, the head adapted to contain a predetermined amount of irrigation fluid in an irrigation reservoir, and the head containing an aspiration reservoir adapted to contain a predetermined amount of aspirated fluid, a body, the body releasably coupled to the head and containing pumping means to draw fluid into the aspiration reservoir, with the system defining a volume of about 200 cc to about 400 cc and sized and configured to be portable and operably held in a user's hand, and the system adapted to produce an incoming fluid volume of about 5,000 cc/min to about 20,000 cc/min.

In some embodiments, the system may be further adapted to produce an incoming fluid volume of about 5,000 cc/min to about 20,000 cc/min for a period of about one second to about 30 minutes.

In some embodiments, the system may be further adapted to produce an incoming fluid volume of about 5,000 cc/min to about 20,000 cc/min at a power consumption of about 5 watts to about 15 watts. A power source may comprise a capacity of about 100 mAh to about 1000 mAh.

One aspect of the invention provides a system for irrigation and/or aspiration of an orifice. The system comprises an irrigation function, an aspiration function, and user controls.

The irrigation function comprises an irrigation force and an irrigation reservoir, the irrigation reservoir adapted to contain an irrigation fluid, the irrigation force initiated by user input to the irrigation function, the irrigation force acting upon the irrigation reservoir to expel irrigation fluid from the irrigation reservoir and into the orifice.

The aspiration function comprises an aspiration pressure and an aspiration reservoir, the aspiration reservoir adapted to capture aspirated fluid, the aspiration reservoir adapted to retain aspirated liquid in the aspiration reservoir and allow gas to pass out of the aspiration reservoir.

The user controls may be adapted to provide a control function for at least one of the irrigation function and the aspiration function, the irrigation function being operational intermittently or simultaneously with the operation of the aspiration function.

The irrigation function may be operational with no interaction with the aspiration function, and the aspiration function being operational with no interaction with the irrigation function.

Other features and advantages of the inventions are set forth in the following specification and attached drawings.

BRIEF DESCRIPTION OF THE DRAWINGS

FIG. 9 is a side view of a variation of the irrigation and aspiration device in a user's hand.

FIG. 10A is a side view of a variation of the irrigation and aspiration device showing the head removed from the body of the device, and showing features of the invention that comprise at least a portion of an interface region.

FIG. 10B is a rear view of the head and a front view of the base, showing features of the seal and the head that comprise at least a portion of an interface region.

FIGS. 13A and 13B are rear and side views of variations of a head of the irrigation and aspiration device, and showing the head including barrier means including vanes and/or baffles.

FIG. 14 is a side view of a variation of a head of the irrigation and aspiration device, and showing the head including a flexible region to allow the head to be squeezed to expel irrigation fluid.

FIG. 21 is a side view of a variation of the head of the irrigation and aspiration device, showing various methods for filling the irrigation and aspiration device with irrigant.

FIGS. 22A through 22C are schematic views in partial cutaway showing variations of the head of the irrigation and aspiration device including alternative configurations for diagnostic means.

FIG. 23 is a perspective view with partial cutaway of a variation of the irrigation and aspiration device, showing a power source carried in the base of the device.

FIG. 24 is a perspective view of a variation of a power source recharger adapted to recharge the irrigation and aspiration device when the device incorporates a rechargeable power source.

FIG. 25 is a perspective view of a variation of the head of the irrigation and aspiration device, showing a variation of the controls adapted to provide user control of either or both the irrigation function and the aspiration function.

FIGS. 35A and 35B are schematic diagrams of variations of the irrigation and aspiration device in various configurations.

FIG. 42 illustrates a variation of a method of using a variation of the irrigation and aspiration device.

FIG. 43 is a schematic diagram of a variation of the irrigation and aspiration device with a remote component.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiments have been described in relation to use at the nostrils to provide relief within the nasal and sinus cavities, the details may be changed without departing from the invention, which is defined by the claims. Still, it should be appreciated that the devices and methods that embody features of the invention are also adaptable for use at any site or cavity where either or both irrigation and aspiration may be beneficial.

When referring to an irrigation and aspiration device that is manipulated by a physician or operator in order to irrigate and/or aspirate a site or cavity, the terms "proximal" and "distal" may be used to describe the relation or orientation of the device with respect to the operator as it is used. Therefore, the term "proximal" will be used to describe a relation or orientation of the device that, when in use, is positioned toward the operator (i.e., at the handle or base end of the device), and the term "distal" will be used to describe a position or orientation of the device that, when in use, is positioned away from the operator (i.e., at the other end of the device, such as the head and nozzle or catheter).

The terms aspiration and aspirant are used interchangeably herein when used as descriptors for elements (e.g., aspiration reservoir 40 and aspirant reservoir 40), and/or functionality. The terms irrigation and irrigant are used interchangeably herein when used as descriptors for elements, and/or functionality. The terms atomizing and atomization are used interchangeably herein when used as descriptors for elements and/or functionality.

Any elements described herein as singular can be pluralized (i.e., anything described as "one" can be more than one). Any species element of a genus element can have the characteristics or elements of any other species element of that genus. The described configurations, elements or complete assemblies and methods and their elements for carrying out the invention, and variations of aspects of the invention can be combined and modified with each other in any combination.

I. Nasal Cavity Anatomy

The devices and methods are particularly well suited for treating nasal and sinus congestion and associated symptoms due to a wide variety of possible causes. For this reason, the devices and methods will be described in this context. Still, it should be appreciated that the disclosed devices and methods are applicable for use in treating other symptoms elsewhere in the body, which are not necessarily nasal related.

Figure 1:
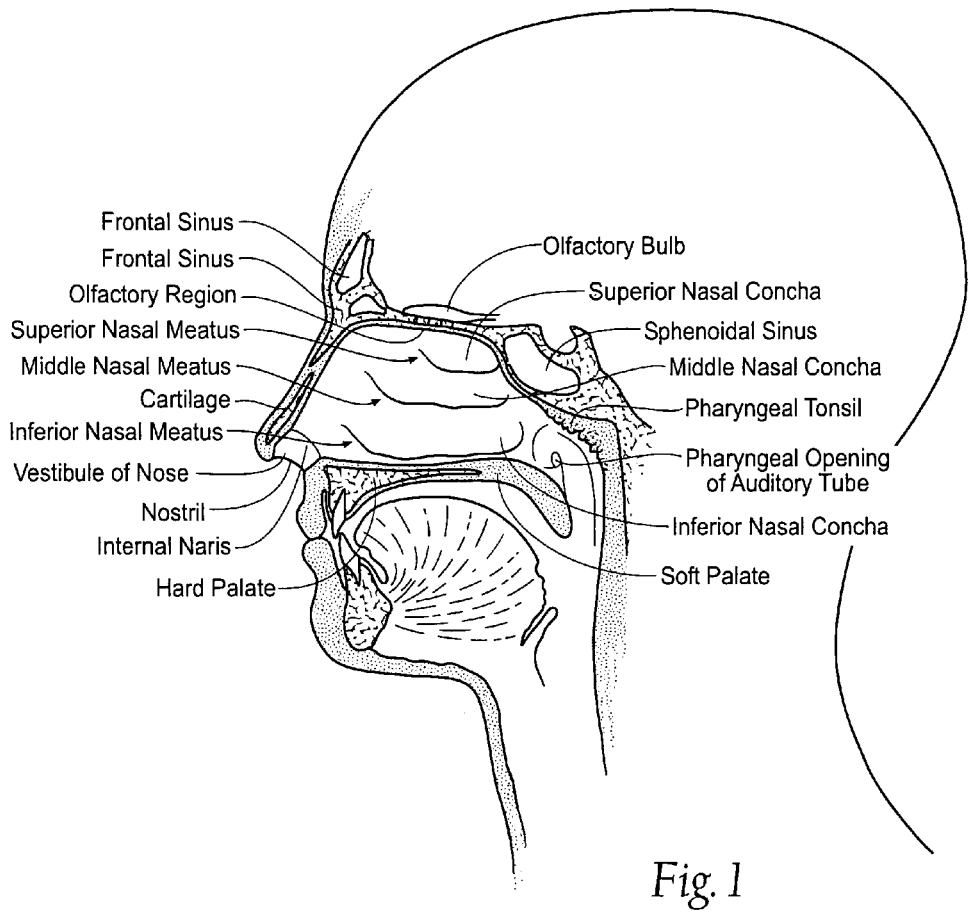
FIG. 1 is an anatomical lateral view in section of a head, and showing the nasal and sinus cavities.
Figure 2:
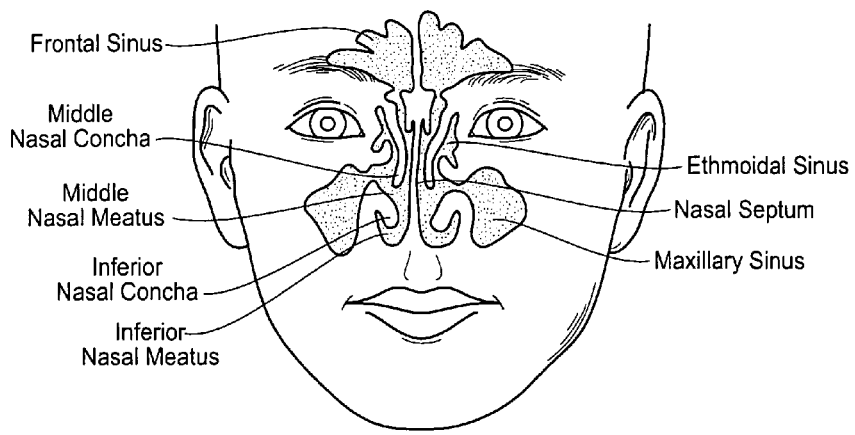
FIG. 2 is an anatomical anterior view of the face, and showing the four paranasal sinuses that communicate with the nasal cavity.

The nose functions in the respiratory system as the opening for the passage of air. As can be seen in FIGS. 1 and 2, bone support occurs in the upper half of the nose, whereas most of the lower half, including the wings of the nostrils, is cartilage. The partly bony and cartilaginous nasal septum divides the chambers of the nose into two nasal cavities. There are four paranasal sinuses that communicate with the nasal cavity: the maxillary, ethmoidal, frontal, and sphenoidal.

The area inside the nostril where nasal hair grows is called the vestibule. Farther inside the nasal cavity are the conchae. The nasal conchae are shelf-like protrusions on the walls of the nasal cavity. The mucous glands are found on the lowest of these—the inferior nasal concha. On the surface of the conchae are cilia that continuously undulate to move mucus toward the external naris. The uppermost part of the nasal cavity is the region where the olfactory organs are located.

The functions of the nasal cavity include cleaning, heating, and moistening the air that is breathed in. Inhaled air passes mainly through the middle nasal meatus (above the inferior nasal concha), where 60 to 70 percent of the dust is removed and the air is converted to a temperature of 25 to 35 degrees Celsius and a humidity of 35 to 80 percent.

Mucous membranes line the nasal cavity. The olfactory receptor cells are located in the superior nasal conchae, and many olfactory cilia are located in the surface mucous membrane. The minute particles that are the source of a smell dissolve in the mucus and stimulate the cilia, which transform them into electrical signals. The signals travel through the olfactory bulb, and reach the olfactory center of the cerebral neocortex, resulting in sensory perception of smell.

Because the paranasal sinuses are continuous with the nasal cavities through apertures that open into them, infection may spread from the nasal cavities, producing inflammation and swelling of the mucosa of the sinuses (sinusitis) and local pain. Sometimes several sinuses are inflamed (pansinusitis), and the swelling of the mucosa may block one or more openings of the sinuses into the naval cavities.

The presence of some mucus in the nose and throat is normal, but increased quantities can impede comfortable breathing and may be cleared by attempts at blowing the nose or expectorating phlegm from the throat.

In the case of bacterial infection, the bacterium becomes trapped in already clogged sinuses, breeding in the moist, nutrient-rich environment. Antibiotics may be used fruitfully to treat the secondary infection in these cases, but will generally not help with the original cause.

II. Irrigation and/or Aspiration Device Overview

Figure 3:
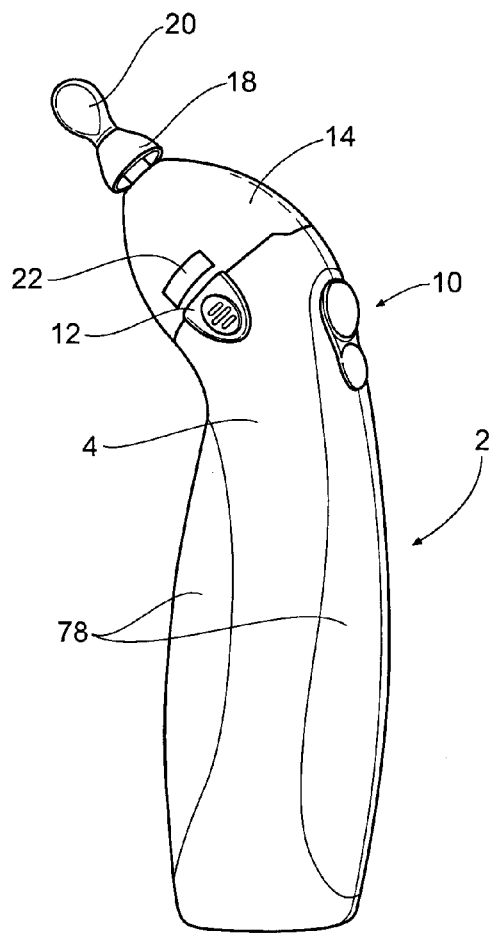
FIG. 3 is a perspective view of a variation of a device adapted for irrigation and aspiration.
Figure 4:
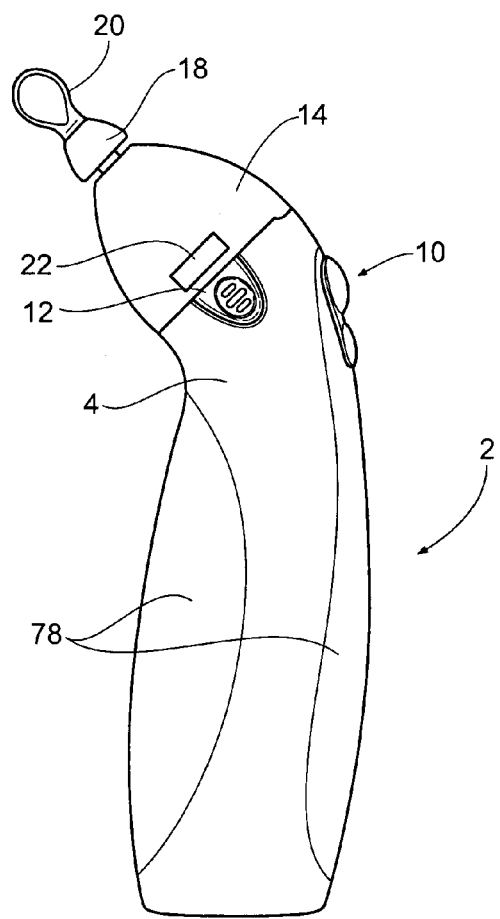
FIG. 4 is a side view of a variation of the irrigation and aspiration device shown in FIG. 3.

FIGS. 3 and 4 illustrate a cleaning device 2 or system for irrigation and/or aspiration of biological tissues or fluids. The device 2 can be used in or on a body orifice, including a cavity or lumen or vessel or fold, such as the vestibule of the nose, nasal cavity, the mouth and/or throat, the ear, the eye, a skin fold, the bellybutton, a wound, or combinations thereof. The device 2 can be inserted into a natural body orifice, including a cavity or lumen or vessel or fold, such as a nostril, the mouth—including access to the throat, esophagus, stomach, and lungs, ear canal, eye, naval, rectum, urethra, vagina, or adipose or fat fold, a wound, a surgical device (e.g., surgery port), or combinations thereof, all as non-limiting examples.

Figure 5A:
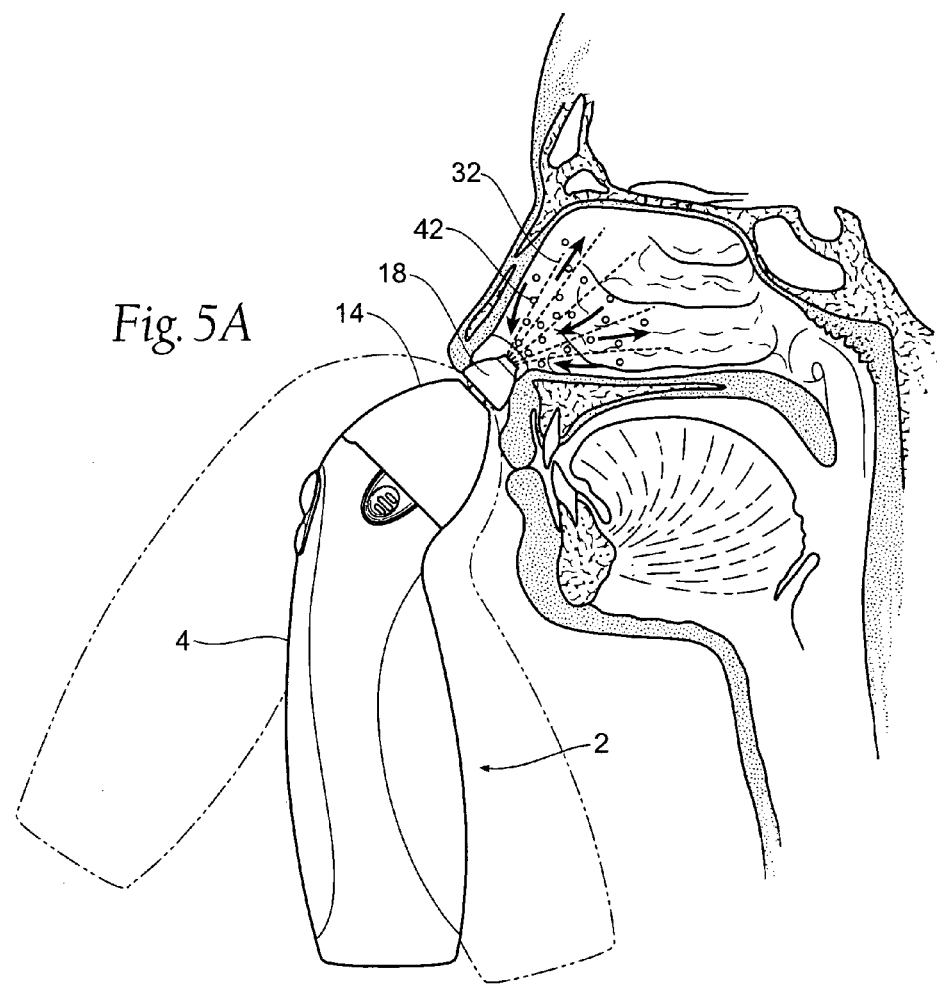
FIG. 5A is an anatomical lateral view in section of a head as shown in FIG. 1, and showing a variation of an irrigation and aspiration device as shown in FIG. 3 providing both irrigation and aspiration functions, and the ability of the device to articulate or flex while maintaining a seal with the nostril.

For example, the device 2 can be configured to perform nasal aspiration and/or nasal irrigation alone, interlaced, sequentially, or simultaneously, for example (see FIG. 5). Aspiration can include suctioning, i.e., the production of a vacuum or negative pressure via a pump and/or venturi effect, for example. The device 2 can be configured to irrigate and aspirate one at a time and/or concurrently. The device 2 can have an automatically driven vacuum and a manually actuated irrigation, both of which can operate simultaneously. The device 2 can have an automatically driven vacuum and an automatically actuated irrigation, both of which can operate simultaneously. The device 2 can have a manually driven vacuum and a manually actuated irrigation, both of which can operate simultaneously. The device 2 can have a manually driven vacuum and an automatically actuated irrigation, both of which can operate simultaneously. The device 2 may also be configured to separate the irrigation and aspiration functions, including separation of irrigation and aspiration fluids. Irrigation actuation may be controlled separately from aspiration actuation. Irrigant flow may be completely or partially separate from aspirant flow.

Figure 6:
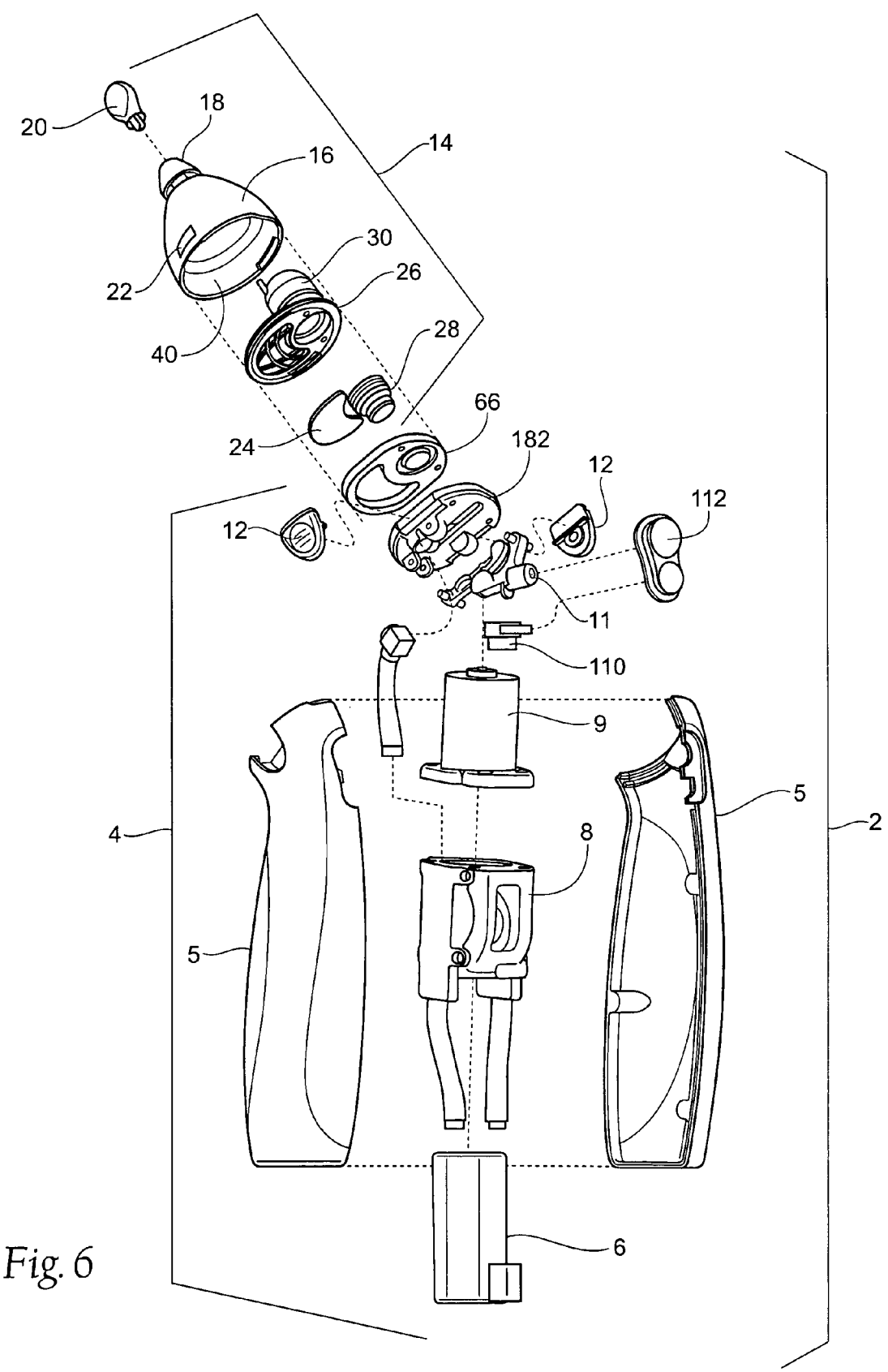
FIG. 6 is an exploded view of a variation of a device as shown in FIG. 3 adapted for irrigation and aspiration.

The device 2 comprises a variety of desirable technical features. As can be seen in FIG. 6, the device 2 may include a body 4 removably coupled to a head 14. Both the body 4 and head 14 may be single use, reusable, replaceable, and/or disposable. The body 4 and head 14 may be provided to the user as clean, but not sterile, or sterile. The body 4 comprises a case 5, and within and/or on the case is shown a power supply 6, a pump 8, a motor 9, and user controls 10. The pump 8 and/or motor 9 may be optimized to provide high sustained flow rates with low maximum vacuum pressures. The head 14 is shown including a shell 16, a flexible tip 18, a cap 20, diagnostic means 22, barrier means 24, an irrigant reservoir 30, and an aspirant reservoir 40. Combining the irrigant reservoir 30 and the aspirant reservoir 40 into a disposable and/or reusable head 14 helps to provide isolation of potentially contaminated fluids. The irrigation fluid 32 may be contained in the head 14 and may never enter the body 4, or may be contained in both the body 4 and head 14, or just in the body 4. The barrier 24 may prevent contaminated aspiration material 42 i.e., fluids, from entering the body 4. Each of the desirable technical features will be described in greater detail below.

The device 2 can be configured at full power to aspirate, for example, up to about 20,000 cc/min. (1,220 in$^3$/min.), or more narrowly 15,000 cc/min (915 in$^3$/min), or more narrowly 10,000 cc/min (610 in$^3$/min), or more narrowly 5,000 cc/min (305 in$^3$/min), or more or less, of air with no or minimal flow restriction for a time period of up to one second, or one minute, or one half hour, or one hour, or two hours, or more or less of continuous use, for example.

The device 2 can be configured at full power to produce aspiration suction with no or minimal flow restriction, for example, up to about 200 mm Hg (3.86 psi), or more narrowly about 120 mm Hg (2.32 psi), or more narrowly about 80 mm Hg (1.55 psi), or more narrowly about 50 mmHg (0.966 psi), or more or less, for a time period of up to one half hour, or one hour, or two hours, or more or less, of continuous use, for example. The device 2 may include a vacuum limiting valve 128 as a safety feature to limit the available vacuum to 100 mm Hg, for example.

The device 2 can be configured at full power for automatic irrigation to irrigate up to about 3 cc/min. (0.183 in$^3$/min.), or more narrowly about 1.5 cc/min. (0.092 in$^3$/min.), or more narrowly about 0.5 cc/min. (0.031 in$^3$/min.), or more or less, of irrigant 32 with no or minimal flow restriction.

The device 2 can be configured for manual irrigation to irrigate up to about 1.0 cc, or more narrowly 0.5 cc, or more narrowly 0.25 cc, or more or less, per depression, or activation, either direct or indirect, for example, e.g., per stroke of a piston or plunger or syringe or pump 11.

The device 2 can be configured at full power to use about 15 watts, or more narrowly about 10 watts, or more narrowly about 5 watts, or more or less. The amount of watts used generally depends on the amount of vacuum draw, i.e., the amount of restriction to the flow of air during aspiration.

The device 2 can be configured at full power to generate a noise level of about 40 db, or more narrowly about 30 db, or more narrowly about 20 db, or more or less. The amount of noise level generated generally depends on the amount of vacuum draw, i.e., the amount of restriction to the flow of air during aspiration.

The device 2 can be configured to be portable. For example, the device 2 can be unattached to any external devices (e.g., a wall or floor-mounted outlet or source for power, pressure, irrigant, or an aspirant reservoir). The device 2 can be configured to be connected to wall vacuum or a portable vacuum pump, for example.

The device 2 can be configured to be ergonomic and handheld. For example, the device 2 can weigh about 5.0 kg (11 lbs.), more narrowly about 2.0 kg (4.4 lbs.), more narrowly about 1.0 kg (2.2 lbs.), for example about 0.45 kg (1.0 lbs.), or more or less.

The device 2 can have a total maximum height, for example, of less than about 40 cm (16 in.), more narrowly less than about 30 cm (12 in.), yet more narrowly less than about 25 cm (10 in.), and may include a height about 21.5 cm (8.5 in.), or more or less. The device 2 can have a total maximum width, for example, of less than about 41 cm (16 in.), more narrowly less than about 30 cm (12 in.), yet more narrowly less than about 25 cm (10 in.), and may include a width about 5 cm (2 in.), or more or less. The device 2 can have a total maximum diameter, for example, of less than about 20 cm (8 in.), more narrowly less than about 15 cm (6 in.), yet more narrowly less than about 10 cm (4 in.), and may include a width about 9 cm (3.5 in.), or more or less.

The device 2 can have a total volume. For example, the device 2 can have a volume of about 400 cc (24.5 in$^3$), more narrowly about 300 cc (18.3 in$^3$), and more narrowly about 200 cc (12.2 in$^3$), or more or less.

The device 2 can be used to deliver fluids, for example, water, saline, therapeutic drugs, herbal medicines, vaccines, diagnostic agents, antiseptic agents, powders, and in any combination. The device 2 can be used to deliver fluids to any of the body cavity or body orifice regions described above.

III. System Kits

Figure 7A:
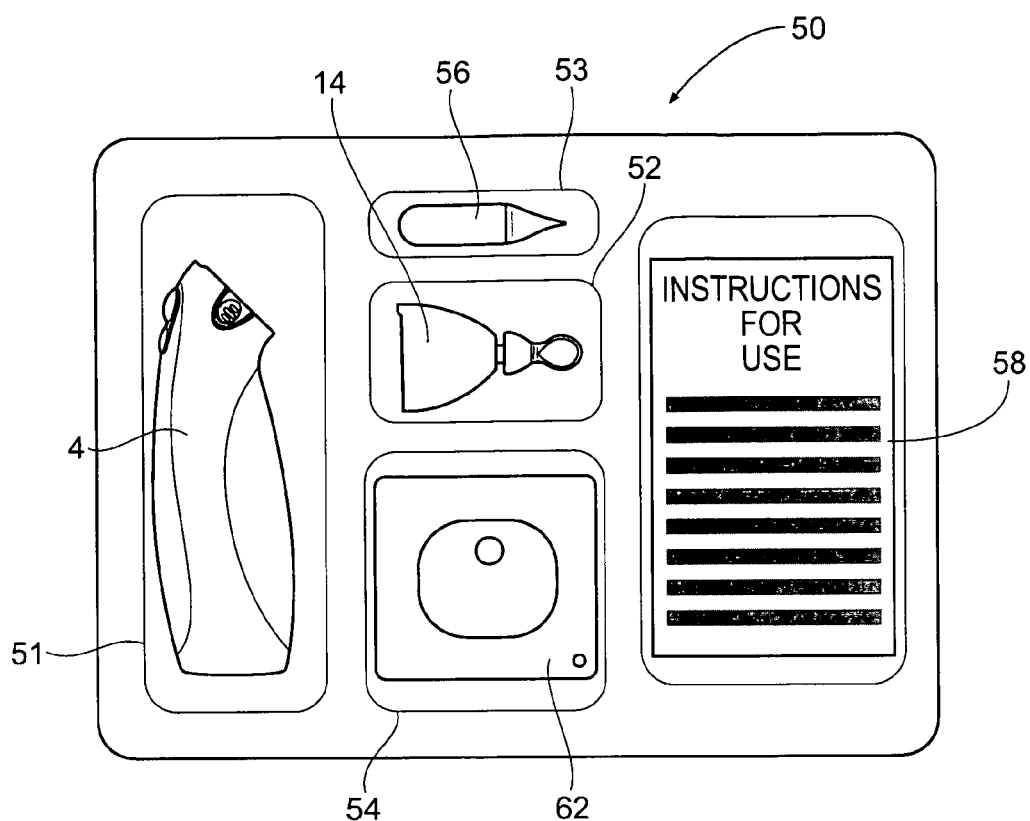
FIG. 7A is a plan view of a variation of a kit packaging the irrigation and aspiration device as shown in FIG. 3, along with instructions for use.

As FIG. 7A shows, the cleaning device 2 as just described can be consolidated for use in a multiple piece functional kit or kits 50. It is to be appreciated that the various components are not necessarily shown to scale.

The kit 50 can take various forms. In the illustrated embodiment, the kit 50 comprises an assemblage of individual packages 51, 52, 53, and 54. Each or one or more of the packages may comprise a clean or sterile, packaged or bagged assembly. One or more of the packages may include an interior tray or card made, e.g., from die cut cardboard, plastic sheet, or thermo-formed plastic material, for example, which hold the contents. The kit 50 also preferably includes instructions or directions 58 for using the contents of the packages to carry out a desired procedure. A procedure using the contents of the kit 50 shown in FIG. 7A will be described in greater detail later.

The instructions for use 58 can, of course vary. The instructions for use 58 can be physically present in one or more of the packages, but can also be supplied separately. The instructions for use 58 can be embodied in separate instruction manuals, or in video or audio recordings. The instructions for use 58 can also be available through an internet web page.

A. The Component Packages

The arrangement and contents of the packages can vary. For example, as shown in FIG. 7A, the kit 50 comprises the packages 51, 52, 53, and 54, and instructions 58. Two of these packages 51 and 52 provide the main components of the cleaning device 2 as described, with the body 4 in package 51 and the head 14 in package 52. The remaining packages 53 and 54 may or may not be included and provide ancillary component(s) used in connection with the device 2, e.g., a container 56 of irrigation fluid in package 53, and a recharger base 62 in package 54, and. In package 52, the head 14 of the device 2 may be preloaded with irrigation fluid 32.

Figure 7B:
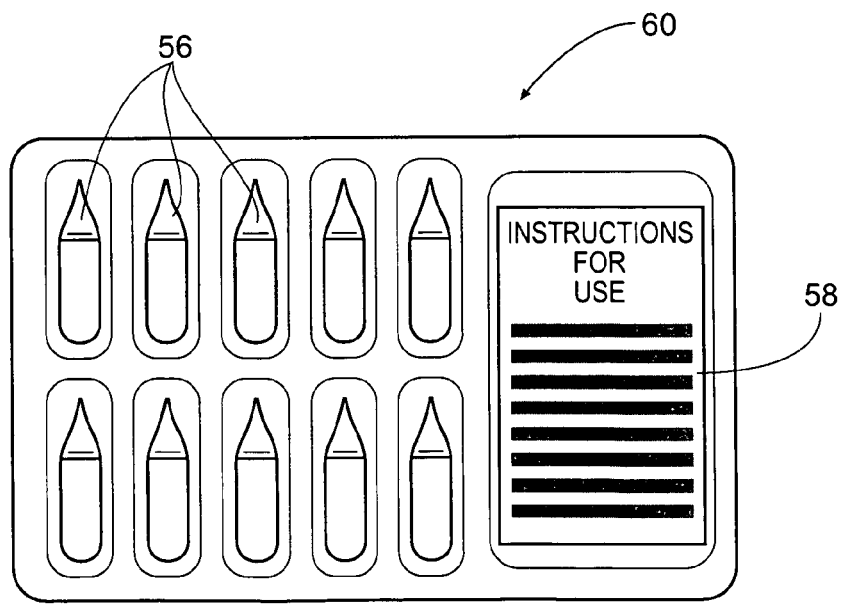
FIG. 7B is a plan view of an alternative kit similar to that shown in FIG. 7A, the alternative kit packaging extra irrigant, along with instructions for use.

The kit 60 (see FIG. 7B) may be included as a component of kit 50, or may be a stand-alone kit. The kit 60 may comprise a predetermined quantity of irrigant containers 56, for example the kit 60 is shown including 10 irrigant containers 56, although more or less may be included. Instructions for use 58 may also be provided to instruct the user on how to use the device 2 and/or the irrigant containers 56 to refill the irrigant reservoir 30 with irrigant 32. A supply of flexible tips 18 may also be provided in a kit.

It is to be appreciated that additional arrangements of kits are also possible. For example, a kit or kits may contain additional components directed to diagnostic devices adapted to test the fluids aspirated. In addition, a kit or kits may contain variations of the device 2, including non-rechargeable devices, non-battery powered devices, and/or manual devices, as non-limiting examples.

IV. Desirable Technical Features for Irrigation and Aspiration

The cleaning device 2 can incorporate various technical features to enhance its universality, including irrigation and aspiration functions.

A. Hand-Held Form

1. Body

According to one desirable technical feature, the device 2 can comprise a reusable and/or disposable ergonomic body 4 (e.g., handle), releasably coupled to a head 14, the device 2 adapted for use and ease of control by a user in one hand, either left or right.

As seen in FIG. 6, the body 4 can encase a rechargeable or non-rechargeable power source 6, such as a battery and/or a source of compressed gas. The body 4 may also be connected to an external power source, e.g., via a power cord (not shown). The body 4 can be configured to be connected to a source of vacuum, e.g., wall vacuum or a portable vacuum pump. The body 4 can have a fluid control system for irrigation and/or aspiration. The fluid control system can have one or more pumps 8 and 11. The fluid control system can have a driving motor 9. Either means for pumping 8 and/or 11 can be manually operated (e.g., squeeze, push, and/or trigger operated), or automatically operated (e.g., AC or DC electrically powered, compressed gas, stored energy, venturi port). Either pump 8 and/or 11 can be or have a syringe, a flexible or squeezable component, a piston pump, a blower, a turbine, a fan, a linear pump, a rotary vane pump, a centrifugal pump, a reciprocating pump, a diaphragm pump or combinations thereof, as non-limiting examples. The motor 9 can be part of a pump or a separate component.

The outer case 5 as well as internal portions of the body 4 can be made from a plastic, for example ABS, polycarbonate, or a combination thereof. The outer case 5 as well as internal portions of the body 4 can be made by injection molding, for example by injection molding halves and assembling. As can be seen in FIG. 6, the outer case 5 is shown comprising two halves, although it is to be appreciated that more or less pieces may be used.

Figure 8A:
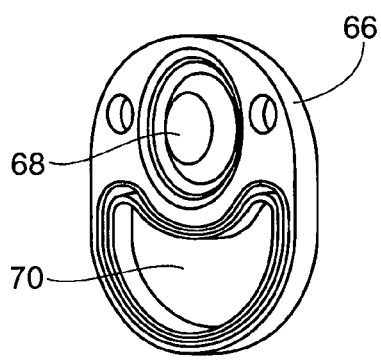
FIG. 8A is a perspective view of a variation of a seal that may be included between the head and the body of the irrigation and aspiration device.
Figure 8B:
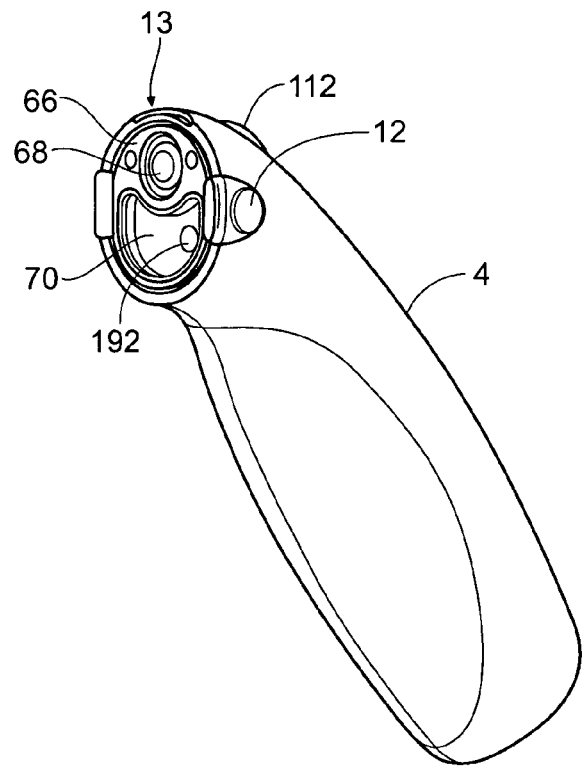
FIG. 8B is a perspective view of a variation of the irrigation and aspiration device, with the head removed from the body of the device, and showing the seal of FIG. 8A positioned on the body, and showing features of the invention that comprise at least a portion of an interface region.
Figure 8C:
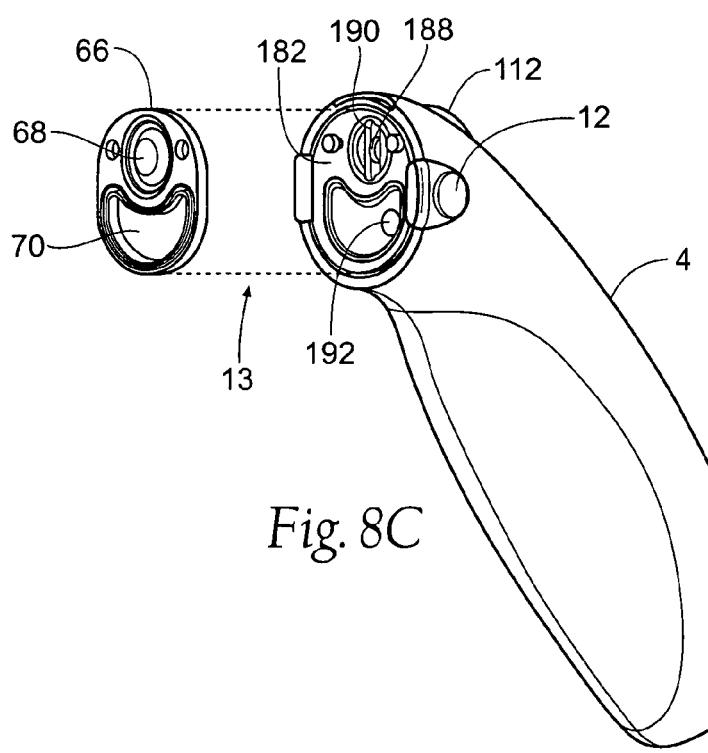
FIG. 8C is a perspective view similar to FIG. 8B, except with the seal and body shown in an exploded configuration, showing features of the invention that interact with the seal and comprise at least a portion of an interface region.

The body 4 (and/or head 14) can have an attachment ring or seal 66 on the inside or outside of the body 4 (and/or head 14). The seal 66 can be configured to provide a fluid tight coupling between the body 4 and the head 14, as a component of the interface region 13. As seen in FIGS. 8A through 8C, the seal 66 may include a bellows 68 and a passage 70. The bellows 68 provides a fluid tight seal between the pump 11 in the base and the irrigant reservoir 30 in the head 14. The passage 70 allows the flow of fluid, i.e., air, from the aspirant reservoir 40, through the barrier 24, and to the pump 8 in the base 4. The seal 66 may be adapted to provide separation of the irrigation and aspiration systems and functions. The seal 66 may be adapted to allow an irrigation force exerted on the base 4 to be transferred to the head, and the seal may be adapted to allow an aspiration pressure from the base 4 to draw gas out of the aspiration reservoir 40 and into the base 4.

As seen in FIG. 8C, a component 188 of the pump 11 may be configured to apply a direct or indirect force to the bellows 68. This force may then be translated to the head 14 to eject irrigant from the irrigant reservoir 30.

As can be seen in FIG. 9, the body 4 can be configured to be ergonomically held in one hand. The body 4 can have contours to fit the palm 74 and fingers 76 when grasped. The body 4 may include grip pads 78. The grip pads 78 may comprise soft rubber, metal, soft plastic, or other known materials, and may be attached and/or integral with the body 4. The grip pads 78 may be smooth, and they may have ridges or texturing, or combinations thereof. The grip pads 78 can be ergonomically located about the body 4, and the pads 78 can be configured to be located at all or some of the locations where the user (e.g., the user's palm) naturally applies pressure to the body 4 during use.

The body 4 (and/or head 14) can have various colors, and may be transparent, translucent, and/or opaque materials. The body 4 (and/or head 14) may also incorporate forms of indication such as lights, for example, for operational purposes and/or for entertainment of the user and/or patient. The body 4 (and/or head 14) may incorporate a "key" or fitment element 15 for required registration of the head 14 to the body 4. Connectors 12 (described below) may provide this feature. The body 4 may communicate with the head 14, and the head 14 may communicate with the body 4, e.g., electrical communication between the body 4 and the head 14, for diagnostic, status, or indication purposes, for example.

Any oscillations or vibrations of the device 2 (e.g., due to moving parts such as pumps, motors, reciprocating solenoids, piezoelectric transducers) can be dampened. Moving parts can be mounted to the body 4 or head 14 using dampers, such as soft rubber washers. Excessive pressure and pump exhausts can be muffled, for example using a restricting plate in an exhaust conduit 166. The walls of the device 2 (e.g., case 5 and shell 16) can be thickened and made from layered and/or laminated materials. The walls of the device 2 can be otherwise sound-proofed. Moving parts in the device 2 can be dynamically balanced, for example such that all support forces sum to zero at any given instant and/or the device 2 can have active noise cancellation. Motors (e.g., in or coupled to a pump) can have counterbalances. Multiple motors can be configured to oppose dynamic forces.

With a filled irrigant reservoir 30 and/or aspirant reservoir 40 and in-body power source 6 (as described below), the device 2 can weigh about 5.0 kg (11 lbs.), more narrowly about 2.0 kg (4.4 lbs.), more narrowly about 1.0 kg (2.2 lbs.), for example about 0.45 kg (1.0 lbs.), or more or less. The irrigant 30 and/or aspirant reservoirs 40 can be translucent and/or transparent, for example to allow a user to identify when to replace/refill irrigant 32 and/or empty aspirant 42, and/or to check cleanliness and/or operation of the device 2.

2. Head

According to one desirable technical feature, the head 14 can be removably attached (see FIGS. 10A and 10B) or integral with the body 4. The head 14 can be positioned at varying angles relative to the body 4, and may be adapted to articulate and/or flex and/or pivot freely relative to the body 4. The connections of the head 14 to the body 4 can be compliant and flexible so as the head 14 can pivot and translate from the perimeter of the head 14 (this is stated for exemplary purposes only, there are multiple mechanical solutions). The head 14 can be removably attached to the body 4 with a (one or more) connector(s) 12. The head 14 may be pressed onto the body 4 until the connectors 12 click the head 14 into place. The connector 12 can be a screw, snap, press fit connector, or combinations thereof, as non-limiting examples.

The irrigation and/or aspiration systems, methods, and functions may have or include an interface region 13 between and/or including portions of the body 4 and the head 14. The interface region may directly or indirectly connect a pump to a reservoir and/or a vacuum pressure to a reservoir, for example. The interface region 13 may be adapted to provide separation of the irrigation and aspiration systems, methods, and functions.

The interface region 13 can, for example, include a non-fluid flow region or component(s), such as the irrigant plug 28 and/or the bellows 68 and/or the irrigation aperture 190, where a force 180 may be transferred, and the interface region 13 can, for example, include a gas flow region or component(s), such as the passage 70 and/or the aspiration aperture 192, where a gas may be transferred. The interface region 13 can, for example, enable the head 14 to be removed from the body 4, to allow the irrigant reservoir 30 and aspirant reservoir 40 to be contained within the head 14, so as to eliminate potential contamination of the body 4 with any contaminated fluids. Part(s) of the irrigation and/or aspiration functions may be removed with the head 14, and remaining portions of the irrigation and/or aspiration functions may remain attached to or integral with the body 4, as will be described later. The interface region 13 may also enable rotation and translation between the head 14 and the body 4.

Figure 11A:
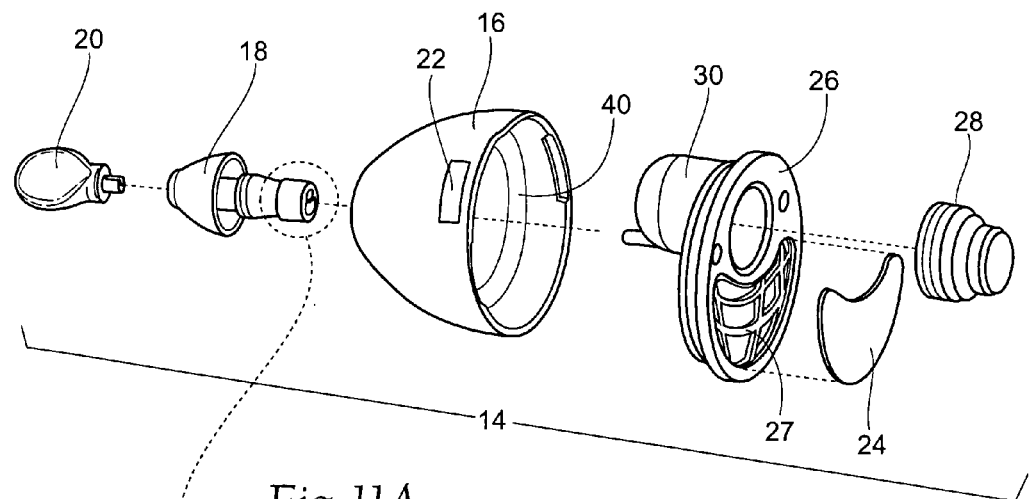
FIG. 11A is an exploded view of a variation of the head of the irrigation and aspiration device, and showing the head comprising both an irrigation reservoir and an aspiration reservoir.
Figure 11B:
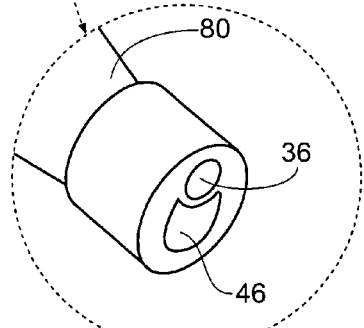
FIG. 11B is a close-up view of a proximal portion of the flexible tip, and showing an irrigation channel and an aspiration channel.
Figure 12:
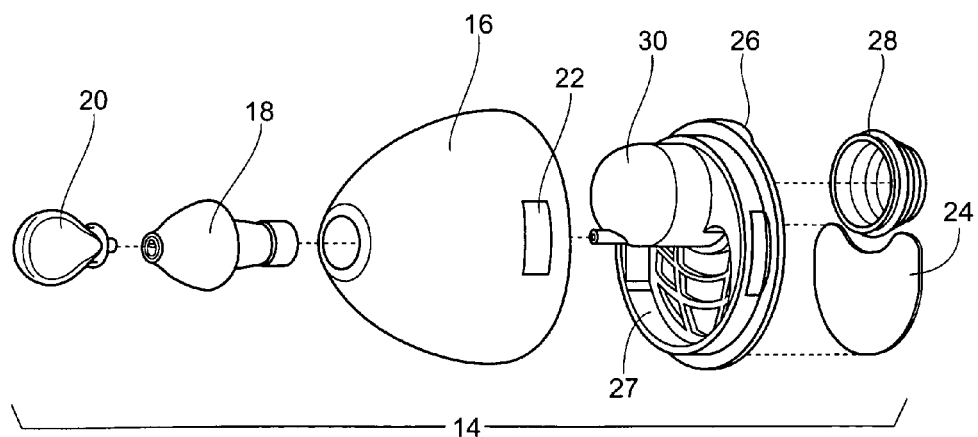
FIG. 12 is an additional exploded view of a variation of the head of the irrigation and aspiration device, as shown in FIG. 11A.

As can be seen in FIGS. 11A through 12, the head 14 may comprise a shell 16 and a back 26. A flexible nozzle or catheter or tip 18 may protrude distally from the shell 16, and may include a cap 20 to be positioned on or in or over the flexible tip 18 when the device 2 is not in use, and/or for diagnostic purposes. The cap 20 may include a breakable seal out of the package, and with the first use, the seal is broken. The cap 20 may then be repositioned on or in the flexible tip 18. The irrigant reservoir 30 and the aspiration reservoir 40 are shown within the shell 16, and may both be in fluid communication with the flexible tip 18.

In some embodiments, barrier means 24 may be positioned in the head 14 and/or the body 4. In some embodiments, barrier means 24 may be positioned adjacent or within a recess 27 in the back 26. For example, the barrier 24 may comprise a filter, such as a hydrophobic filter, a foam, a sponge, or other materials, such as cotton in the form of a ball or other desirable shapes, or any combination.

The barrier means 24 may have a shape adapted for optimal use within the head 14 and back 26. A shape, such as a kidney shape, provides efficient use of surface area within the head 14, and thus decreases the amount of resistance the barrier means provides, although other linear and non-linear shapes are possible, such as round, square, triangle, deformable, baffled, or random, for example. In some embodiments, the barrier means 24 may comprise a 10 micron filter, more narrowly an 8 micron filter, and more narrowly about a 5 micron filter, or more or less. The barrier means 24 may be configured to allow a gas (i.e., air) to pass out of the aspirant reservoir 40, while not allowing a liquid (i.e., aspirant fluids 42) to pass out of the aspirant reservoir. The barrier means maintains a separation of aspiration fluids 42 between the disposable head 14 and the body 4.

In some embodiments, the barrier means 24 may include or comprise vanes and/or baffles and/or corridors within the head 14 or body 4 to increase resistance of aspirated fluid 42 from entering the body 14 (see FIGS. 13A and 13B). The vanes and/or baffles and/or corridors may also be in combination with any of the materials as previously described.

An irrigant plug 28 may be positioned adjacent or within the back 26 and/or irrigant reservoir 30. As previously described, the head 14 (and/or body 4) can include a seal 66 to provide a fluid tight coupling between the body 4 and the head 14. The bellows 68 within the seal 66 interacts with the plug 28 to allow the pump 11 in the base 4 to provide a pressure 180 to the irrigant reservoir 30 to expel or eject the irrigant fluid 32.

Just as with the body 4, components of the head 14 described above can be opaque, transparent and/or translucent, and may also have various colors.

In some embodiments, irrigant 32 may be ejected in various ways. For example, in some embodiments, irrigant 32 may be ejected using a rack-and-pinion configuration, providing a mechanical advantage. In other embodiments, irrigant 32 may be ejected using a direct linkage. And in other embodiments, portions of the head 14 may include one or more deformable or flexible sections 72 to allow the user to squeeze the irrigation reservoir 30 to expel irrigant 32 (see FIG. 14). The user may use a finger or thumb 77, as shown, to apply a pressure to the flexible section 72 to produce a desired irrigation pressure.

In some embodiments, when the irrigant reservoir 30 is empty and/or the aspirant reservoir 40 is full or otherwise in need of emptying or cleaning, the entire head 14 can be removed from the body 4 and replaced with a new head 14 containing more irrigant 32 in the irrigant reservoir 30.

Figure 15A:
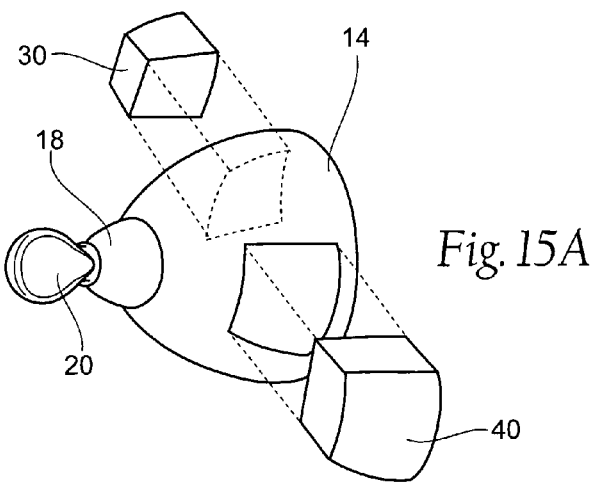
FIG. 15A is a perspective view of a variation of a head of the irrigation and aspiration device, and showing the head comprising removable or replaceable, or reusable or disposable irrigation and/or aspiration reservoirs.

FIGS. 15A through 15D illustrate alternative embodiments of the head 14. FIG. 15A shows an embodiment where the head 14 includes an irrigation reservoir cartridge 30 and/or an aspiration cartridge 40 configured to removably attach to the head 14. The head 14 and/or irrigation reservoir cartridge 30 and/or aspiration cartridge 40 can have ports, hooks, latches, pegs, or combinations thereof that can removably attach to the same on the head or cartridges. When the irrigant cartridge 30 is not attached, the cartridge receptacle can define a void substantially equivalent to the configuration of the irrigant cartridge 30.

The irrigant reservoir cartridge 30 can have one or more ports (not shown) that can engage the head 14. The ports on the irrigant reservoir cartridge 30 can be closed or covered, for example by adhered aluminum foil when the irrigant cartridge 30 is not in the head 14. For example, the head 14 can have one or more fangs or tubes configured to pierce the irrigant reservoir cartridge 30 (e.g., through a foil or seal) and be in fluid communication with the interior of the irrigant reservoir cartridge 30 and pressurize or depressurize the irrigant reservoir cartridge 30 and/or withdraw irrigant from the irrigant reservoir cartridge 30.

A first irrigant reservoir cartridge 30 can be removed from the head 14 and replaced with a second irrigant reservoir cartridge 30, for example when the first irrigant reservoir cartridge 30 is empty.

Figure 15B:
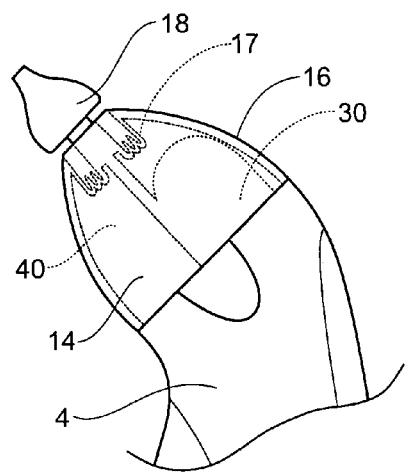
FIG. 15B is a side view in partial phantom showing an alternative variation of a head of the irrigation and aspiration device, and showing a flexible tip integral with the head and/or shell of the head.

FIG. 15B shows an embodiment of the head 14 where the flexible tip 18 may be integral with the head 14 and/or the shell 16 of the head. A flexible region 17 as part of the shell may couple to the tip 18, allowing the tip 18 to flex.

Figure 15C:
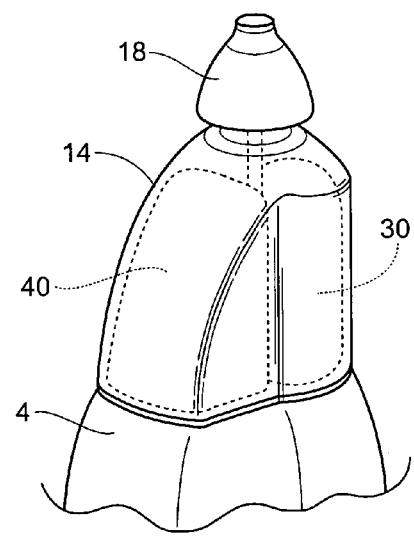
FIG. 15C is a perspective view of an alternative variation of a head of the irrigation and aspiration device, and showing the head comprising an alternative shape and configuration and being removable or replaceable, or reusable or disposable with irrigation and/or aspiration reservoirs.

FIG. 15C shows an embodiment of the head 14 where the head includes an irrigation reservoir 30 and an aspiration reservoir 40 side by side. The head comprises a form factor more similar to a cartridge configuration.

Figure 15D:
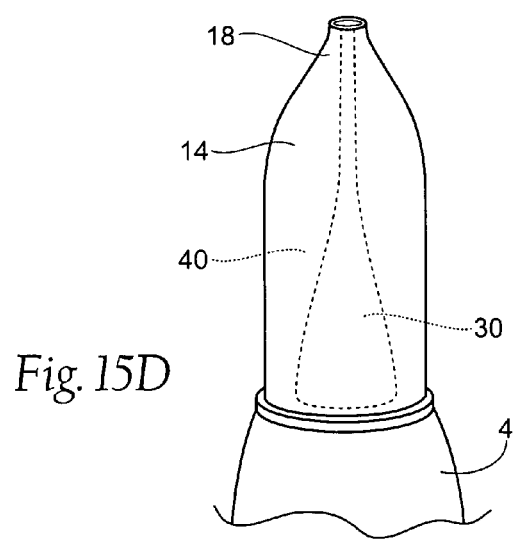
FIG. 15D is a perspective view of an alternative variation of a head of the irrigation and aspiration device, and showing the head comprising an alternative shape and configuration, including a combined head and flexible tip configuration, and being removable or replaceable, or reusable or disposable with irrigation and/or aspiration reservoirs.

FIG. 15D shows an embodiment of the head 14 where the head includes an irrigation reservoir 30 positioned within an aspiration reservoir 40. The head 14 comprises a form factor including a unitary head 14 and flexible tip 18.

The irrigant reservoir 30 and/or the aspirant reservoir 40 can be removed for cleaning or replacement, such as in the form of the cartridge, for example, as described above. The aspirant reservoir 40 may be removed, and may also be sealed, for diagnostic purposes, as will be described in greater detail later. Access to the aspirant reservoir or cartridge 40 may be provided to allow access to the aspirant fluid 42 for testing.

The head 14 and/or irrigant reservoir 30 and/or aspirant reservoir 40 and/or the device 2 can be washed, for example, by hand and/or in a dishwasher. The body 4 and/or the device 2 can be waterproof.

The head 14 and/or irrigant 30 and/or aspirant reservoirs 40 can be cleanable, for example dishwasher safe (e.g., the ability to withstand about 15 minutes at least at about 50 degrees Celsius, or more narrowly at least about 75 degrees Celsius, or more or less, without substantially noticeable deformation, deterioration, or other damage, and lack of substantial deterioration or other substantial damage from similarly extended exposure to water and typical dishwasher detergents).

a. Flexible Tip

The flexible tip 18 (i.e., nozzle or catheter) may be integral with the head 14, or may be a separate removable and/or replaceable and/or disposable component, as shown. The flexible tip 18 is desirably sized and configured to be placed adjacent to, or inserted wholly or partially into, a biological orifice or surface to be irrigated and/or aspirated. For example, the flexible tip 18 can be configured to fit wholly or partially into a nostril (see FIG. 5A), and its flexibility allows for movements of the device 2 and/or movements of the patient. The flexible tip 18 can have a pointed conical, rounded conical, nippled, bulbous, mushroom cap, or waisted configuration, or combinations thereof. The flexible tip 18 may include a flexible stem 80, and/or sealing means, such as an o-ring 86 as shown.

Figure 16:
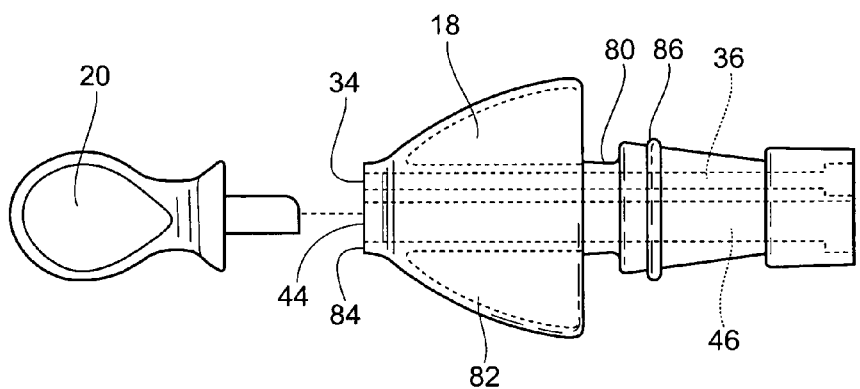
FIG. 16 is a side view of a variation of the flexible tip, with the cap removed.

In an exemplary embodiment, FIG. 16 illustrates that the distal portion of the flexible tip 18 can be configured to include a bulbous or mushroom capped shape portion 82. The distal portion of the flexible tip 18 can be bulged or waisted. The flexible tip 18 can have a larger radius proximal to the distal end 84, for example, to prevent over-insertion of the tip 18 into a natural body orifice.

Figure 5B:
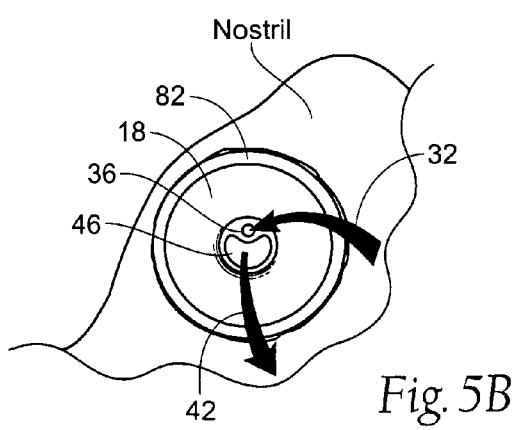
FIG. 5B is a close-up anatomical inferior view of a variation of the flexible tip of the device providing the seal with the nostril, and irrigation and aspiration channels extending through the flexible tip and into the nasal cavity, providing the ability to irrigate and aspirate simultaneously.

The tip 18 can be configured to make a positive seal with the irrigation and/or aspiration site (e.g., the nostril), as seen in FIG. 5B. The distal flexible portion 82 provides the temporary seal with the nostril, allowing for both irrigation (identified with arrow 32) and aspiration (identified with arrow 42) to take place through the respective irrigation channel 36 and aspiration channel 46.

The tip 18 can seal to the irrigation and/or aspiration site analogous to a ball and socket joint and/or similar to nested tubes. The flexible tip 18 can be rotationally symmetric about a longitudinal axis of the head 14. The rotational alignment can be decoupled from the sealing functionality, for example allowing one more degree of freedom for the user.

The flexible tip 18, and/or all or some of the head 14 can be made from and/or covered or coated with a compliant material such as silicone rubber or foam, and/or medications, and/or lubrications. The flexible tip 18, and/or all or some of the head 14, i.e., components that may touch the patient, may be removable and/or replaceable and/or disposable. The flexible tip 18 can be compliant, for example, to permit sealing to differently-shaped nostrils, and may include lubrications to enhance sealing. The flexible tip 18 can be sufficiently rigid to not deform against the negative pressure of the aspiration.

Figure 17:
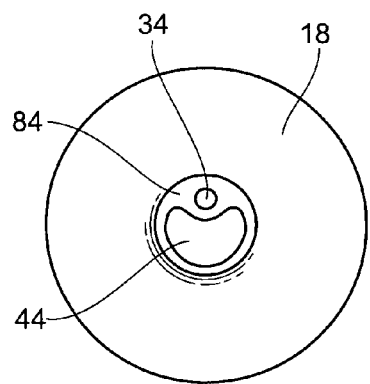
FIG. 17 is a front view of a variation of the flexible tip, as shown in FIG. 16.
Figure 18:
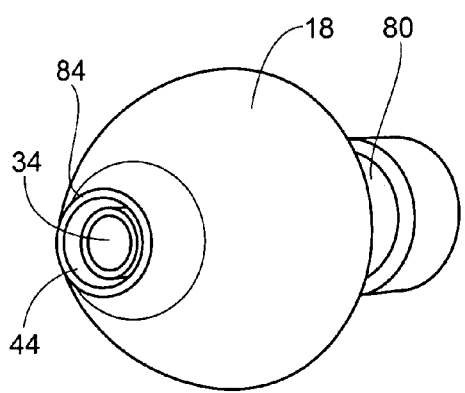
FIG. 18 is a perspective view of a variation of the flexible tip, showing the flexible tip with recessed and eccentric irrigation and aspiration ports.

FIGS. 17 and 18 illustrate the flexible tip 18 includes a distal end or face 84 for the passage of fluids (e.g., for either or both irrigation and aspiration). The distal face 84 is shown to comprise both an irrigation port 34 and an aspiration port 44. It is to be appreciated that the aspiration port 44 and the irrigation port 34 can be at the outer surface of the flexible tip 18 and/or the aspiration port 44 and/or the irrigation port 34 can be recessed within the flexible tip 18. It is also to be appreciated that, in an alternative embodiment, the flexible tip 18 can have one or more irrigation ports 34 and/or aspiration ports 44.

As shown, the irrigation port 34 can be located adjacent to the aspiration port 44 (see FIG. 17). The irrigation port 34 can be completely or partially surrounded by the aspiration port 44 (see FIG. 18). The aspiration port 44 can be completely or partially surrounded by the irrigation port 34.

b. Irrigation and Irrigant Reservoir

Figure 19:
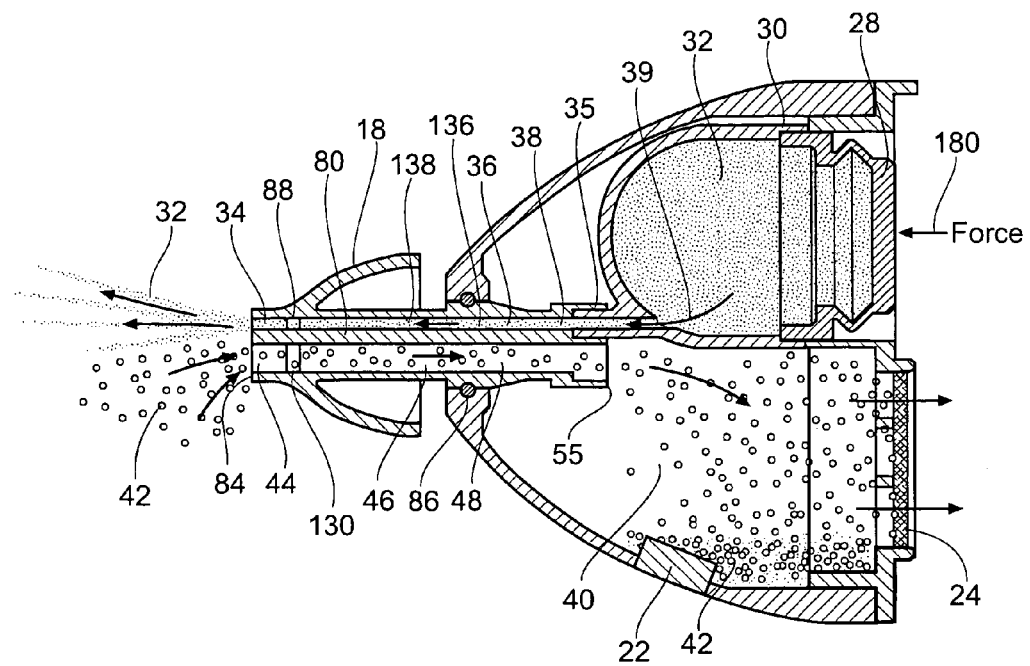
FIG. 19 is a side view in section of a variation of the head of the irrigation and aspiration device, and showing the head including both an irrigation reservoir and an aspiration reservoir, and irrigation and aspiration flow channels, the configuration adapted to provide complete isolation of irrigation and aspiration fluids while allowing simultaneous irrigation and aspiration out of a single tip or nozzle.
Figure 20:
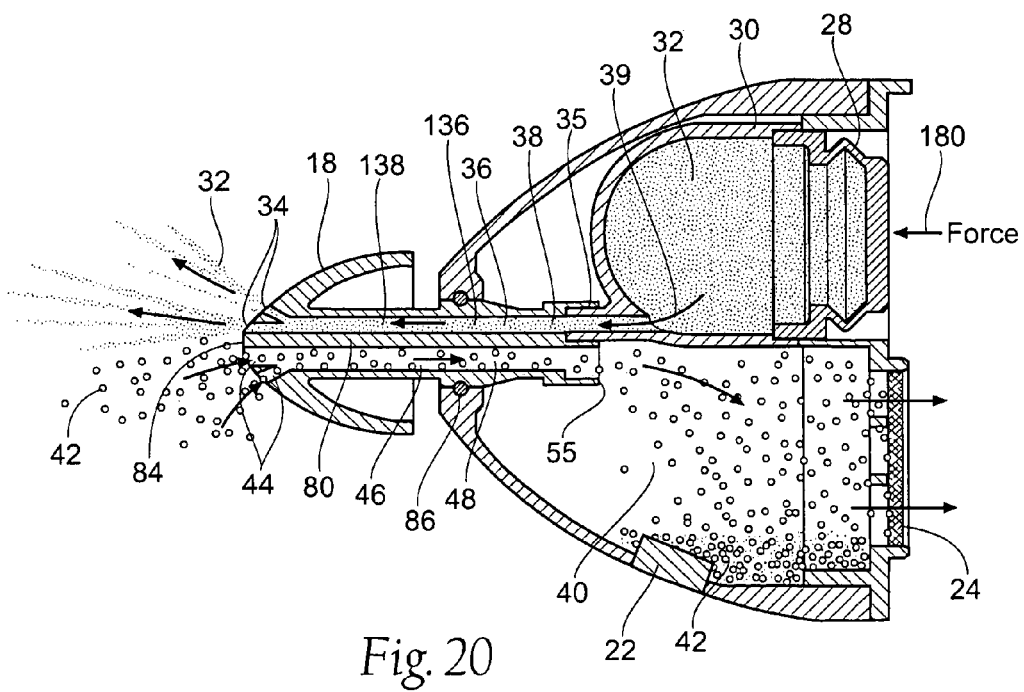
FIG. 20 is a side view in section of a variation of the head of the irrigation and aspiration device as shown in FIG. 19, and showing the flexible tip including multiple irrigation and aspiration ports.

As seen in FIG. 19, the irrigant reservoir 30 is shown to be in direct fluid communication with the irrigant port 34, via the irrigation channel 36. In an alternative embodiment, the head 14 can have one or more irrigation ports 34 (see FIG. 20). The irrigation port 34 can be configured to dispense or otherwise discharge the irrigation fluid 32. The irrigation port 34 can be configured to dispense or otherwise discharge the irrigation fluid in an atomized configuration, for example, by mixing the irrigation fluid 32 (e.g., in a liquid state) with an atomizing gas, and/or passing irrigation fluid 32 through an atomizer 88. The irrigation fluid 32 may be heated (e.g., electrically heated via the power source 6) to provide an irrigation fluid 32 at or near the body temperature to provide additional comfort for the patient.

The flexible tip 18 is shown to include the flexible stem 80. The stem 80 (and flexible tip 18) may comprise the irrigation channel 36. The irrigation channel 36 may also be a component of the irrigant reservoir 30, or a separate component, or any combination. The stem 80 of the flexible tip may be positioned in fluid communication with the irrigant reservoir 30 via an irrigant reservoir port 35.

The irrigation channel 36 can have an irrigation channel diameter 38. The irrigation channel diameter 38 can be the minimum internal diameter of the irrigation channel 36. The irrigation channel diameter 38 can be less than about 1 cm (0.4 in.), more narrowly less than about 2 mm (0.8 in.), for example about 0.7 mm (0.03 in.), or more or less.

The irrigation channel 36 can have an irrigation channel lining 136. The irrigation channel lining 136 can actively (e.g., can be movable, such as an electro-active polymer skin) or passively (e.g., by the shape of the channel lining 136) focus the exiting stream of irrigant 32. The irrigation channel lining 136 can form a venturi 138 in the irrigation channel 36. The irrigation channel lining 136 can be integral with, or fixedly or removably attached to the irrigation channel 36.

In use, a force may be applied, such as via pump 11 and user controls 10 (to be described in greater detail below) to the flexible irrigation plug 28 adjacent to and/or coupled to the irrigant reservoir 30. The force produces an irrigant pressure 39, causing irrigant 32 to flow through the irrigation channel 36, out the irrigation port 34, and into the desired cavity.

The irrigant reservoir 30 may comprise a variety of shapes and can be integral or fixedly or removably attached to the head 14 and/or the body 4. The irrigant reservoir 30 can hold irrigant 32. The irrigant reservoir 30 can be a replaceable cartridge or ampoule. The irrigant reservoir 30 may comprise a compressed gas and irrigant 32. The irrigant reservoir 30 can be removable, disposable, replaceable, recyclable, or combinations thereof. The irrigant reservoir 30 can be pre-filled with irrigant 32 or ready for adding all or a component (e.g., water) of the irrigant 32. The irrigant reservoir 30 can be divided into multiple sub-reservoirs. For example, one sub-reservoir can have salt and another irrigant reservoir can have water. The sub-reservoir contents can mix (e.g., creating saline solution) when the irrigant is dispensed.

The irrigant reservoir 30 can be the same volume, a larger volume than, or a smaller volume than the aspirant reservoir 40. For example, the aspirant reservoir 40 volume can be about 100 or less times larger than the irrigant reservoir 30 volume, or more narrowly, about 20 or less times larger than the irrigant reservoir 30 volume, or more narrowly, about 7 or less times larger than the irrigant reservoir 30 volume, or more narrowly, about 3 or less times larger than the irrigant reservoir 30 volume, or more narrowly about 1.5 or less times larger than the irrigant reservoir 30 volume, for example the aspirant reservoir 40 volume can be about 1.25 times the irrigant reservoir 30 volume. The irrigant reservoir 30 volume can be, for example, about 10 mL, or more narrowly about 5 mL, or more narrowly about 3 mL, or more or less.

The irrigant reservoir 30 can be a first color (e.g., blue), the aspirant reservoir 40 can be the first color or a second color (e.g., yellow or red). The irrigant reservoir 30 and/or aspirant reservoir 40 can be transparent, translucent or opaque. The irrigant reservoir 30 can seat into the head 14 in a different configuration than the aspirant reservoir 40. For example, the irrigant reservoir 30, aspirant reservoir 40, and the remainder of the head 14 can be configured so as to not be able to insert the irrigant reservoir 30 in the head 14 in place of the aspirant reservoir 30 and/or vice versa.

The irrigation fluid or irrigant 32 can have or be water, saline solution, zinc solution (e.g., zinc sulfate solution), alcohol, anesthetic agent, analgesic agent, antipyretic agent, anti-inflammatory agent such as a non-steroidal anti-inflammatory agent (e.g., ibuprofen, aspirin, salicylic acid, COX02 inhibitor, COX-3 inhibitor), acetaminophen, vaccines (e.g., live attenuated flu vaccine, FLUMIST®), antihistamine (e.g., azelastin hydrocholoride), corticosteroid (e.g., fluticasone propionate), topical decongestant (e.g., oxymetazoline hydrochloride), vitamin (e.g., vitamin c, ascorbic acid), nicotine, herbal medicines, powders, other therapeutic or diagnostic medication, or combinations thereof.

The irrigant 32 can combine with an atomizing gas and/or atomizer 88. The tip 18 may be configured to atomize the irrigant 32. The atomizing gas can have or be, for example, air, carbon dioxide, oxygen, nitrogen, nitrous oxide, another anesthetic, or combinations thereof.

Atomized irrigant 32 can include particles having a diameter from about 0.1 micrometer (0.004 mil) to about 100 micrometer (4 mil) upon exit from the tip 18. The atomized irrigant 32 particles can have a high mobility and can substantially uniformly coat and/or adhere and interact with the target site, tissues, and fluids.

The head 14 (and/or the control 10 and/or pump 11, for example) may be configured to provide various irrigant 32 flow characteristics. For example, the device 2 can be configured to produce flood (e.g., in an unbroken, or unhollow stream, or shower-like, or substantially cylindrical stream, for example), and/or atomize, and/or conical (e.g., hollow or unhollow conical stream, for example) irrigation characteristics. The flow characteristics can be automatically or manually adjusted. The flexible tip 18 or head 14 can be manually replaced with a differently configured tip 18 or head 14 to change the irrigation characteristics.

The irrigant 32 can be delivered as one or more unatomized floods or streams or flows without the mixing with an atomizing gas, or passing through an atomizer 88. For example, the device 2 can have no atomizing gas or atomizing region or other atomization elements.

FIG. 21 illustrates that the irrigant 32 can be refilled. The irrigant reservoir 30 can have an irrigant reservoir seal 140 against the wall of the irrigant reservoir 30. For example, the irrigant reservoir seal 140 can be plastic. The irrigant reservoir seal 140 can be self sealing and/or manually controlled to open and close.

The external irrigant container 56 can have fresh irrigant 32. The irrigant container 56 can have a container spout 57 configured to insert into the irrigant reservoir 30 through the irrigant reservoir seal 140 and/or the irrigation port 34. The irrigant container 56 can be advanced into the irrigant reservoir seal 154 or port 34, as shown by arrow. The contents of the irrigant container 56 can then be deposited into the irrigant reservoir 30, for example by squeezing the irrigant container 56 and/or by opening a pressure release port (not shown) on the irrigant container 56. The irrigant 32 in the irrigant container 56, and a compressed gas, can then be transferred into the irrigant reservoir 30. The irrigant container 56 can then be removed from the irrigant reservoir seal 154 or port 34 and the irrigant reservoir seal 140 can close.

c. Aspiration and Aspirant Reservoir

In addition to those features of irrigation and aspiration, and the irrigation reservoir 30 and aspiration reservoir 40 described above, the aspiration reservoir and aspiration function may include additional features. In some embodiments, the aspiration reservoir 40 may be in direct fluid communication with the aspiration port 44, via the aspiration channel 46 (see FIG. 19).

As previously described, the flexible tip 18 is shown to include the stem 80. The stem 80 (and flexible tip 18) may comprise the irrigation channel 36 and/or the aspiration channel 46. The aspiration channel 46 may also be a component of the aspirant reservoir 40, the head 14, or a separate component, or any combination. The stem 80 of the flexible tip 18 may be positioned in fluid communication with the aspirant reservoir 40 via an aspirant reservoir port 45.

The aspiration channel 46 can have an aspirant channel diameter 48. The aspirant channel diameter 48 can be the minimum internal diameter of the aspirant channel 46. The aspirant channel diameter 48 can be less than about 1 cm (0.4 in.), more narrowly less than about 5 mm (0.2 in.), for example about 3 mm (0.12 in.), or more or less.

In some embodiments, the aspiration port 44 can have an inflow check (i.e., one-way) valve 130 for inflow configured to substantially or completely prevent backflow of aspirant 42 from the aspiration channel 46 or reservoir 40. The inflow check valve 130 can be or have a ball valve, swing valve, clapper valve, umbrella valve, double check valve, duck bill valve, or combinations thereof. The inflow check valve 130 can be integral or fixedly or removably attached to the aspiration port 44 and/or the aspiration channel 46 and/or the aspirant reservoir 40.

The aspirant reservoir 40 may comprise a variety of shapes and be integral or fixedly or removably attached to the remainder of the device 2. The aspirant reservoir 40 can hold aspirant 42. The aspirant reservoir 40 can be a replaceable cartridge or ampoule. The aspirant reservoir 40 may comprise a pressure, e.g., a vacuum. The aspirant reservoir 40 can be removable, disposable, replaceable, recyclable, or combinations thereof. The aspirant reservoir 40 can be divided into multiple sub-reservoirs. In some embodiments, vanes and/or baffles may used to create multiple sub-reservoirs to provide barrier means 24 to block the flow of mucus, but allow the flow of air. In some embodiments, multiple sub-reservoirs may be used to provide a desired mucus sample to the diagnostic means 22.

In use, a pressure (i.e., vacuum) is applied via controls 10 (to be described in greater detail below), to the aspiration reservoir 40. The vacuum produces a negative aspirant pressure, causing aspirant 42 to flow as shown by arrows from the treatments region, through aspiration port 44, through the aspiration channel 46, and into the aspiration reservoir 40, where it collects. As previously described, the barrier 24 is configured to allow the passage of gas exchange (e.g., air) and excludes the passage of liquids (e.g., irrigation fluid and mucus), maintaining separation of aspirant 42 from the body 4.

d. Diagnostic

The ability to have hands-off specimen collection and analysis is ever more important as focus on infectious disease control increases. The device 2 may be adapted to provide this important function. For example, nasal specimen delivery to an embedded diagnostic means 22 (e.g., detection platform) in the head 14 and/or body 4 may incorporate a variety of platforms, including, but not limited to:

1.) Lateral Flow immunochromatographic assay, such as those commonly used now for respiratory viral detection, (e.g., RSV, influenza);

2.) Electrochemical detection microarray chips, that when exposed to a source of power, such as power source 6 provided to the head 14 via contact points, for example, produces biomolecular markers in situ which can themselves be labels for the genetic material in viruses, bacteria, and fungi, for example. It may also involve using enzymatic reactions to generate electrical signals that can be read directly from/on the assay. Alternatively, a separate reader dock with appropriate electrical/photometric specifications may be used for organism identification in the head 14. The reader dock may comprise a stand-alone device, or may be incorporated into the charging base 62, for example.

3.) Microfluidic tmRNA purification combined with nucleic acid sequenced based amplification (NASBA) that incorporates real-time detection using molecular beam fluorescent probe technology. This may be impregnated on a chip and if a power source is needed, power source 6 may provide power to the head 14 via contact points, for example. In addition, there may be a contact in the head 14 that is activated by a separate "lab activating" button on the head 14 or body 4, for example.

4.) "Biosensor" technology may also be embedded into the head 14 and may comprise a genetic plate coated with one or several antibodies to the target organism. When combined with a reagent and the organism-containing specimen and then exposed to light, it makes a visible color change so that no external source is needed to detect the organism.

5.) Other known or future developed bioassays which offer organism detection or chemical analysis on a chip and/or strip and/or genetic plate, and/or with a chemical, for example, may be placed in the head 14 and/or body 4 for hands-off laboratory handling of specimens.

Delivery of these specimens to the above mentioned detection platforms desirably would not require handing, but rather may be delivered in the exact needed quantities using pressure means, e.g., the device's pump, to guide the specimen into pressure sensitive traps/portals which may then communicate with the testing platform at the precise location for appropriate delivery. This action or process may occur only when the head is in a certain position and/or when the nozzle is completely occluded, for example.

Alternatively, the specimen could be delivered to the testing platform by manual means in which the collection chamber is gently agitated and an inside smaller chamber is thereby filled with a predetermined needed aliquot to be presented to the testing platform. This final delivery may be initiated by pressing or popping a flexible portion, e.g., a "blister," and/or a spring-loaded piston, and/or a button, on the side of the head 14, which then opens previously closed fluid communications from the aliquot chamber to the testing platform, providing hands-off pippeting.

Alternatively, the specimen could simply fill into a predetermined smaller chamber open to the rest of the collection chamber. A portion of the testing platform may extend into this smaller chamber but the rest of the testing platform may be sealed off and separated by a polypropylene wall, for example. The specimen may then travel into the rest of the testing platform via wicking, e.g., lateral flow immunochromatography, capillary action, e.g., microfluidic capillary action, electrical charge, and/or an opening of the separating wall by way of a blister breaking point, membrane, or seal, as non-limiting examples.

The device 2 including the diagnostic means 22 is well suited for hospital and clinic use, as well as self diagnosis in the home. The device 2 including the diagnostic means 22 may be used in medicine for detecting all types of microorganisms, in warfare for weaponized bacteria, agents, and viruses, in emergency services, in high volume travel sites such as airports to detect infected travelers and in schools and daycares to define infected students. The device 2 including the diagnostic means 22 may also house testing platforms which detect labs such as metabolic panels, glucose, insulin levels, drug levels, b-natiuretic peptide, d-dimers, and CRP from the gathered specimen.

After use (i.e., aspiration), the head 14 and/or aspirant reservoir 40 may contain contaminated fluids such as irrigant and mucus (i.e., aspiration fluid 42). The irrigant reservoir 30 and/or the aspirant reservoir 40, and/or the entire head 14, or other components of the head 14 or body 4, may then be used, and/or removed for use, as a diagnostic device to test and/or evaluate the contaminated fluids for disease or medical conditions such as injuries, disabilities, disorders, syndromes, infections, and/or viruses, for example. If removed, the component(s) removed may be sealed to avoid cross contamination. Access may be provided to allow lab personnel access to the fluid 42 to be tested.

In some embodiments, the head 14 and/or the aspirant reservoir 40, for example, may include the diagnostic means 22, such as those previously described, or any combination, as non-limiting examples (see FIGS. 22A through 22C). The diagnostic means may be imbedded in the head 14, or aspirant reservoir 40, or the body 4, or may be a removable component for further testing and/or evaluation. The diagnostic means 22 may provide immediate results or the head 14 and/or diagnostic means 22 may be sent to a lab for further action.

The diagnostic means 22 may comprise a testing platform or an analysis system 90, such as a lateral flow test strip analysis system (i.e., immunochromatography), and/or a micro total analysis system (i.e., lab on a chip), for example, and may incorporate microfluidics including mechanical flow control devices like pumps and valves or sensors like flow meters and viscometers. The lab on a chip may be made of glass, silicone, ceramics, or metal, for example.

The device 2 and diagnostic means 22 may simplify and provide hands-off gathering of a specimen by reducing the testing process to nasal suctioning with the device 2 using the aspiration function, and presenting a predetermined amount of the aspirated fluid sample 42 to the diagnostic means 22.

Once the sample 42 has been presented to the device 2, e.g., is within the head 14, the sample may be presented to the diagnostic means 22 either manually (e.g., pressure applied), or automatically (e.g., solenoid driven). In some embodiments, the sample 42 may be drawn into a sample collection well, or capillary, or chamber 92, for example, such as by shaking the head 14 (or the device 2) so as to draw the fluid sample 42 into the chamber 92, or by capping the flexible tip 18 with the cap 20, or finger 76, actuating the aspiration function again so as to cause an occluded suction, which draws the aspiration fluid sample 42 into the chamber 92. Once the sample is within the chamber 92, it may be available to the analysis system 90 for testing. The chamber may provide a predetermined volume of fluid sample 42 to the analysis system 90.

Once in the chamber 92, the predetermined volume of sample 42 may then be automatically presented to the analysis system 90, or an action may be necessary, such as manually popping a blister 94, or the push of a button, or movement of a switch, on the side of the head 14, for example, to allow entry of the sample into and/or onto the analysis system 90.

In some embodiments, there may be one or more chambers in fluid communication with the diagnostic means 22 whose arrangement and communication with the sample collection chamber 92 allows a predetermined test sample size to be drawn. The test sample may be combined with a reagent from one or more of the chambers to form an aliquot to then be delivered to the analysis system 90.

In some embodiments, the diagnostic means 22 may then display and/or present a result or results of the test(s). For example, the results may be displayed as a change of color of an indicator 95 on or in the diagnostic means 22 and/or head 14, or a test strip 96 may be removed from the diagnostic means, or visible within the head 14 and/or aspiration reservoir 40, for example An electrical contact 97 may be included to provide electrical power to the diagnostic means 22.

The diagnostic means 22 may accommodate microbiologic tests including, but not limited to: influenza A and B, avian flu, RSV (respiratory syncytial virus), adenovirus, Legionella, CNV, EBV, Group A beta hemolytic streptococcus, S. pneumoniae, N. meningitides, mycoplasma, Staphloccus aureus, Malaria, HIV, rhinovirus, coccsackie virus, smallpox, anthrax, botulinum toxin, ricin, ebola, rabies, brucellosis, (plague) *yersinia pestis, coxeilla burnetti* (Q fever), T2 mycotoxins, *francisella tularensis* (tularemia), viral equine encephalitis, viral hemorrhagic fever, and *burkholdria mallei* (glanders).

The diagnostic means 22 may accommodate toxicologic and/or chemical tests including, but not limited to: amphetamines, cocaine, opiates, phencyclidine, tetrahydrocannabinol, acetaminophen, barbiturates, benzodiazepines, methadone, propoxyhenone, tricyclic antidepressants, calcium channel blockers, ethyl alcohol, ethylene glycol, ketones, glucose, hypoglaecemics, cytokines, interleukins, insulin, Hemoglobin A1C, electrolytes, human choreonic gonadotropin (pregnancy test), thyroid-stimulating hormone (TSH), T3 blood test, T4 blood test, c-reactive protein (CRP), and erythrocyte sedimentation rate (ESR).

The diagnostic means 22 may include real time polymerase chain reaction tests and/or immunoassays for viruses, bacteria, and cancers, for example.

B. Power Source

According to one desirable technical feature, the device 2 can have a power source 6. FIG. 23 illustrates the power source 6 can be stored completely or partially in a compartment, for example, a power source compartment within the body 4. The power source 6 may comprise an electrical power source (e.g., a battery or capacitor), and/or a mechanical power source (e.g., a flywheel or spring for energy storage), and or a compressed gas (e.g., a canister of compressed gas), as non-limiting examples. In some embodiments, the power source 6 is a rechargeable power source. The rechargeable power source may be non-removable (i.e., the device 2 is placed on or in a power source recharger 62), or the rechargeable power source may be removed to be recharged and/or replaced.

The recharger 62 and/or the base 4 may include a direct, or sealed, or inductive coupling region 98, 99 respectively, for example, to allow the device 2 to be electrically and/or mechanically coupled to the recharger for recharging (see FIGS. 23 and 24). The recharger 62 may also be a rechargeable device, and/or the recharger may be coupled to an external supply of electricity (e.g., 120 VAC electrical wall outlet). The recharger 62 may include an illumination source or light 100 (e.g., LED), to provide indications, such as power on, recharging, and recharged, as non-limiting examples, and may be placed on a surface, e.g., desk or counter top, or mounted to a wall. As previously described, the recharger 62 may incorporate a reader dock with appropriate electrical/photometric specifications that may be used for organism identification in the head 14, as part of the diagnostic means 22. Alternatively, the reader dock may comprise a stand-alone device, and/or may draw power from the recharger 62.

In an alternative embodiment, the power source 6 may include one or more non-rechargeable electrical cells (e.g., one or more batteries), for example, four AA alkaline batteries in series, as a non-limiting example.

In some embodiments, the power source 6 may comprise a Lithium Ion power source, and may be configured to supply about 100 mAh, or about 500 mAh, or about 750 mAh, or about 1000 mAh, or more or less, at about 7.4 volts, although it is to be appreciated to one of skill in the art that the power source 6 may be configured to supply a wide range of voltages and capacities. The power source 6 desirably possesses a capacity sufficient to allow operation with recharging and/or power source replacement not more frequently than once per five minutes, or fifteen minutes, or thirty minutes, or hour, or day, or week, or month, or year, for example, for many or most applications. The power source 6 can also be configured to connect to an external supply of electricity (e.g., a 120 VAC electrical wall outlet).

The power source compartment can be accessible from outside of the body 4 through a power source compartment door (not shown). The power source compartment door can be removably attached to the body 4. The power source compartment door can be hingedly attached to the body 4.

The power source 6 may be electrically coupled to an illumination source or light 102 (e.g., LED), to provide indications, such as power on, power supply capacity, and irrigation and/or aspiration functions activated, as non-limiting examples.

C. Device Controls

According to one desirable technical feature, the device 2 can have a control 10 that can be configured to provide multiple functions (see FIG. 25). The control may comprise buttons, switches, triggers, levers, electrical circuitry, interaction between any of these, and may include microprocessor control 110, as non-limiting examples. The control 10 can enable user-induced, and/or automated actuation of the device 2. For example, the device 2 may be actuated by contact with the area to be irrigated and/or aspirated, e.g., a nostril. The control 10 can be coupled to a dual function switch, or one or more multiple-function switches, or one or more single-function switches, or combinations thereof, as non-limiting examples. The switch(s) 112 may comprise buttons, rockers, toggles, triggers, or other known configurations and combinations, and may be attached to or integral with the body 4 and/or head 14, or combinations thereof.

The control 10 can manually (e.g., user-induced) or automatically (e.g., electrically, pneumatically, stored energy) actuate and/or power and/or otherwise control, either directly or indirectly, the irrigation and/or aspiration functions. The control 10 may be adapted to provide variable control of irrigation and/or aspiration, and may include the ability to provide a delay, such as an adjustable delay, for irrigation and/or aspiration. The control 10, including the switch 112, can be simple and intuitive to use.

The control 10 (or other elements) can be used to transmit power from the power source 6 to activate electronics (e.g., the pump 8, motor 9, and/or microprocessor 110), valves, manually pump, or any combinations thereof. The control 10 can be configured to receive input from the one or more buttons 112.

FIGS. 26 through 29 show an exemplary embodiment for methods of use of the device 2. As seen, the control 10 can produce a first input, for example a pressing translation 114 of the button 112. The control 10 can produce a second input, for example, a pressing translation 116 of the switch 112 that is not the first input. The first input can control the irrigation, for example whether irrigant is manually expelled from the head 14, and/or the frequency and/or volume of the irrigation flow. The second input can control the aspiration, for example whether aspiration is on or off and/or the intensity of the pressure and/or flow rate of aspiration.

In an alternative embodiment, the control 10 can receive a first input, for example a pressing translation 114 of the button 112. The control 10 can receive a second input, for example, a pressing translation 116 of the button 112 that is not the first input. The first input can control the irrigation, for example whether irrigant is automatically expelled from the head 14 (i.e., on or off) and/or the intensity of the pressure and/or flow rate of the irrigant and/or the frequency of the irrigant flow. The second input can control the aspiration, for example whether aspiration is on or off and/or the intensity of the pressure and/or flow rate of aspiration.

Figure 26:
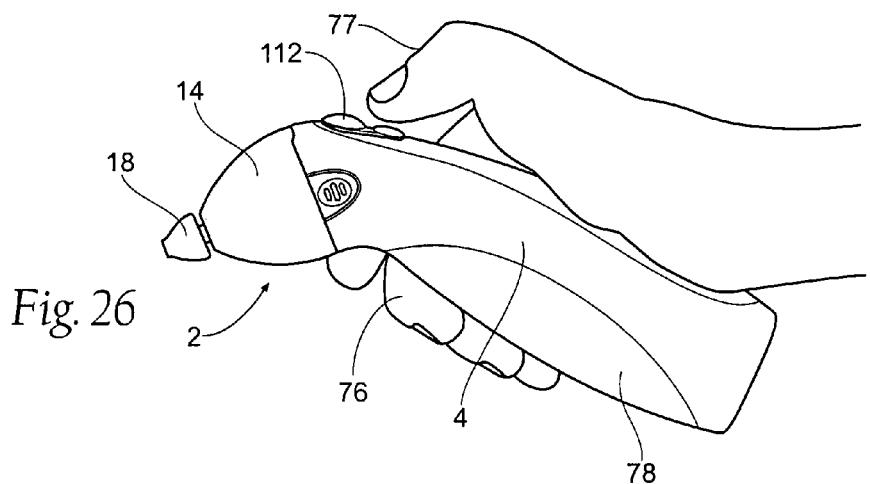
FIGS. 26 through 29 illustrate a variation of a method of using a variation of the irrigation and aspiration device.

FIG. 26 illustrates that a user can ergonomically hold the body 4 in a single hand. The user can rest a finger 76 or thumb 77, for example, on the button 112, allowing the button 112 to be operated by a single digit (i.e., finger 76 or thumb 77). The palm 74 and/or other fingers 76 can substantially or completely rest on the grip pads 78.

Figure 27:
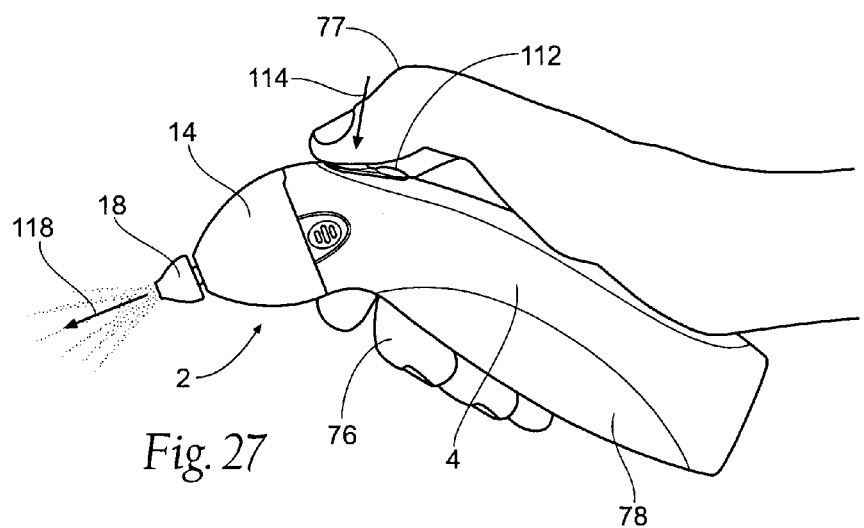

By way of example, FIG. 27 illustrates that the thumb 77 can press a first portion of the button 112, as shown by arrow 114. The pressing 114 of the button can control the other of the irrigation and/or aspiration not controlled by the pressing 116. As shown for example, pressing the button 112 can actuate the device 2 to create a pressure resulting in a pressured fluid delivery resulting in the irrigant flow 118. Releasing the pressing 114 of the button 112 can stop the pressurized fluid delivery. The inward distance the button 112 is pressed 114 can directly or indirectly correlate to the pressure and/or volume of the aspiration or irrigation.

Figure 28:
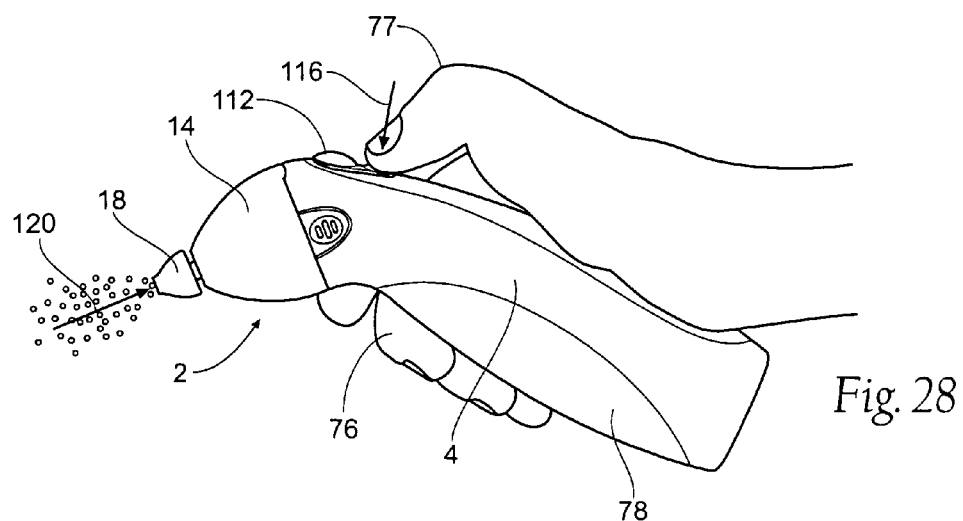

By way of example, FIG. 28 illustrates that the thumb 77 can press a second portion of the button 112, as shown by arrow 116. The pressing 116 of the button 112 can control irrigation and/or aspiration. As shown for example, pressing the button 112 can actuate the device 2 to create a suction resulting in aspirant flow 120, as shown by arrow 120. Releasing the pressing 1164 of the button 112 can stop the suction and aspirant flow. The inward distance the switch 112 is pressed 116 may directly or indirectly correlate to the pressure and/or volume of the aspiration or irrigation.

Figure 29:
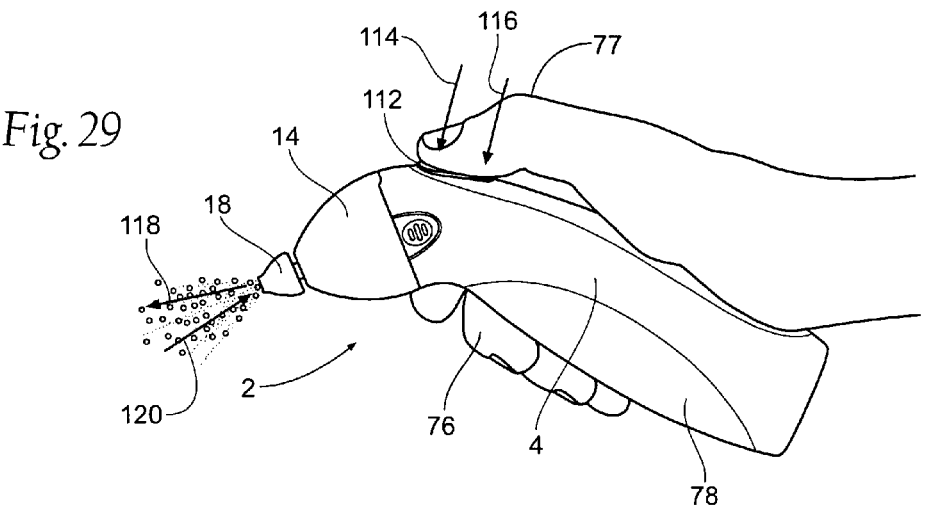

By way of example, FIG. 29 illustrates that the thumb 77 can press both the first portion and the second portion of the button 112, as shown by arrow 114 and arrow 116, so as to concurrently depress the first portion and the second portion of the button 112. Pressing 114 the first portion of the button 112 and pressing 116 the second portion of the button 112 concurrently can actuate the device 2 to create a pressured fluid delivery resulting in the irrigant flow 118, and concurrently resulting in a suction causing an aspirant flow 120.

Alternatively, the thumb 77 can alternate pressing the first portion and the second portion of the button 112, by rocking back and forth between 114 and 116, or 116 and 114. Pressing 114 the first portion of the button 112 and pressing 116 the second portion of the button 112 with a rocking motion can actuate the device 2 to create a pressured fluid delivery resulting in the irrigant flow 118, and then stepwise resulting in a suction causing an aspirant flow 120.

In an exemplary embodiment illustrated in FIG. 25, button 112 can comprise a first switch 122 configured to control, for example via the pump 8, pressure in the aspiration channel 46 (i.e., aspiration pressure). The first switch 122 may comprise a variable switch adapted for control of the aspiration function, including whether aspiration is on or off and/or the intensity of the pressure and/or flow rate of aspiration. The button 112 can have a second switch 124 configured to manually actuate a second pump 11 to deliver pressure, either directly or indirectly, to the irrigant reservoir 30 and irrigation channel 36. The second switch 124 may comprise one or more elements 176, 178 adapted to translate movement from the button 124 (e.g., by pressing) to the pump 11, so as to result in a pressured fluid delivery resulting in the irrigant flow 118. As previously described above in relation to the button 112, the first switch 122 can be activated by a first digit (e.g., the thumb 77), and the second switch 124 can also be activated by the first digit (e.g., the thumb 77), or a second digit (e.g., the index finger 76), for example, to provide individual or concurrent control and operation of the irrigation and/or aspiration functions.

It is to be appreciated that one or more buttons can control the aspiration (i.e., suction) and irrigation with one digit (i.e., finger 77 or thumb 78). The button 112 can be configured to receive multiple input signals (e.g., from the user). The button 112 can have one, two or more degrees of freedom. For example, the button 112 can receive a pressing translation, and/or a sliding translation, or combinations. The control 10, via the multiple input signals (e.g., pressing and sliding), can be configured to separately control (e.g., binary/two-state control (on/off) and/or variable control of the magnitude of power to gradually increase or decrease, as non-limiting examples) the aspiration and the irrigation. For example, one input signal (e.g., pressing or sliding or both) can control the aspiration and another input signal (e.g., pressing or sliding or both) can control the irrigation. The sliding can be along the longitudinal axis of the body 4 and/or head 14. The pressing can be orthogonal to the sliding, as a non-limiting example.

The button 112 can be bi-functional. The button 112 can have a rocker platform that can encase a variable speed switch to provide variable control of irrigation and/or aspiration. The variable speed switch can be moved from an off setting to a maximum speed (and/or on/off) setting by sliding the variable speed switch along the platform. The platform can be flush with, inside, or outside the device 2 case 5. The platform can be hinged at a first end and free at a second end. The platform can be resiliently pressed toward the remainder of the device 2, for example, over a balancing spring. Pressing the platform can manually actuate, or activate automatic actuation of, irrigation and/or aspiration.

D. Pumps

According to one desirable technical feature, the device 2 can have one or more pumps 8 and 11 that can be configured to provide a pressure. The first pump 8 can produce a different or the same flow rate and/or pressure as the second pump 11.

Figure 30:
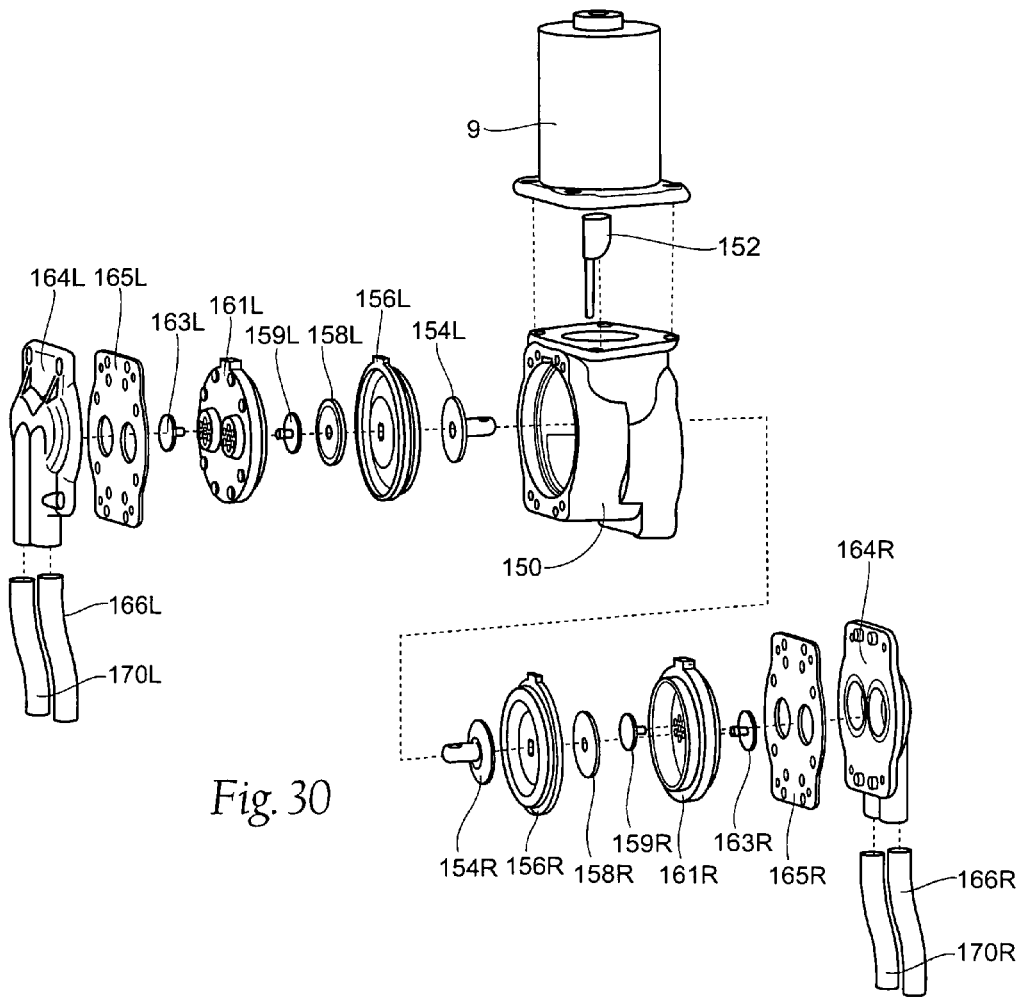
FIG. 30 is an exploded view of a variation of a pump and motor adapted for use with a variation of the irrigation and aspiration device.
Figure 31:
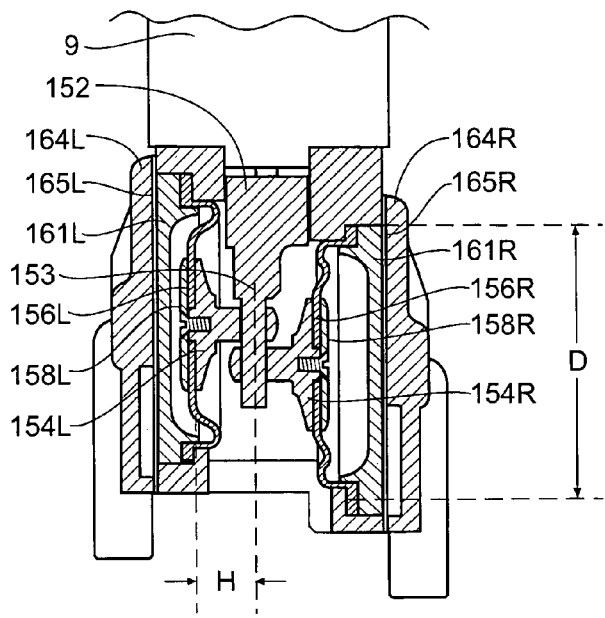
FIG. 31 is a section view of the pump as shown in FIG. 30.
Figure 32:
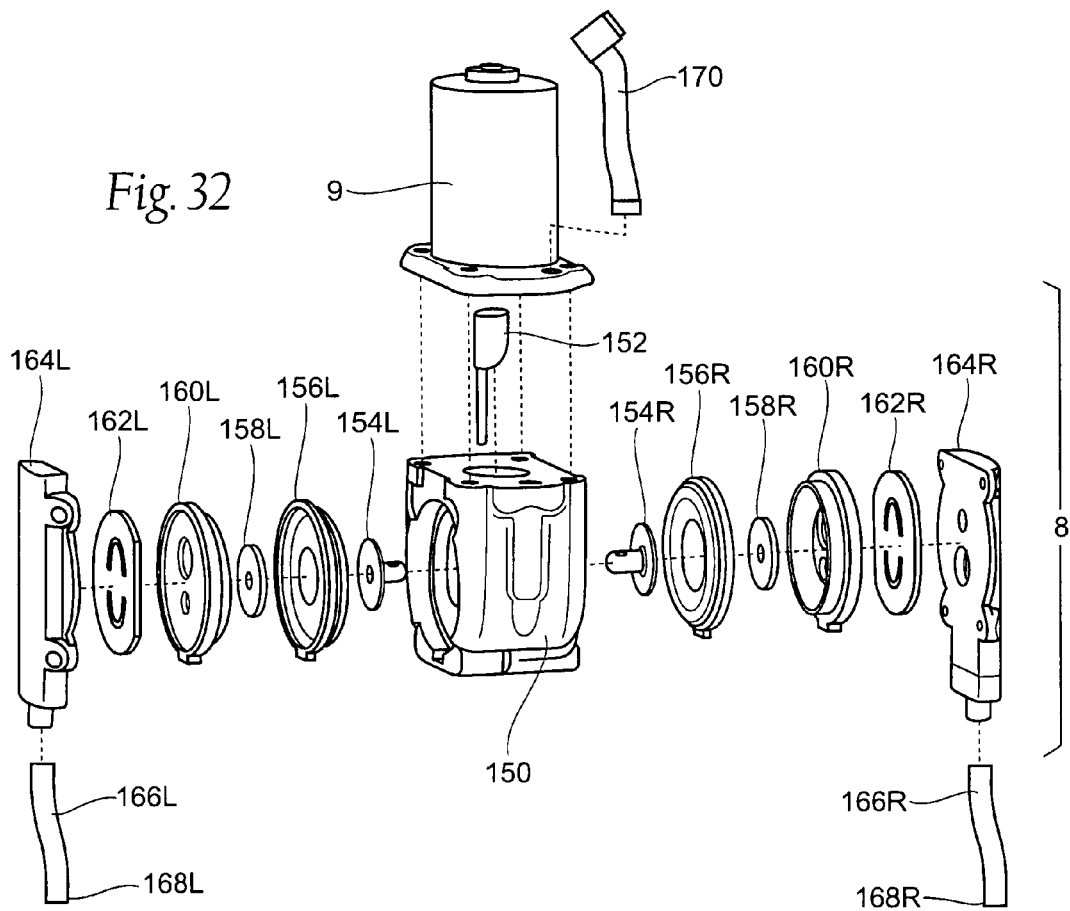
FIG. 32 is an exploded view of an alternative variation of the pump and motor as shown in FIG. 30.

In some embodiments, the pump 8 can be, for example, a piston pump, a rotary vane pump, a linear pump, and/or diaphragm pump (i.e., a membrane pump, positive displacement pump), such as a dual diaphragm pumps 8, as shown in FIGS. 30 through 32. The pump 8 may have at least two oppositely-oriented oscillating shafts, rods, or membranes. In other embodiments, the pump 8 can be or have a compressed gas (e.g., air, carbon dioxide, nitrogen) canister 210 that can be configured to controllably store and release the compressed gas.

The pump 8 can be connected to or interface with the control 10, directly or indirectly through the motor 9. The motor 9 may be chosen to balance a desired rpm with an acceptable current draw. As previously described, the control 10 may include a microprocessor 110 configured to regulate and/or vary the motor speed to control irrigant delivery pressure and/or aspirant suction pressure. The aspirant suction pressure created by the pump 8 can be, for example, up to about 200 mm Hg (3.86 psi), or more narrowly about 120 mm Hg (2.32 psi), or more narrowly about 80 mm Hg (1.55 psi), or more narrowly about 50 mmHg (0.966 psi), or more or less. The control 10 can receive one or more inputs from the button 112. The microprocessor 110 can analyze the button position to control the motor speed. As previously described, the pump 8 and/or control 10, may incorporate a valve 128 or control algorithm to limit the aspirant suction pressure to about 100 mm Hg, for example.

The pump 8 can have doubled-up diaphragms, as a non-limiting example. The pump 8 can be manually and/or electrically powered. The pump 8 can be attached to an AC or DC-driven motor 9. The pump 8 can be driven by motor 9 that can be driven by the power source 6. The pump 8 can have one or more blowers, turbines, fans, diaphragms, bellows, or combinations thereof.

An exemplary embodiment of the pump 8 can be seen in FIGS. 30 and 31. Pump chassis 150 houses two oppositely-oriented oscillating diaphragms. For simplicity, the configuration of one side of the pump 8 will be described (i.e., a left side), with the other side being a mirror image (i.e., a right side). It is to be appreciated that both sides of the double diaphragm pump need not be mirror images. Within the pump chassis 150 resides a throw pin 152, with a diaphragm arm 154L rotatably coupled to the throw pin 152. The diaphragm arm 154L comprises an optimized diaphragm arm height H. The diaphragm arm height H is shown to be measured from the center of the diaphragm arm throw pin shaft hole 153 to the top surface of the diaphragm 156L, and may include a length of about 4 to 8 mm, or more narrowly about 5 to 7 mm, or more narrowly about 6.5 mm, or more or less. The shorter the diaphragm arm height, the more the diaphragm 156L undesirably "rocks," and the longer the diaphragm arm height, the size of the pump increases. The diaphragm arm height may be advantageously reduced as much as possible, with the limitation of shortening the diaphragm arm height relating directly to the diaphragm diameter D and how much rocking the diaphragm does per stroke.

Advantageously, the diaphragm 156L may also be optimized with a diameter D and a generally "M" or "S" cross-sectional shape to most efficiently accommodate the rocking motion (see FIG. 31), and to push a majority of the air out and pull a majority of the air in for each stroke. The diaphragm 156L may be sandwiched between the diaphragm arm 154L and a diaphragm plate 158L. The diaphragm 156L comprises an optimized diameter D, and may include a diameter of about 20 to 40 mm, or more narrowly about 25 to 35 mm, or more narrowly about 30 mm, or more or less, the diameter D 156L providing an optimized flow per stroke. The optimized diameter D allows the pump to fit within the base 4 and allows the pump to operate at the lowest possible RPM while providing desired flow requirements. The diaphragm plate 158L provides a rigid center region of the diaphragm 156L. The diaphragm plate 158L also improves efficiency by helping to ensure that all the air is pushed out and pulled in for each stroke. Without the diaphragm plate 158L, the diaphragm 156L may instead merely stretch and/or flex.

A diaphragm chamber 161L may be seated on or adjacent to the diaphragm 156L, with an intake one-way umbrella valve 159L and an exhaust one-way umbrella valve 163L positioned on respective sides of the diaphragm chamber 161L. The use of the one-way umbrella valves and the diaphragm chamber help to minimize the thickness of the pump 8. A manifold gasket 165L and a pump manifold 164L may be mounted to the chassis 150, and an exhaust hose 166L and/or intake hose 170L may be coupled to the manifold 164L. Again, this or a similar configuration is repeated on the other side of the pump 8. The intake hose 172 may then extend through the body 4 to the aspiration aperture 192. The throw pin 152 may be coupled to the motor 9 to provide oscillating movement of the oppositely-oriented oscillating diaphragms.

Large diaphragms with high throw produce a desired high flow with low volume. Due to a physical limitation of space within the defined base 4, the ability to increase the diameter of the diaphragm may be limited. In order to provide the desired high flow with low volume, the configuration of the diaphragm 156L having a diameter D sandwiched between the diaphragm arm 154L having a height H, and the diaphragm plate 158L may be optimized to provide the improved high level of flow with a high level of oscillation or throw. The relationship between the diameter D and the height H may be expressed as the ratio of D/H, where the ratio may be from about 2/1 to about 10/1, and more narrowly about 4/1 to about 6/1, and more narrowly about 5/1, or more or less. The improved performance of such a device was not possible in prior devices.

In some embodiments, displacement may be maximized by using the double diaphragm configuration as described, increasing the rpm of the pump 8 only high enough to meet flow requirements, and including the unique diaphragm with the distinct shape and diameter to allow increased flow per stroke, as previously described.

The pump 8 can have a total volume. For example, the pump 8 can have a volume of about 100 cc (6.1 in$^3$), more narrowly about 75 cc (4.6 in$^3$), and more narrowly about 50 cc (3.05 in$^3$), or more or less.

FIG. 32 shows an alternative embodiment of the pump 8. The alternative embodiment is similar to the pump 8 as shown in FIGS. 30 and 31, except the diaphragm chamber 160L interfaces with a flat valve 162L.

Figures 33, 34A, 34B:
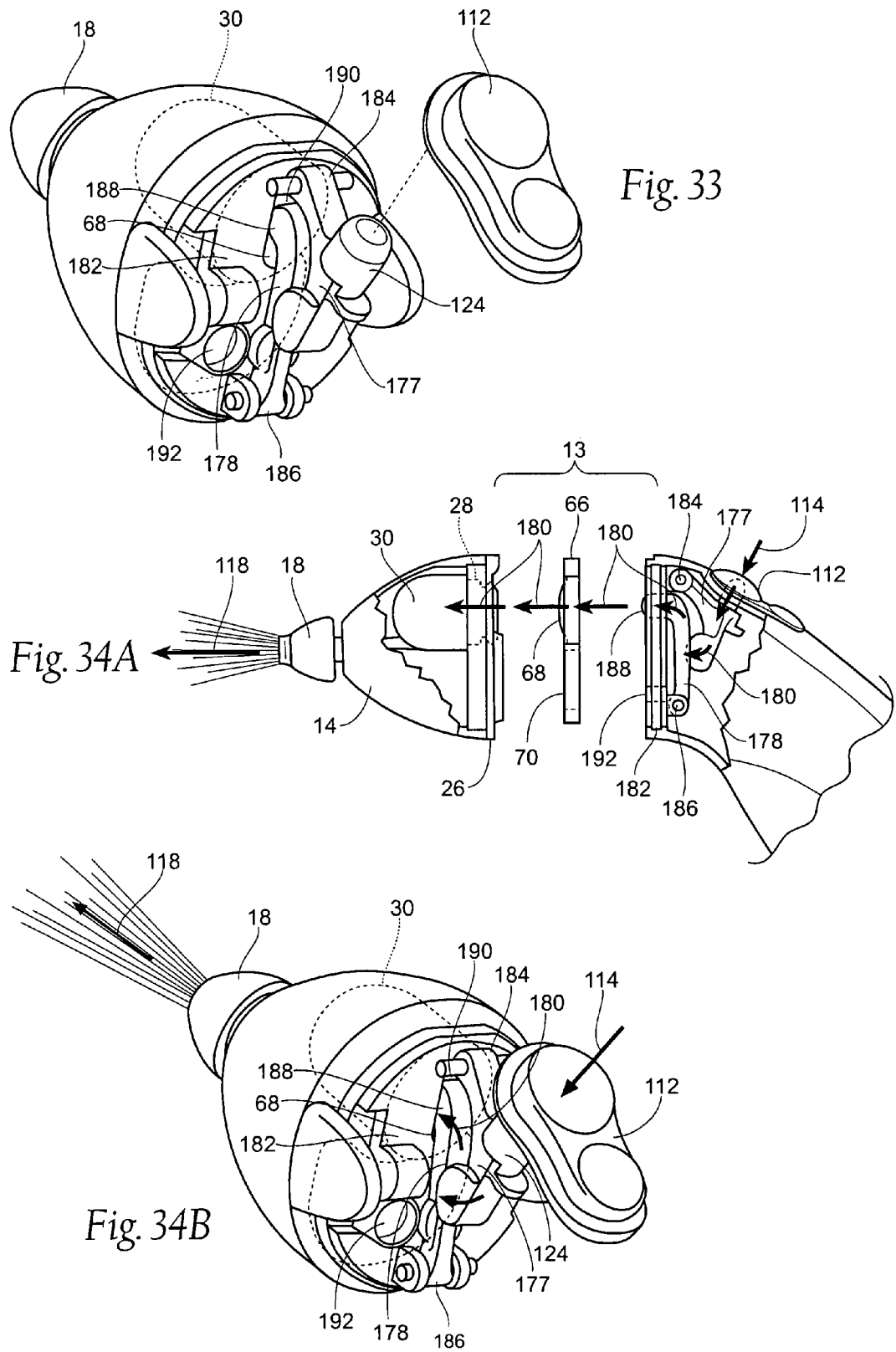
FIG. 33 is a perspective view of a variation of the head of the irrigation and aspiration device, similar to the head shown in FIG. 25, showing a variation of the controls adapted to provide user control of the irrigation function.
FIG. 34A is a side exploded view in partial cutaway of the head of the irrigation and aspiration device shown in FIG. 33, showing a variation of the controls adapted to provide either direct or indirect user control of the irrigation function, and showing features of the invention that comprise at least a portion of an interface region.
FIG. 34B is a perspective view of the head of the irrigation and aspiration device shown in FIG. 34A, showing a variation of the controls adapted to provide a transfer of force from the user control of the irrigation function.

An exemplary embodiment of a pump 11 can be seen in FIGS. 33 and 34. The pump 11 can be connected to or interface with the control 10, directly or indirectly through the button 112 and/or switch 124. One or more pivot arms, such as a first pivot arm 177 and a second pivot arm 178 may be induced into pivotal motion to apply a force 180 either directly or indirectly to the irrigation reservoir 30, e.g., through the irrigation bellows 68. Mounting plate 182 may provide a first pivot point 184 for the first pivot arm 177, and a second pivot point 186 for the second pivot arm 178. In some embodiments, the non-pivot end 188 of the second pivot arm 178 may extend partially or completely through an irrigation aperture 190 in the mounting plate 182 (see also FIG. 8C). The button 112 may be pressed or pushed 114 by the user to translate the downward motion 114 into the force 180, through the interface region 13, and upon the bellows 68 by the non-pivot end 188 of the second pivot arm 178. As can be seen, an aspiration aperture 192 provides a path for aspiration vacuum 49 to pass through the interface region 13 and extend from the head 14 to the base 4.

E. Flow Diagrams

According to one desirable technical feature, FIGS. 35A and 35B illustrates that the device 2 may be adapted to provide partial or complete separation of the irrigation and aspiration systems and functions. As seen, both the irrigant and aspirant flows may be maintained in separation from each other, providing a device where cross contamination may be avoided. As previously described, the irrigation and/or aspiration systems and functions may have an interface region 13 between the body 4 and the head 14. The interface region may directly or indirectly connect the pump 11 to the irrigation reservoir 30 and/or the vacuum pressure 49 to the aspiration reservoir 40, for example. The interface region 13 may be adapted to provide complete or partial separation of the irrigation and aspiration systems and functions.

In some embodiments, irrigant 32 may be expelled from the irrigant reservoir 30 with mechanical pressure 180 applied either directly or indirectly to the irrigant reservoir 30 via control 10 and pump 11 (see FIG. 35A). In other embodiments, irrigant 32 may be expelled from the irrigant reservoir 30 with mechanical pressure 180 applied to the irrigant reservoir 30 with a squeeze by the user (see FIG. 35B). A pump 11 may or may not be included. The irrigant 32 flows out the irrigant reservoir 30, through the irrigation channel 36, and out the irrigation port 34. Either concurrently, or before, or after, or any combination, the pump 8 may be energized (e.g., via control 10 and motor 9) to produce aspiration vacuum pressure 49 to draw air and aspirant 42 from the treatment region into the aspirant reservoir 40. The resulting vacuum 49 can draw aspirant flow 120, as shown by arrows, through the aspiration port 44 and into the aspirant reservoir 40. Barrier 24 may prevent contaminated aspiration material 42 i.e., fluids, from entering the body 4.

FIG. 35A illustrates that the device 2 can have a first pump 8 and a second pump 11. The first pump 8 and/or second pump 11 can be manual or automatic (e.g., driven by an electric motor). For example the first pump 8 can be automatic and the second pump 11 can be manual, as shown. The first pump 8 can provide aspirant suction pressure to the aspirant intake hose 172. The outgoing pressure from the first pump 8 can be exhausted through the exhaust hose 166 and/or exhaust port 168.

The second pump 11 can pressurize the irrigant 32 in the irrigation reservoir 30 and/or irrigation channel 36. The second pump 11 can be pumped to produce a force 180, as shown by arrow, for example by hand (e.g., with a thumb on a button). The second pump 11 can be actuated by a thumb 77 on a button 112 on the body 4 of the device 2. The irrigant 32 can be delivered from the irrigation port 34 in a non-atomized stream or spray, or the irrigant 32 can be atomized upon passing through or exiting the flexible tip 18.

The button 112 can be in a position configured to produce aspiration and no irrigation. The button 112 can be in a position configured to produce irrigation and no aspiration. The button 112 can be in a position configured to produce aspiration and irrigation. All or part of the exhaust pressure from the pump 8 can flow out of the device 2 as exhaust flow 170, as shown by arrows.

Separation of irrigation and aspiration functions allows for the device 2 to be configured to prevent the irrigant 32 from the irrigant reservoir 30 from flowing solely from the application of vacuum pressure 49 in the head 14, and more specifically in the aspirant channel 46 and aspirant reservoir 40.

V. Additional Embodiments

A. Bulb Designs

Figure 36:
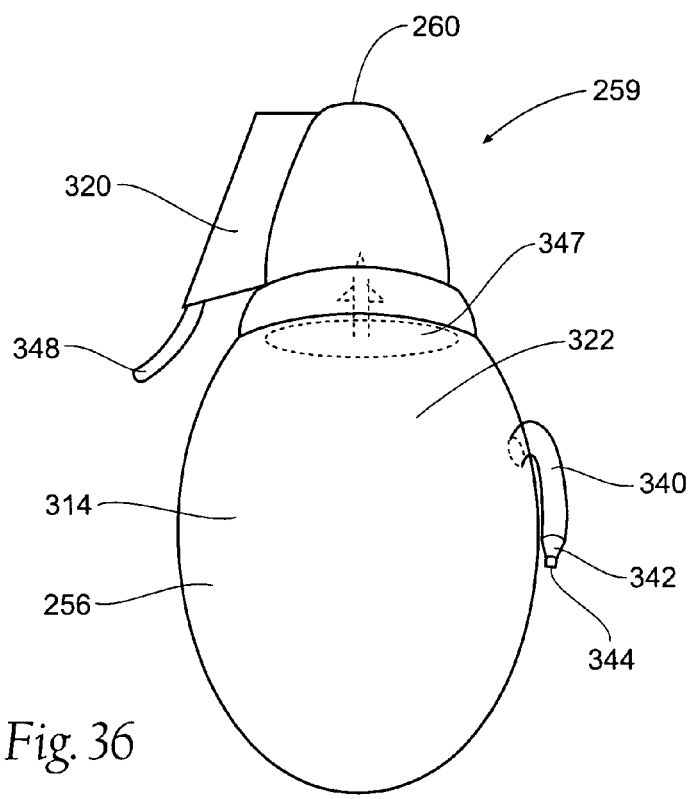
FIG. 36 is a partially see-through view of a variation of the irrigation and aspiration device.

FIG. 36 illustrates that the aspiration reservoir 256 can be a resilient container, such as an elastomeric bulb 314. The aspiration reservoir 256 can have an exhaust conduit 340. The exhaust conduit 340 can be in fluid communication with the aspiration reservoir 256. The exhaust conduit 340 can have an exhaust valve 342 and an exhaust port 344. The exhaust valve 342 can be a check valve configured to flow away from the aspiration reservoir 256.

The nozzle 259 can be integral with or removably attached to the aspiration reservoir 256. The aspiration port 260 nozzle 259 or the aspiration reservoir 256 can have an aspiration valve 346. The aspiration valve 347 can be a check valve, for example, such as an umbrella check valve 347.

The irrigation component 320 can have an irrigation trigger 348. The irrigation trigger 348 can be operated by a single digit. When the irrigation trigger 348 is pulled or squeezed, the irrigation component 320 can dispense irrigant 257.

When the aspiration reservoir 256 is squeezed, the aspiration valve 347 can close and the exhaust valve 342 can open. The aspirant 258 in the aspiration reservoir 256 can be forced out the exhaust conduit 340 and the exhaust port 344. The exhaust valve 342 can be a duckbill valve. When the previously-squeezed aspiration reservoir 256 is relaxed, the exhaust valve 342 can close and the aspiration valve 347 can open. Suction can then result at the aspiration port 260 and aspirant 258 can be drawn into the aspiration reservoir 256.

Figure 37:
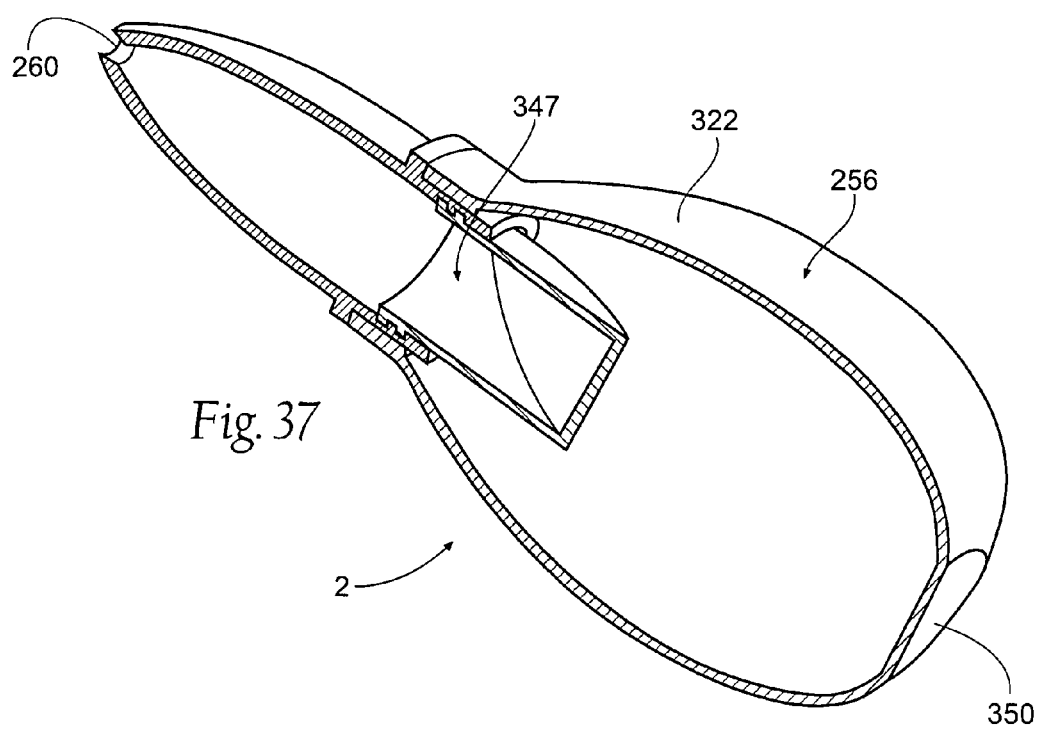
FIG. 37 is a cut-away view of a variation of the aspiration component of the irrigation and aspiration device.

FIG. 37 illustrates that the aspiration valve 347 can be a duckbill valve (the irrigation component 320 is not shown). The aspiration component 322 and/or the device can have a base 350. The base 350 can be configured to enable the device 2 to stand on a flat surface (e.g., a table), for example, keeping the aspiration 260 and other ports off the flat surface.

Figure 38:
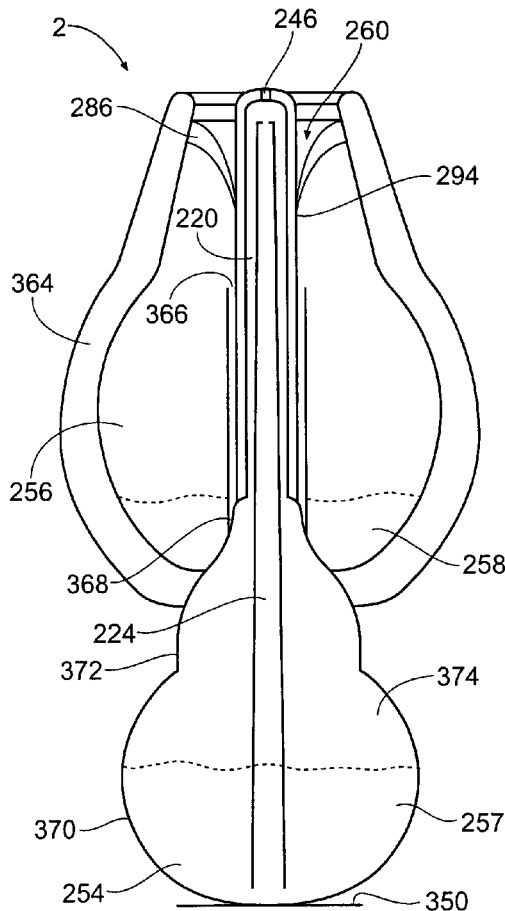
FIG. 38 is a cut-away view of a variation of the irrigation and aspiration device.

FIG. 38 illustrates that the aspiration reservoir 256 can be in a resilient vacuum bulb 364. The vacuum bulb 364 can be elastomeric. The aspiration reservoir 256 can be in fluid communication with the irrigant reservoir 254, for example, via an irrigation-aspiration port 366. The irrigation-aspiration port 366 is configured to be away from the aspirant fluid level in the aspirant reservoir 256.

An irrigation-aspiration valve 368 can be in fluid communication with the aspiration reservoir 256 and the irrigant reservoir 254. The irrigation-aspiration valve 368 can be a check valve. The irrigation-aspiration valve 368 can be a valve permitting flow only from the aspiration reservoir 256 to the irrigant reservoir 254 and preventing flow from the irrigant reservoir 254 to the aspiration reservoir 256.

The aspiration valve 346 can be a one-way check valve permitting flow into the aspiration reservoir 56.

The irrigant reservoir 254 can be in an irrigant container 370. The irrigant container 370 can be rigid, for example a plastic bottle. The irrigant container 370 can be integral with or removably attachable to the remainder of the device at an attachable reservoir joint 372. The atomization fluid reservoir 374 can be the top of the irrigant reservoir 254, above the level of the irrigant 257.

The base 350 can extend from the reservoir container. The base 350 can be wider than the widest portion of the remainder of the device 2.

Squeezing the vacuum bulb 364 can atomize and eject irrigant 257 from the atomization port 246. For example, when the vacuum bulb 364 is squeezed, the irrigation-aspiration valve 363 can open and the irrigant reservoir 254 can be pressurized via the irrigation-aspiration port 366. The increased pressure in the irrigant reservoir 254 can cause the irrigant 257 to flow through the irrigation channel 224. The increased pressure in the irrigant reservoir 254 can also force gas in the irrigant reservoir 254 (e.g., above the irrigant 257) through the atomization channel 220.

Relaxing the previously squeezed irrigation-aspiration valve 368 can suction aspirant 258 into the aspiration reservoir 256. For example, the irrigation-aspiration valve 368 can close. The negative pressure in the aspiration reservoir 256 can draw in aspirant 258 by opening the aspiration seal 294 in the aspiration port 260.

Figure 39:
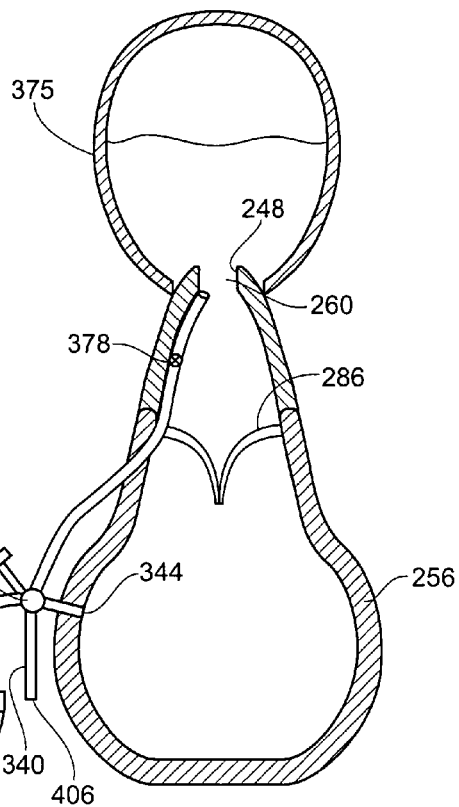
FIG. 39 is a partial cut-away view and partial schematic diagrams of a variation of the irrigation and aspiration device.

FIG. 39 illustrates that one or more covers 375 can be configured to fit over the aspiration 260 and/or irrigation 248 and/or atomization ports 246.

The device 2 can have a manually or automatically controllable dual exhaust valve 376. The dual exhaust valve 376 can be passive or active. The dual exhaust valve 376 can regulate excessive fluid pressure from the aspiration reservoir 256 and/or the irrigant reservoir 254 to an exhaust conduit 340. The excessive fluid pressure can exit the exhaust conduit 340 as an exhaust flow, shown by arrow.

An irrigation valve 378 can regulate flow from the irrigant reservoir 254 to the irrigation port 248. The irrigation valve 378 can be configured to prevent the irrigant 257 from exiting the irrigation port 248 at an excessive pressure. The velocity of the irrigant 257 flow stream can be prevented from exiting the device 2 at an excessive velocity.

Figure 40:
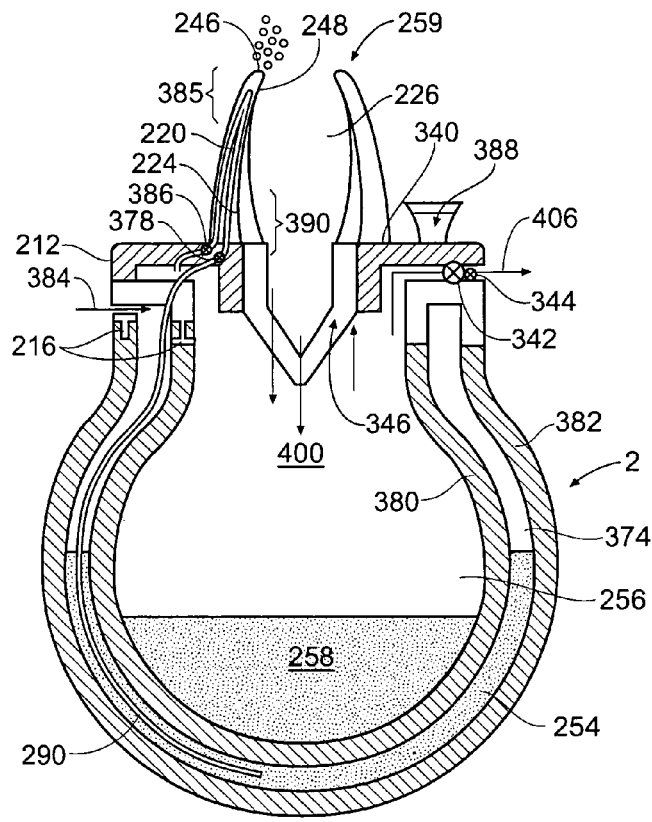
FIG. 40 is partial cut-away view and partial schematic diagrams of a variation of the irrigation and aspiration device.
Figure 41:
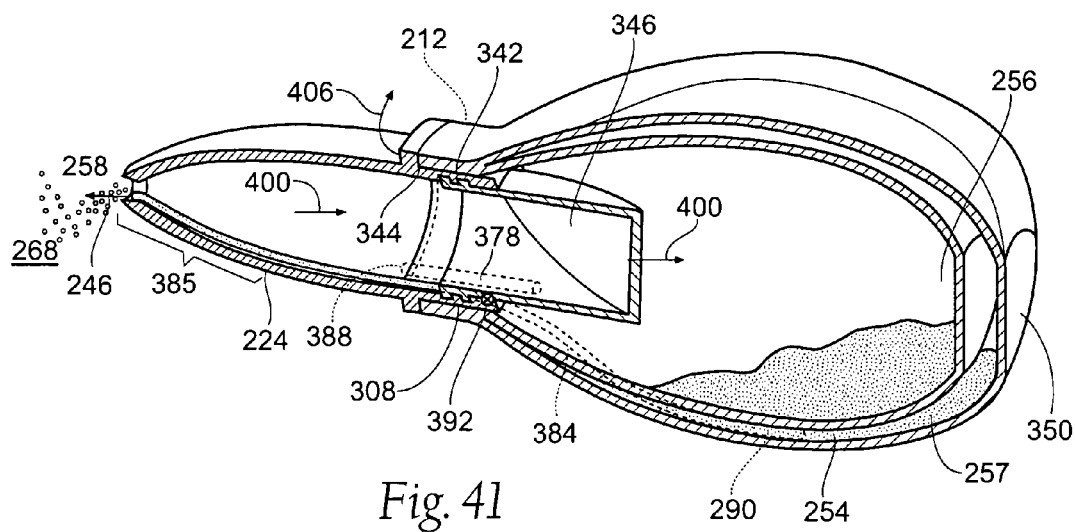
FIG. 41 is partial cut-away view, partial see-through view and partial schematic diagram of a variation of the irrigation and aspiration device.

FIGS. 40 and 41 illustrate that the aspirant reservoir 256 can be in an inner irrigant reservoir wall 380. The irrigant reservoir 254 can be between an inner irrigant reservoir wall 380 and an outer irrigant reservoir wall 382. The inner irrigant reservoir wall 380 and the outer irrigant reservoir wall 382 can be rigid, resilient or deformable.

The device 2 can have an atomization intake port 384 on the outside surface of the device 2. The atomization intake port 384 can be in fluid communication with the atomization fluid reservoir 374. The atomization intake port 384 can have a check valve configured to allow one-way flow from the atomization intake port 384 to the atomization fluid reservoir 374.

The atomization valve 386 can regulate flow between the irrigant reservoir 254 to the atomization channel 220. The atomization channel 220 can have a venturi 385 configuration adjacent to the irrigation port 248. The venturi 385 can atomize the irrigant 257 and/or increase the speed of the atomization gas.

The irrigant valve 378 can regulate flow between the irrigant reservoir 254 and the irrigant channel 224. The irrigant valve 378 can be a check valve. The irrigant valve 378 can prevent flow from the irrigant channel 224 to the irrigant reservoir 254. The irrigant valve 378 can permit substantially free flow from the irrigant reservoir 254 to the irrigant channel 224. The irrigant valve 378 can restrict the flow from the irrigant reservoir 254 to the irrigant channel 224 except under high pressure differentials, for example a pressure differential greater than about 25 mmHg (0.5 psi), more narrowly a pressure differential greater than about 100 mmHg (2 psi), more narrowly a pressure differential greater than about 260 mmHg (5 psi), more narrowly a pressure differential greater than about a pressure differential greater than about 760 mmHg (14.7 psi), for example for a pressure differential greater than about 1600 mmHg (30 psi).

An irrigant intake port 388 can be in fluid communication with the irrigant reservoir 254. The irrigant intake port 388 can have a check valve configured to allow one-way flow from the irrigant intake port 388 to the irrigant reservoir 254. The irrigant reservoir 254 can be filled by introducing irrigant 257 through the irrigant intake port 388.

The aspiration channel 226 can have a valve transition zone 390. The valve transition zone 390 can be configured as a smooth transition from the inner wall of the aspiration channel 226 to the inner wall of the aspirant valve 346.

An exhaust valve 342 can regulate flow between the aspirant reservoir 256 and the exhaust port 344. The exhaust port 344 can be covered and uncovered by the user (e.g., by a digit 76, such as the thumb 77) during use. The exhaust can flow from the aspirant reservoir 256 and out the exhaust port 344, as shown by arrow.

The device 2 shown in FIGS. 40 and 41 can be squeezed to deliver the irrigant 257. Releasing the device 2 from a squeezed configuration can aspirate.

FIG. 41 shows that the irrigant 257 and atomization fluid can be mixed a mixing valve 392. The mixing valve 392 can be upstream from the atomization port 246.

FIG. 42 illustrates that the device 2, such as the variation shown in FIG. 36, can be actuated to irrigate by rotating 508 a trigger 245 on a hinge, for example with one or more digits 76 (e.g., the forefinger and/or middle finger). The aspirant reservoir 256 can be completely or partially emptied by compressing 241, as shown by arrows, the aspirant reservoir 256, for example with the thumb 77, ring finger, pinky and palm 74. The aspirant 258 can be drawn into the aspiration port 260 by releasing the compressed aspirant reservoir 256.

Variations of the device 2, such as those shown in FIGS. 36 through 42, can be actuated by squeezing (e.g., for irrigation) and releasing (e.g., for aspiration) all or part of a resilient portion of the device 2, such as a bulb 314.

B. Remote Head

FIG. 43 illustrates that the device 2 can have a head 14 that can be coupled to a body 4 with a lead 200, and/or the head 14 can be coupled to a separate vacuum source, such as wall vacuum and/or a portable vacuum pump, for example. This embodiment may incorporate any and all the features disclosed in the description of the device 2, except this embodiment comprises the additional feature of providing a remote head 14.

The lead 200 can carry the irrigant channel 36, and/or aspirant channel 46, and/or coupling to control 10, and/or coupling to a wall vacuum source and/or coupling to a portable vacuum pump, or combinations thereof. The lead 200 can be flexible. The lead 200 can be retractable into the body 4, for example with a spring-loaded retraction mechanism. The lead 200 can be coiled.

The head 14 can have a removably attached aspirant reservoir 40 and/or irrigant reservoir 30. The head 14 may include a handle 202 to aid in use and control of the head 14 and/or body 4. The head 14 and/or the handle 202 may include a pump 204 to produce the irrigant pressure necessary to expel irrigant. The head may be squeezed to produce the irrigant pressure necessary to expel irrigant.

The body 4 can take on any convenient shape, and may have a flat base 206 for support. The body 4 can be attached to a surface such as a flat surface (e.g., floor, table, crib), for example with screws, nails, brads, bolts or combinations thereof. The body 4 can be weighted with ballast and/or have a clamp (e.g., to stabilize).

C. Dual Tip Nozzle

Figure 44:
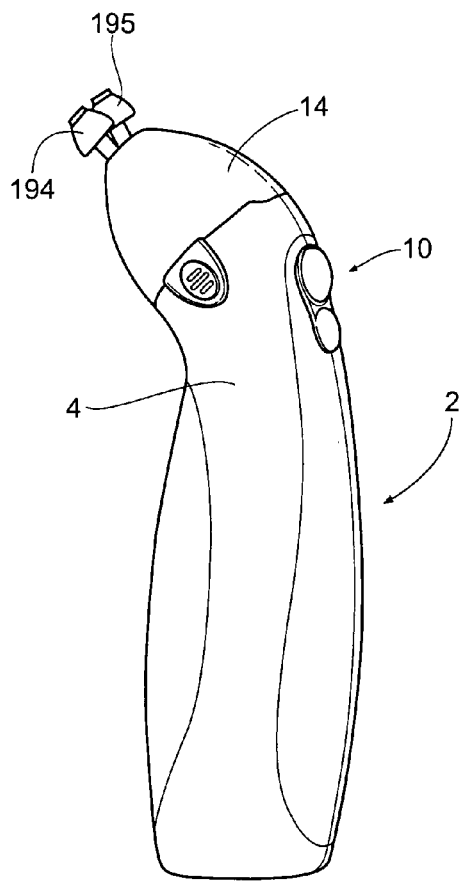
FIG. 44 is a perspective view of a variation of an irrigation and aspiration device, showing the device including dual nozzles.

FIG. 44 illustrates that the device 2 can have a head 14 that includes more than one nozzle, i.e., flexible tips, as two flexible tips 194, 195 are shown. Some embodiments may incorporate any and all the features disclosed in the description of the device 2, except some embodiments include the additional feature of dual flexible tips 194, 195.

Figure 45:
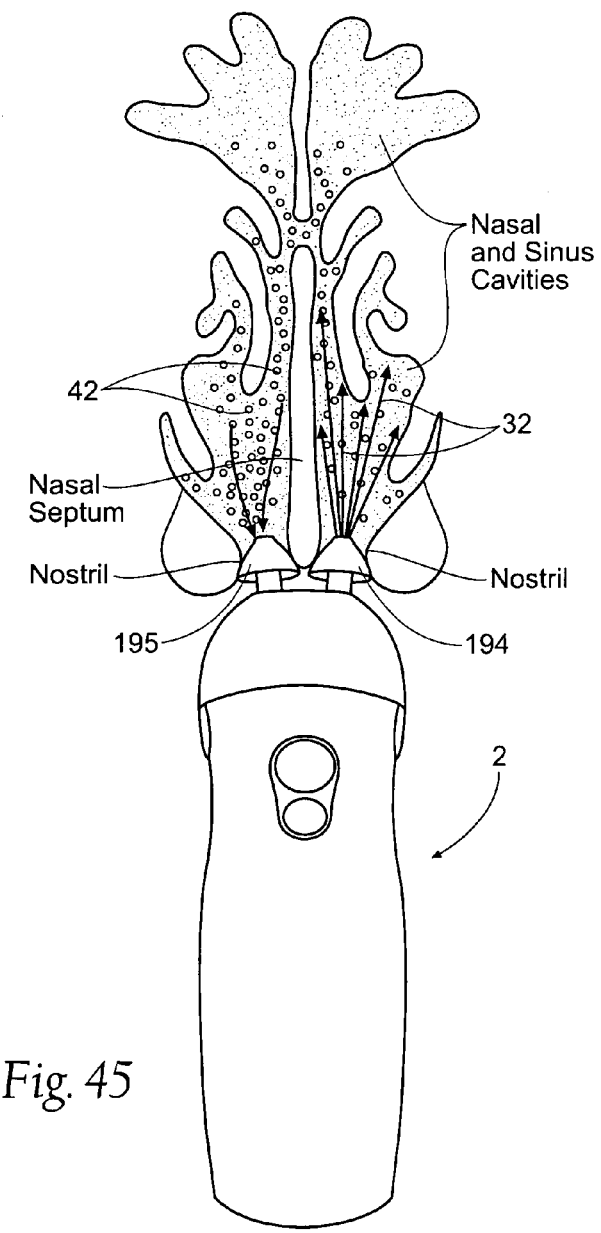
FIG. 45 is a generally superior anatomical view in section of a patient's nasal and sinus cavities, and showing the use of a variation of an irrigation and aspiration device comprising dual tips, and irrigating from one tip, through the nasal and sinus cavities, and aspirating from the other tip.

Simultaneous or intermittent irrigating and aspirating the target region, e.g., the nasal and/or sinus cavities from one nostril to the other, may be advantageous. Dual tips 194, 195 allow irrigant 32 to be expelled into one nostril while simultaneously or intermittently being aspirated out the other nostril (see FIG. 45).

In some embodiments, the irrigation fluid 32 may be provided as a fine mist to a high volume stream of irrigant 32. Irrigant 32 may be expelled continuously or in a pulsed fashion. Aspiration may be continuous or intermittent. The process of irrigation and aspiration may be automatically or manually timed for a cleaning cycle (i.e., irrigation and aspiration).

D. Alternative Pressure

Figure 46:
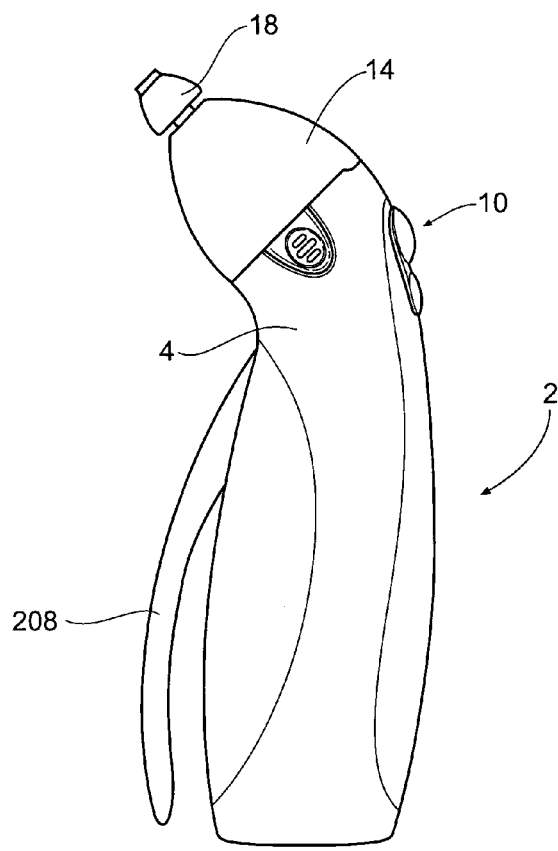
FIG. 46 is a side view of a variation of an irrigation and aspiration device, showing the device including a trigger or handle for pressure generation and controlled release.

FIG. 46 illustrates that some embodiments of the device 2 can have a pump configuration comprising a trigger or handle 208 adapted to generate a sufficient pressure for the aspiration and/or irrigation functions. The handle 208 may be used to generate either or both positive and negative pressures. The pressure may be stored in a container or canister 210 as it is generated, and then released via the controls 10, for example, or the pressure may be generated as needed. The handle 208 may be coupled to a pump, such as pump 8 and/or 11, as previously described, and/or the handle may be coupled to a bellows or baffle combined with a one way valve, or alternatively a flywheel pump design to generate a relatively constant pressure, e.g., vacuum.

Figure 47:
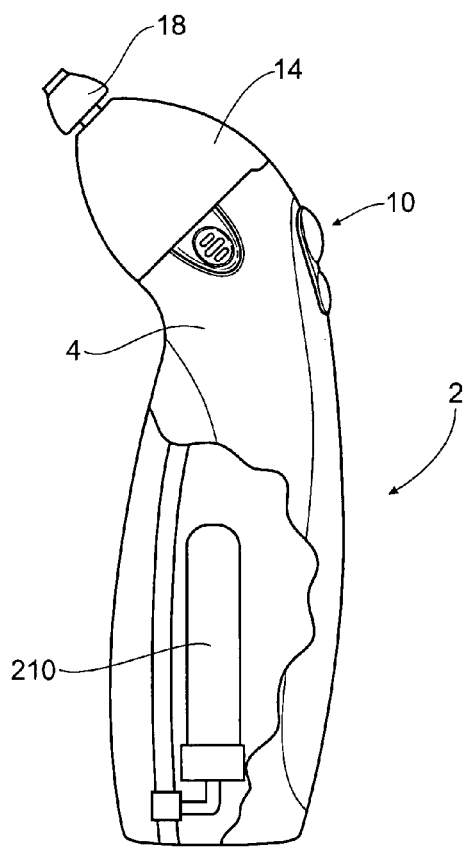
FIG. 47 is a side view of a variation of an irrigation and aspiration device, showing the device including a canister for storage of compressed gas for pressure generation and controlled release.

FIG. 47 illustrates that some embodiments of the device 2 can have a pump configuration comprising a canister 210 or other supply of compressed gas (e.g., air, carbon dioxide, oxygen, and/or nitrogen). Embodiments of the device 2 can be configured to controllably generate a supply of compressed gas, and then controllably release the compressed gas to produce a venturi effect, thereby creating sufficient pressure for the aspiration and/or irrigation functions.

In some embodiments, the compressed gas is manually generated by the user. For example, handle 208 may be used to generate a gas under pressure for immediate use, or for storage in a canister 210. As previously described, a resilient container, such as an elastomeric bulb 314 may be used to create and/or store a compressed gas.

In some embodiments, the compressed gas may be removable and replaceable, and/or automatically generated. For example, canister 210 may be a removable and replaceable snap-in canister containing a supply of compressed gas, and when the supply of compressed gas is exhausted, the canister 210 is replaced with a new canister. The recharger base 62 may also comprise a high pressure pump that recharges canister 210 with a fresh supply of compressed gas.

Figure 48A:
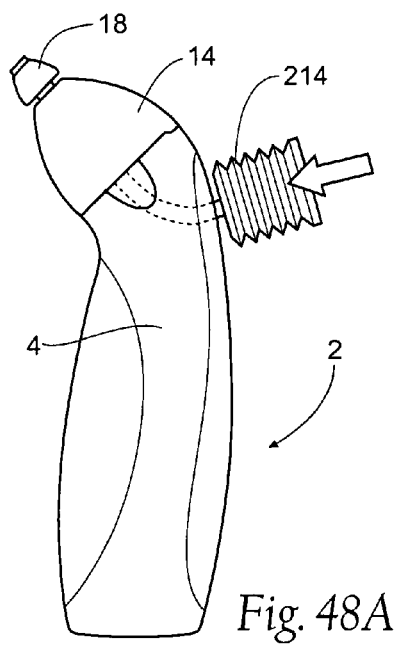
FIGS. 48A through 49B are side views of a variation of an irrigation and aspiration device, showing the device including a bellows for pressure generation and controlled release.
Figure 48B:
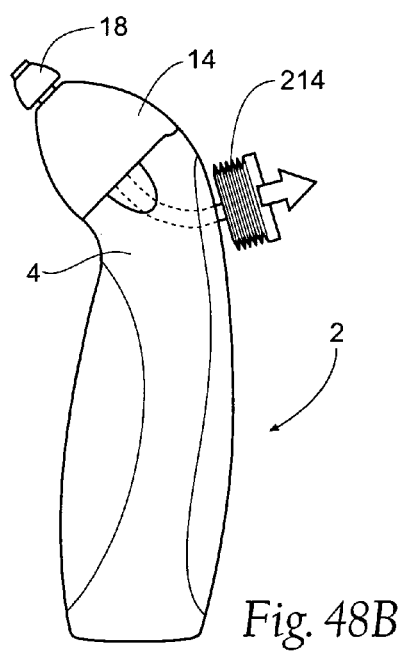
Figure 49A:
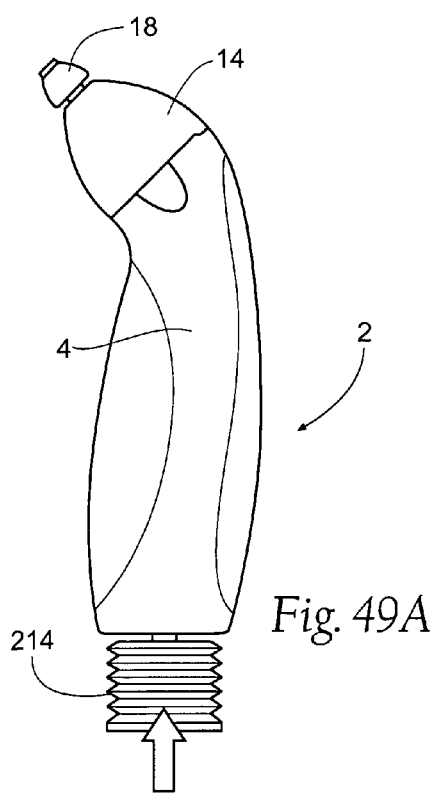
Figure 49B:
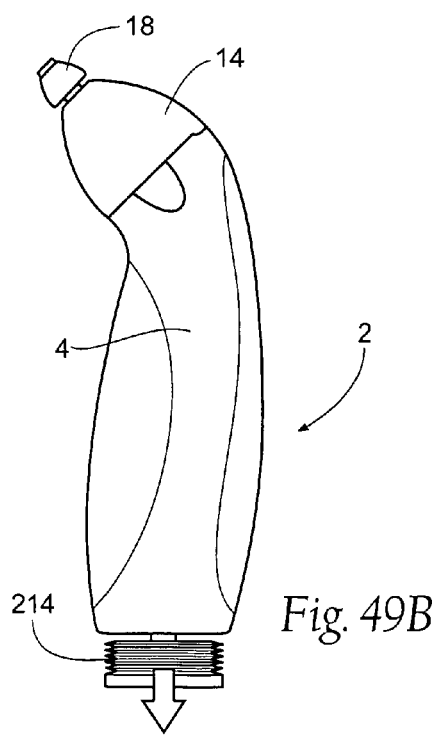

FIGS. 48A through 49B illustrate alternative embodiments of the device 2 can have a pump configuration comprising a baffle or bellows 214 adapted to generate a sufficient pressure for the aspiration and/or irrigation functions. The bellows 214 may be used to generate either or both positive and negative pressures. As previously described, the pressure may be stored in a container or canister 210 as it is generated, and then released via the controls 10, for example, or the pressure may be generated as needed. The bellows 214 may be coupled to a pump, such as pump 8 and/or 11, as previously described, and/or the bellows 214 may be combined with a one way valve to generate a relatively constant pressure, e.g., vacuum. FIGS. 48A and 48B show an embodiment where the bellows are located on the device 2 where the bellows are easily controlled with the user's hand or digits. FIGS. 49A and 49B show an embodiment where the bellows are located on the device 2 near or at its base.

VI. Instructions for Use

The instructions for use 58 can direct the use of an irrigation and aspiration device 2, including a device 2 adapted to be hand-held and controllable with one or more digits (i.e., fingers 76 or thumb 77). The instructions for use may include instructions for irrigation and/or aspiration in a nasal cavity, for example. The instructions for use may also include instructions for using the head 14 as a diagnostics device, such as for testing the contents of the head 14 and/or aspiration reservoir 40, for example, as will be described below.

FIGS. 26 through 29 show representative embodiments of the steps that representative instructions for use 58 can incorporate or direct.

A. Irrigate and Aspirate

The instructions may include a series of steps that can be followed to carry out the irrigation and aspiration procedures. It is to be appreciated that the device 2 may be used for only irrigation, or only aspiration, or irrigation, then aspiration, or aspiration, then irrigation, or irrigation and aspiration simultaneously. The instructions may be provided for the benefit of the person controlling the device 2, which may be a user, or a patient, or the user may be the patient. These steps may include, but are not limited to:

(i) confirm the irrigation and aspiration device 2 contains a desired supply of irrigation fluid 32;

(ii) confirm the device 2 is operational, which may include testing the irrigation function and the aspiration function by pressing the button 112 to confirm the flow of irrigation fluid 32 and that aspiration suction is available;

(iii) position the flexible tip 18 at the vestibule of the nostril, and apply an inward force to gently seal the bulbous tip 82 against the nostril; a variety of positions may be used, for example, with use on a baby, the user may sit on a bed with the baby between the users legs, and holding the baby's head down with one hand, use the device 2 with the other hand; or, swaddle the baby in a blanket, and place the baby on a changing table, hold the head with one hand and use the device 2 with the other; or, cradle the baby with the head in the user's armpit and place an arm over the baby's arms and use the device with the other;

(iv) using the controls 10, apply a downward force 114, e.g., with the thumb 77, on a first portion of the button 112 to expel irrigation fluid from the irrigation reservoir 30, through the tip 18, and into the nasal and/or sinus cavities;

(v) again using the controls 10, apply a downward force 116, e.g., with the thumb 77, on a second portion of the button 112 to produce an aspiration pressure to draw irrigation fluid 32 and mucus (i.e., aspiration fluid 42) from the nasal and/or sinus cavities through the tip 18 and into the aspiration reservoir 40;

(vi) steps (iv) and (v) may be repeated as desired, while confirming the irrigation reservoir 30 contains a supply of irrigation fluid 32, and the aspiration reservoir 40 contains space for additional aspiration fluid 42;

(vii) if necessary, the irrigation reservoir 30 may be refilled with irrigation fluid 32 (or the irrigation reservoir 30 may be removed and replaced with a full irrigation reservoir 30, and the aspiration reservoir 40 may be emptied (or the aspiration reservoir 40 may be removed and replaced with an empty aspiration reservoir 40);

(viii) optionally, steps (iv) and (v) may be followed simultaneously to simultaneously irrigate and aspirate.

(ix) after use, the irrigation reservoir 30 and/or the aspiration reservoir 40 may be removed, and/or replaced and/or cleaned for reuse.

The instructions may include a series of steps that can be followed to carry out the irrigation and aspiration procedures for displacement of sinus content and complete cleansing of the sinus cavity. These steps may use the venture effect of rapidly moving irrigation fluid as it goes by the sinus ostea and thereby displace the sinus content (i.e., mucus) with irrigation fluid, approximating the Proetz displacement procedure.

These steps may include the steps as described above, and may also include, but are not limited to:

(i) confirm the irrigation and aspiration device 2 contains a desired supply of irrigation fluid 32;

(ii) confirm the device 2 is operational, which may include testing the irrigation function and the aspiration function by pressing the button 112 to confirm the flow of irrigation fluid 32 and that aspiration suction is available;

(iii) have the patient laying down with the head in the snuff position.

(iv) position the flexible tip 18 at the vestibule of the nostril, and apply an inward force to gently seal the bulbous tip 82 against the nostril;

(v) using the controls 10, apply a downward force 114, e.g., with the thumb 77, on a first portion of the button 112 to expel irrigation fluid from the irrigation reservoir 30, through the tip 18, and into one side of the nose to fill the nasal cavity;

(vi) simultaneously or just afterwards, again using the controls 10, apply a downward force 116, e.g., with the thumb 77, on a second portion of the button 112 to produce an aspiration pressure to apply suction to the other side of the nose while intermittently occluding the saline irrigated nostril, and apply suction for approximately three to five seconds at a time until satisfied of evacuation. It may be helpful to have the patient say "K-K-K-K" while applying the suction as it closes the vallecula and allows a more closed circuit.

B. Diagnose Contaminated Fluids

The instructions may include a series of steps that can be followed to carry out a contaminated fluids diagnostics procedure. It is to be appreciated that the diagnostics procedure may be performed automatically by the diagnostic means 22, as described below, or the aspirant reservoir 40 and/or head 14 may be removed and sent to a lab for further testing. These steps may include, but are not limited to:

(i) use of the device 2 (see instructions above) for at least aspiration to collect a supply of aspiration fluid 42 within the aspiration reservoir 40;

(ii) present the aspiration fluid 42 directly to the diagnostic means 22, or by first drawing the fluid 42 into a sample chamber 92, which may be accomplished by shaking the head 14 (or the device 2) so as to draw the fluid sample 42 into the chamber 92, or by capping the flexible tip 18 with the cap 20, or finger 76, and actuating the aspiration function again so as to cause an occluded suction, which draws the aspiration fluid 42 into the chamber 92;

(iii) once a predetermined amount of fluid 42 is within the chamber 92, which may be predetermined by the size of the chamber, it may be available to an analysis system 90 as part of the diagnostic means 22 for testing, or the fluid 42 may be combined with a reagent from the chamber 92 or other chamber to form an aliquot to then be delivered to the analysis system 90;

(iv) the sample or aliquot may then be presented to the analysis system 90 by taking an action such as manually popping a blister 94, or the push of a button, or movement of a switch, on the side of the head 14 to allow entry of the sample or aliquot into and/or onto the analysis system 90;

(v) the diagnostic means 22 may then display and/or present a result or results of the test(s), which may be displayed as a change of color of an indicator on or in the diagnostic means 22 and/or head 14, or a test strip may be removed from the diagnostic means, or visible within the head 14 and/or aspiration reservoir 40, for example;

(vi) the head 14 and/or diagnostic means 22 may then be disposed of, or the head 14 and/or diagnostic means 22 may be sent to a lab for any additional actions.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A kit of devices to provide an irrigation and aspiration system, the kit comprising:
a head,
an aspirant reservoir within the head, the aspirant reservoir adapted to contain aspirated fluid,
at least one nozzle extending from the head, the nozzle including an aspirant lumen, the aspirant lumen adapted to provide fluid communication between the aspirant reservoir and an aspirant port,
a diagnoser within the head for testing the aspirated fluid, wherein the diagnoser comprises an actuator on the head,
a body, the body adapted to releasibly couple to the head, the body including a pump adapted to draw fluid into the aspirant port and through the aspirant lumen and into the aspirant reservoir,
a controller to operate the pump adapted to draw aspirated fluid, and
instructions for use describing the operation and use of the irrigation and aspiration system, the instructions comprising the operations of: positioning the nozzle on or in an orifice, using the controller to activate the pump to draw fluid from the orifice, through the nozzle, and into the aspirant reservoir, using the hand-held test device to provide a sample of the aspirated fluid to the diagnoser, testing the aspirated fluid while the fluid remains in the housing, and providing an indication of the results of the testing.

2. The kit of claim 1, further comprising a hand-held housing, the housing including the head and a base, the head and base being adapted to be releasably coupled to each other at an interface region.

3. The kit of claim 2, further comprising a barrier within the housing adapted to retain liquid in the aspirant reservoir and allow gas to pass out of the aspirant reservoir.

4. The kit of claim 1, wherein the diagnoser comprises at least one of a test strip, an electrical chip, a chemical, and a genetic plate.

5. The kit of claim 1, wherein the diagnoser is contained within the head.

6. The kit of claim 1, wherein the diagnoser is adapted to provide test results.

7. The kit of claim 1, wherein the diagnoser is contained within the aspirant reservoir.

8. The kit of claim 7, wherein the diagnoser includes a sub-chamber within the aspirant reservoir, the sub-chamber adapted to deliver a predetermined volume of aspirated fluid to the diagnoser.

9. The kit of claim 8, wherein the sub-chamber includes a port in fluid communication with the aspirant reservoir that allows negative pressure to control sub-chamber filling.

10. The kit of claim 8, further comprising a flexible portion adapted to be pressed to facilitate at least one of sub-chamber filling and evacuation of the aspirated fluid to the diagnoser.

11. The kit of claim 8, further comprising a flexible portion adapted to induce the addition of a diagnostic test reagent/primer into the sub-chamber to then be delivered to the diagnoser.

12. The kit of claim 2: further comprising a power source within the housing.

13. The kit of claim 1, wherein the diagnoser accommodates microbiologic tests including influenza A and B, avian flu, RSV (respiratory syncytial virus), adenovirus, Legionella, CNV, EBV, Group A beta hemolytic *streptococcus, S. pneumoniae, N. meningitides*, mycoplasma, *Staphloccus aureus*, Malaria, HIV, rhinovirus, coccsackie virus, smallpox, anthrax, botulinum toxin, ricin, ebola, rabies, brucellosis, (plague) yersinia pestis, *coxeilla burnetti* (Q fever), T2 mycotoxins, *francisella tularensis* (tularemia), viral equine encephalitis, viral hemorrhagic fever, and *burkholdria mallei* (glanders).

14. The kit of claim 1, wherein the diagnoser accommodates toxicologic and/or chemical tests including amphetamines, cocaine, opiates, phencyclidine, tetrahydrocannabinol, acetaminophen, barbiturates, benzodiazepines, methadone, propoxyhenone, tricyclic antidepressants, calcium channel blockers, ethyl alcohol, ethylene glycol, ketones, glucose, hypoglaecemics, cytokines, interleukins, insulin, Hemoglobin A1C, electrolytes, human choreonic gonadotropin (pregnancy test), thyroid-stimulating hormone (TSH), T3 blood test, T4 blood test, c-reactive protein (CRP), and erythrocyte sedimentation rate (ESR).

15. The kit of claim 1, wherein the diagnoser accommodates real time polymerase chain reaction tests and/or immunoassays for viruses, bacteria, and cancers.

16. The kit of claim 1, further comprising the pump within the housing adapted to expel irrigation fluid from an irrigant reservoir, the irrigant reservoir adapted to contain irrigation fluid.

17. The kit of claim 1, wherein the nozzle further comprises an irrigant lumen adapted to provide fluid communication between an irrigant reservoir and an irrigant port.

18. The kit of claim 2, wherein the interface region comprises a non-fluid flow component and a gas flow component, and wherein the interface region couples the head to the base.

19. The kit of claim 2, wherein the interface region comprises a seal between the head and the base, wherein the seal is adapted to allow a force exerted on the base to be transferred to the head, and wherein the seal is adapted to allow an aspiration pressure from the base to draw a gas out of the aspiration reservoir and into the base.

* * * * *